United States Patent [19]

Martin

[11] Patent Number: 5,703,221

[45] Date of Patent: Dec. 30, 1997

[54] STEALTH VIRUS NUCLEIC ACIDS AND RELATED METHODS

[76] Inventor: William John Martin, 1634 Spruce St., South Pasadena, Calif. 91030

[21] Appl. No.: 463,115

[22] Filed: Jun. 5, 1995

Related U.S. Application Data

[63] Continuation-in-part of Ser. No. 157,811, Nov. 23, 1993, which is a continuation-in-part of Ser. No. 887,502, May 22, 1992, which is a continuation-in-part of Ser. No. 704,814, May 23, 1991, and Ser. No. 763,039, Sep. 20, 1991.

[51] Int. Cl.$^6$ .......................... C12N 15/34; C12P 19/34
[52] U.S. Cl. ................. 536/23.72; 435/91.2; 435/235.1; 435/240.2
[58] Field of Search .................... 435/5, 235.1, 239, 435/240.2, 240.25, 91.1, 91.2; 436/63; 536/23.72

[56] References Cited

U.S. PATENT DOCUMENTS

| | | | |
|---|---|---|---|
| 4,683,195 | 7/1987 | Mullis et al. | 530/324 |
| 4,683,202 | 7/1987 | Mullis | 435/91.2 |
| 4,889,818 | 12/1989 | Gelfand et al. | 435/194 |

FOREIGN PATENT DOCUMENTS 9220787  11/1992  WIPO.

OTHER PUBLICATIONS

Cowley et al., "A chronic fatigue cover–up", Newsweek, Apr. 22, 1996, p. 62.
Ablashi et al., "Genomic Polymorphism, Growth Properties and Immunologic Variations in Human Herpesvirus 6 Isolates," *Virology* 184:545–552 (1991).
Ablashi et al., "Utilization of Human Hematopoietic Cell Lines For the Propagation and Characterization of HBLV (Human Herpesvirus 6)," *Int. J. Cancer* 42:787–791 (1988).
Archard et al., "Postviral Fatigue Syndrome: Persistence and Enterovirus RNA in Muscle and Elevated Creatine Kinase," *The Royal Society of Medicine* vol. 81 (1988).
Buchwald et al., "A Chronic Illness Characterized by Fatigue, Neurologic and Immunologic Disorders and Active Human Herpesvirus Type 6 Infection," *Annals of Internal Medicine* 116:103–113 (1992).
Chee et al., "Analsyis of the Protein Coding Content of the Sequence of Human Cytomegalovirus Strain AD169," *Current Topics in Microbiology and Immunology* 154:126–169 (1990).
Cohen et al.,"Okadaic Acid: A New Probe for the Study of Cellular Regulation," *TIBS* 15:98–102 (1990).
Dale et al., "The Inoue–Melnick Virus, Human Herpesvirus Type 6, and the Chronic Fatigue Syndrome," *Annals of Internal Medicine* 110:92–93 (1989).
Dale et al., "Chronic Fatigue Syndrome: Lack of Association with Hepatitis C Virus Infection," *J. Medical Virology* 34:119–121 (1991).
DeFreitas et al., "Retroviral sequences related to human T–lymphotropic virus type II in patients with chronic fatigue immune dysfunction syndrome," *Chemical Abstracts* 114:No. 205331c (1991).

DeFreitas et al., "Retroviral Sequence Related To Human T–lymphotropic Virus Type II in Patients with Chronic Fatigue Immune Dysfunction Syndrome," *Proc. Natl. Acid. Sci. USA* 88:2922–2926 (1991).
Demitrack et al., "Evidence for Impaired Activation of the Hypothalamic–Pituitary–Adrenal Axis in Patients with Chronic Fatigue Syndrome," *Journal of Clinical Endocrinology and Metabolism* 73:1224–1234 (1991).
DiLuca et al., "The Replication of Viral and Cellular DNA in Human Herpesvirus 6–Infected Cells," *Virology* 175:199–210 (1990).
Ehrlich et al., "Detection of Human T–Cell Lymphoma–Leukemia Viruses," *PCR Protocols: A Guide to Methods and Applications*, Ch. 39, pp. 325–336 (1990).
Feinberg and Vogelstein, "A technique for radiolabeling DNA restriction endocnuclease fragment to high specific activity," *Anal. Biochem.* 137:266–267 (1984).
Freshney, "Ch. 10—Maintenance of the Culture–Cell Lines," *Culture of Animal Cells: A Manual of Basic Technique*, Alan R. Liss, Inc., New York, pp. 127–136 (1987).
Gupta and Vayuvegula, "A Comprehensive Immunological Analysis in Chronic Fatigue Syndrome," *Scand. J. Immunol.* 33:319–327 (1991).
Ham, R.G., "An Improved Nutrient Solution for Diploid Chinese Hamster and Human Cell Lines," *Exp. Cell Research* 29:515–526 (1963).
Ho, M., *Cylomegalovirus: Biology and Infection*, 2nd ed., pp. 75–76, Plenum Medical Book Company, New York, N.Y. (1991).
Holmes, G.P., "Defining the Chronic Fatigue Syndrome," *Reviews of Infectious Diseases* 13(Suppl. 1):553–555 (1991).
Holmes et al., "Chronic Fatigue Syndrome: A Working Case Definition," *Annals of Internal Medicine* 108:387–389 (1988).
Iscove and Melchers, "Complete Replacement of Serum By Albumin, Transferrin and Soybean Lipid in Cultures of Lipopolysaccharide–Reactive B Lymphocytes," *J. Exp. Med.* 147:923–933 (1978).
Kendell, R.E., "Chronic Fatigue Viruses and Depression," *The Lancet* 337:160–161 (1991).
Landay et al., "Chronic Fatigue Syndrome: Clinical Condition Associated with Immune Activation," *The Lancet* 338:707–712 (1991).

(List continued on next page.)

*Primary Examiner*—James Ketter
*Assistant Examiner*—Irem Yucel
*Attorney, Agent, or Firm*—Lyon & Lyon LLP

[57] ABSTRACT

A method of detecting a stealth virus is provided by culturing a sample under conditions in which any stealth virus in the sample is able to induce a cytopathic effect. A method for culturing a virus is also provided by (a) cocentrifuging a sample of said virus with a permissive cell line of indicator cells; (b) inoculating the cell mixture into culture vessels; (c) adding viral enhancing medium to the culture; and (d) detecting in vitro a cytopathic effect in the permissive cell line.

1 Claim, 24 Drawing Sheets

OTHER PUBLICATIONS

Martin, W.J., "Ch. 27—Detection of Viral Related Sequences in CFS Patients Using the Polymerase Chain Reaction," *The Clinical and Scientific Basis of Myalgic Encephalomyelitis/Chronic Fatigue Syndrome*, pp. 278–281, Hyde et al. eds., The Nightingale Research Foundation, Ogdensburg, New York (1992).

Martin, W.J., "Ch. 34—Viral Infection in CFS Patients," *The Clinical and Scientific Basis of Myalgic Encephalomyelitis/Chronic Fatigue Syndrome*, pp. 325–3271, Hyde et al. eds., The Nightingale Research Foundation, Ogdensburg, New York (1992).

Martin et al., "Cytomegalovirus–Related Sequence in an Atypical Cytopathic Virus Repeatedly Isolated from a Patient with Chronic Fatigue Syndrome," *The American Journal of Pathology* 145(2):440–451 (1994).

Niks and Otto, "Towards an Optimized MTT Assay," *Immunological Methods* 130:149–151 (1990).

Palca, J., "On the Track of an Elusive Disease," *Science* 254:1726–1728 (1991).

Palca, J., "Does a Retrovirus Explain Fatigue Syndrome Puzzle?" *Science* 249:1240–1241 (1990).

Rethwilm et al., "Infectious DNA of the Human spumaretrovirus," *Nucleic Acids Research* 18:733–738 (1990).

Sanger et al., "DNA sequencing with chain–terminating inhibitors," *Proc. Natl. Acad. Sci. USA* 74:5463–5467 (1977).

Schirmer et al., "Differentation Between Two Distinct Classes of Viruses Now Classified as Human Herpesvirus 6," *Proc. Natl. Acad. Sci. USA* 88:5922–5926 (1991).

Shafran, S. D., "The Chronic Fatigue Syndrome," *The American Journal of Medicine* 90:730–738 (1991).

Shepherd, C., "Myalgic Encephalomyelitis—Is It a Real Disease?" *The Practitioner* 233:41–46 (1989).

Wang et al., "Single primer–mediated polymerase chain reaction: application in cloning of two different 5'–untranslated sequences of acidic fibroblast growth factor MRNA," *DNA Cell Biol.* 10:771–777 (1991).

Welch et al.,"Cytomegalovirus Homologs of Cellular G Protein–Coupled Receptor Genes Are Transcribed," *J. Virology* 65:3915–3918 (1991).

Werner J., "Isolation of Foamy Virus From Patients with De Quervain Thyroiditis," *Lancet* 11:258–259 (1979).

Yousef et al., "Chronic Enterovirus Infection in Patients with Postviral Fatigue Syndrome," *Lancet* i:146–150 (1988).

Plasmid: 1

```
GAATTCTGGT ATGAGACGGA CGGCACGCCG GTTCAATCCC GGAAATTATT         50
ACAATGTCGG CGGCAATTCC AAATTCTATG GCGCAGTGCT GGTGCGCTAT        100
CGGCGAAGAT TTTGAGGAGC TTGCGCATCT TGAAGGCGTG TCTCCGGCAT        150
GGCCTTTTGG         SEQ ID NO. 7                               160
```

Plasmid: 2

```
TANGTACACN CNCTNGAGCT CTCGCTNTCT AGTAACAAAG GCTCAGTACG         50
TGGNAAGGGG TGTNGCGTCA CGCCTACACA CCTGGGCTGC TCGACCATCA        100
TAACGTGTGT GATCTGGAGG GGCCTTCTAN ACCTGTCGTN GNTGNGGACC        150
CCNCAGNTTT NTATCNGTAG CATACTNACN NAACGCTCTA CCNCNTCNAC        200
ATTTGANNCN TTCCTATTTT TTTCCCCCCA CACTTTTTNT TTTTCANTTT        250
ACCTCTNANC TANTTTCCNA CATTCTNCNN NNNNCATNTC TNCATCCCCC        300
ACTAATNTTC TTCANTCNNT TATNNATCAA NCCNCNNTCN CACNTTCCA         350
TTNCAACCAC CNANNNTNTT ANCTCNCTTA NNNTTTCTCC TTNNNACTAT        400
CAATCTTNTN TNACTNNACA CCNANCACTC NAANCTCCAT TTTTAAANNN        450
TNNANNTNTC NTNNCCNTTN TNTAACCCNC TTNANCNTAC NTCNNTAATT        500
NCTTTTCCNA ANATTNANNC CNCACCNANT TATNNNTCAC CANNCAACAT        550
NTNNTATNTC TANNNNANNN TTNTTTNNCN TAAACNTCCT ACTTCTANNT        600
NTNCANNTAA TANAATNCTA NACTNCTCAC CTTNAACNNC TNCACTNCAN        650
ACNTNACNNN NTCNNNTTTT AAACTNCNNT NNTNNNTTTT TANATCCCNT        700
CTCACTTNAT CTNATAANNC NNATCCATNT TTGNCCNCTC ATCTATCNTA        750
CTNNNNACNC NTNNCTNCCN TCTTNCTCAT CCAA     SEQ ID NO. 8        784
```

Plasmid: 3

```
TGTTTTNCAN CTTCTCAAGG GACCCCCCCC CGAGGAAGAC GGTATCGATA         50
AGCTTGATAT CGAATGCCCT GCAGNCCGGG GGNATCCACT AGTTCTAGAG        100
CGGNCGCCAC CGNGGTGGAG CTCGAGACAG GTGNCGCGAT ATGCCNCGGC        150
CTGGCACCGC GAACACAGCG GCCCCTGGCC GTGACACGTG AGCTTCAGGA        200
GTCGCGGGAT AGTGACGGAG CGCACCACCA CGGTGGAATC GCACGTCCGC        250
GCAGAGCACG GTAGAATGAT GTCAAACGTG ACGAGGTGGT CATAGACCGC        300
ACACGCGGTG TTCANCCCCA AGACTGNCTT CCAACCAAAC CGNAAACAAC        350
GTTGCCCACA NATCGTCTCA GAGACANCTT CGTAAACACG TTCTTTTAAT        400
GACACGCTGA CTTCACAAA AGAGAACAGT GCANCAGTTC GGCGTTAGTA         450
TTGAAANTGA CACTCTTTTC TTGGCGGTCT CTATANTAGA ACATAGAGTT        500
AAGGGGGGAA TTCTGCTCGC AGNGNAGGTT CTCCTGGCCA AGTTCAAGCA        550
GGGGNCGAAT TCGGANAAC ACGGNGACAG GATCTTGGTT TAGTGGNGTC         600
NACTCAGNGA AAAGCACAGG NGGTTTATAC GTTCTTTNTC CCGAGNCNCC        650
ATCTATATTT GGTGTCNGGC CCNTTTTTTT     SEQ ID NO. 9             680
```

Plasmid 4:

```
GAGCTCGCCT CTGGCTGCAC CTGTGGGGGG CTCTTTCCAT GTCCTCACAC         50
GTCTCTGTCA CGTCCGCCCT CGTACAGNAT CACCGCTCTC CTAGCTTTCC        100
CAATTTTGNG GTCAAACACG TCAATTAC ACTGCGTCAA CCACCTGCCC          150
GCGAGCCATT CACACGGTAC TTATGAGAGC GACAGGTAGN CCCTTGNCAG        200
TCCCGTCAGT CTTGCCCCAA TAGAAGCCAT CACAGACACT GTCCATCACA        250
GNCCATCTAA ATTACANCAT NACATTATTC ACACCGAGAC GANCNANNNG        300
GCTCGTNGTG ATGATCGAAN TTTGNGATCG CNACTGCGGT GANCAGTTGC        350
AGATCGAACG GNTGAGGACG TCGTNGTAGA CAGGAGTNTC GNCAGNGCAA        400
ANCTTACTGN TNGGCANCGG CCGANTGANG CCGANAGCCA NAGACCGACG        450
TCTCGANTCA ATTCAAACAA AGACGTCCGG TAGCAGGGTC CGTAAATAGG        500
GCTGCGTTAA AACNCNTGNC G     SEQ ID NO. 10                     521
```

FIG. 1A

Plasmid 5:

```
GAGCTCCATC TGTGTGACGT TAATCTCCAA ACACCCTTCA AAGAAATGCA      50
CGAACAGTTA AGTTACCTGA TTACAGGACA CACCTCAACC ANCTCCATGT     100
CCTTTTCCGA CGAGCTGCTT CAACTACGCT CACAGTTCAC GTACGCTACT     150
CAGGTAAAGG AAGACACCGA AAGCAAAATC CATGACCTGA TGCTCAACAT     200
CGAAACCGNC ATCCAGGAAC CTACCACCCG CAGCTCCAAT ATCGNCATGG     250
NCATGGTCCA AGAACAGCTA AANGAACTTC AACAGCTCGG AGGNGCCANC     300
ATCCCTGAAA TAGCTACCCG TCTGGAAAAG GTACACAAGG TGTTGAATTC     350
CCTCCAACAN GAAGNACAGG GGGGCAGAGT CTTCGTCAAC GGGCTAAATT     400
ATGACACTTA CCAANCGATC AANCACTCAN NAGACANGCG GGCTTTCAGA     450
CTGNTGGGGA GGNGGCAGCT CACGAATTTC ATCCAGAANT CNGGTTTTTT     500
CAAACCTCTG GCCT        SEQ ID NO. 11                       514
```

Plasmid 6:

```
NGNTTGACAC TNTTAAGCTC GATGCCNACA TAAGCTGACG GNGACAAACC      50
AGGAGCGGGT ACAGACACCG AGGACGATTT ACGCGCGCGC GATGCACAAG     100
CTCTTGGGCT ACCGGCCAAC GCCGGCTGCA ATGCCCGTCN GAGCGACCTG     150
GGTCAGCTGA GTCGTGCTCT ACGTTGCGAT TGGCGATACT GGCGACTCAC     200
TACTGCCCCG GAAGAATACG AAGACCCCGG TGAAGACGAT TCTTATAGCG     250
AGTTACCATA CCGCACGTNG GNTCCCANCG ANTATNACNC TCAGTGNNAT     300
CCANAGATCG TATTCGGNNC AANCAACC GTCGCTNGCC GACTGTNTCA       350
TCACCGAGCC AGNGTCGGTN GACCCCTNCA CGCCCCCCCC CNCNCCCCCT     400
TTTAGCCNNC CCTCCCCCCG NNCNCNTGTC CACCCCCCCC CTANCCAAGN     450
NCCCCCCCGC CNNCCCTNCN CCNTNCCCNT NNTTNAGNTT CTTTTCAAGT     500
CTTTCATATT TCTNNATTNN CNCCTTTTCA TTTCGATGNA GGAANCTNCG     550
TNNNGNTTTG NNNTTTCTTC CNGCCTANGT TGTTTNANNT TTTTNTTNNN     600
CNNTTNNNTA NAATCCNGAG NNNNTTNCTC NCTTTANTNT CGTATTTNTG     650
AAANTGTTTT TCACCCCCCC A     SEQ ID NO. 12                  671
```

Plasmid: 7

```
GAGCTCTGCC GGGCGTTTGG AGGTGAACAG TTTGACCGGC TGCTCCGTGA      50
CTGATGGCCG CAGCGGCGGC CGACGGGTTA GGATATTGAC GACCTAACAG     100
TTCAGTTATG TGAGGAGGAT NAGTTGTGAG CGGTGAAATC ATAGTACACA     150
GGTACAGGCG AGGGATATCG CCGNAGCCGT ATTTCCAGAA CTCGTCAGCA     200
TCGGTGGNCA CGAGATGCAG AGTTAGTCGA GGAAAGTCGA GAAGAAAAC      250
ACNGAAGTGG GGTCCNAGAG CGANGTNCAG NNCTNCATNN TGACAGATAG     300
TTGNTTGANA NNCANNGCCA GNAGTNGTTT CCTTNCACNA TNCANGNCAA     350
TNTAANANCC NCCCANTNCG TCNTTTTGNT NNACANTTNN CCGNANTTCC     400
AANNTNNNCC CACCNNTTNN NCNTTTNCNT NNCCNNNNNT TNNTCNTTTC     450
AATATNACCC NNCCNNNNCN TCTATTCANN NNTNTNNNCN CCTCTCCCNT     500
CNNAACNNTT TNTNNTNNNTN NNTNNTNCNC TTCNNACNNC NTCCCTCCCC     550
ATCCNTCNAN CNNNNTNCNC NTTTNNCNNN NNNTTTTTTT TTTANTNNTC     600
CCATTNNTCN TCNTTA   SEQ ID NO. 13                          616
```

*FIG. 1B*

Plasmid: 8

```
GAGCTCTACT AGACGCGGAG AGACGCGTTC GCGACGGAAA AATTCCGGTA    50
CCCTTTGTGG ATCGCGATAG CCTGTTGGCC AACGTTATTC CCGTCGCCCC   100
CACTCCCAAT CCGGAAANTN NAGGAAGACC GGAGAAGAAA GCACTGACAC   150
GACAGTGTTC GNTCCCTACC CCCCACCCTA AGAAGTTCGG AGTNCAGCCT   200
GATTCCGATA GCGACAGNGA TACGATTATC GATTCAACTA TGGAAGGNGC   250
GGNATCTCTG TAGATTTTTT TTTTGNTGAA TTGNGCAACC CGCANTNGCT   300
TGGTGTNACT GTAGACAAGN CTNCTNTNAA TCANTAGTNT TNNTTTNGTA   350
ATAAAACNGN TTNGTTTNNT TTAATCCACN NAGTNGCNNT GTNTTAATCT   400
TNNTTGTGGG NTGATNAGNN CCNNCCCNCN NCTTTNACTA ANTNNTTNTA   450
ANTTNGNNNN TNNACNNNNT NTNNTNTNTN TNTTCCCNNT NTNTNTCCCC   500
NCTTTNNNNT TNNNNTTNNN CNTNNTTNTT NCNNNCCNTC TNTNTNTNNN   550
CNTTTNCNTT ATCTNNTCTC NCNTATTNTN NNCCCCTCNC NTCNCNNTTN   600
T    SEQ ID NO. 14                                      601
```

Plasmid: 9

```
GAGCTCCTAC CCTGTGCCCT TATACCATTC TAGGCACTTT ATTTTTTACA    50
TGGCTTGCCT CTGTTAAATG TCACCGTAAC TCCCAGATAA CCTCTTCTGA   100
TAGCTGGGAA AACCAAAGCA CAGATTGGTT TATAAACTTG CTCACACAGC   150
TAGCATCAGA GAGACCTGGG ATGTCTCATC ATTTCTGTTC TCGTATCAAA   200
GAGGGCCCTT GTGAGCCTCT CAGTTGGCCG ATCCTAACAC TGGTCAATTG   250
GAATCTACTC CCCAATGTTC CAAGGAATGG ATGTCATGAA CCATGGNAGG   300
TGGNATGGNT GCTGGAATCC AGNNNNGGTC CAGGTGANGN CTCAAGCCAT   350
ATTGNAGGTT GGCCTCAAGA NTTTGGCCTC CCCATGGGT TATGATGNNG    400
GGGGTTNCAT NTTTCACCAA ATTNGNAANT TTNGGNCAAN TCTTTCTTTT   450
ANNNAAAANT NTTGGNCTCA CCNGGNAANA AANANNAAAG GGGGGAANNN   500
TNNNNNNTNN GGNTTTNGNN NNNNTTCCCN NTNCTNTTTT TANNNNGNNN   550
NNNNNTGGGG NNNANNNNNT NNCCCCNNNN TCNNNNNAAA    SEQ ID    590
NO. 15
```

Plasmid: 10

```
GAGCTCCTCG GTGGGACAGA GCGTANAGGC TGGAGTGCTC GGGGCGCTTC    50
GTGACATTTT ATATCAATAC GCTGACAACG ATGAGTATGG GCTATACGTG   100
GACTGGTACG TCACGGTTGG AATCATCCCT CTGATGGATG TCAAGTCTAA   150
ACCCGCCGAC ATCACGCAGC GCGCAGGCTT CGTCCGAGCC GCAATCCACA   200
GAGCCACAGA GACTCACCCG CTAGCTCAAG ATTTACTGAC CGNTAACCTT   250
CCCGCTTCTG CAGNAAGTGN GTAACGCATC TTNTNCGCGG GTCCCCAATC   300
GTTANCTCCC CCGNAGNTNN CGGATCTTCA AACGAATCCC CTCCGGNAAA   350
GATTGNNGNG CANCCTANNT GAAAAGCATA CCCGCNGCTA TNTTCTTACA   400
GANCCNNTTN GCCTNNNAAC GNNAACANNT TNTTCTTCAN CNNCCCCATC   450
GNCCCACCTT CAGNAAGANA TTTGGCGTT NACGAATNCC TNTTTNCCTC    500
ACNAGNAGTT CTTCCNATTN CNTNNNAANT NTTCANTCAA GCCCNCACCN   550
CNCCCCNTNN TTTACTTAAA AATCNCCNNT CTGNAACCAC NCCCNGAGCN   600
ATTCNANNNN NCCCANAACT NTTTTTNTCT TNTCCNN   SEQ ID NO.    637
16
```

FIG. 1C

Plasmid: 11

```
GAGCTCCTCG GTGNGACAGA GCGTACAGAC TGNAGTGTTC GGCGNGTTNC         50
GNGACANTTT CTATCAATTN GCTGACAANG ATGACTANNG NNNTATTCNT        100
TTNCNTGNNA CNTTATTTTT TNANNTNAAC CCCACTTATN NTTCNCATAT        150
NCTCTNACNN NNCTNANATC AACCTNATNA ATCTTCCNAT ANTNCTNNNT        200
CTTACTACCA TTTTNCTNCT NGATTNTCCN ATTTNCNTTC CACTTNTNTT        250
ANNNTCCANN TTTNCTACTN CNANTNNCNT TTATNCNCNC TCCATCTCTN        300
TTTCCCTCAT NNTCNACTTT TNATANTNCN CTTNACNNCT CNNACNCTAT        350
NNTTTNNACC TTCCANCTAN NCAATCNTNT ATNNCTTTNT ATTAATTNCC        400
TAANCNCNCC TTNNCCNNTN NANTCAAAAT TNCACTATTN NATTTATNNA        450
CNCNTNTTNN TTNCTANTNN CACTCATCNC TCTAAATTNN CNNCTANNAN        500
TTATNTCAAA TNTANTCTTT NTNTATTTAA NATNATCTCA CCNATTTCTC        550
TTATACNCNA TNTNNNANNN CATTTNTANT TAAAANTANA NTATTTTNTT        600
TNTTNTNNTN NNTTNTCNCT CNCATCTNAC ANNNTTTANA NTNCAANNTT        650
TTTNNCCTTC TATCANATN     SEQ ID NO. 17                        669
```

Plasmid: 12

```
GNNTTTGACA AAGCCCGTNG TCACAAACGT CNCGGAGACN AGTCGGCGCT         50
CGGGACTCAC ATCCACCGAC TCATTGCGCT CTTGGATCAC GACAACCATC        100
GCGAACTGTG CAATGTGCTG GTCGGGCTGC TACACCAAAC ACCCCACATG        150
TGGGNCCGNT CCATCCGTCT TATCGGTCGA TTAAGAAACT ATCTACAACA        200
GAAGTTTCTC AATATCTTGG TGGATAGNGG NCTCCAGATC GATAGTCTTT        250
TTGAGGGTTG GTTACCACAG CGAAGCGTAC CGCTTGCTGT TCCAGATCGA        300
AAAAACGAAC TCCACGCCTA GCTCTCTAGC CTGTGCAAGC ACCGNNTTAC        350
CTGTCGGTGA AAACGAAACT GAAGGNACAC CTNGNNCCGC CCNNGTNTTT        400
ANTGAAATAA TAATATGGGT NCTCAANGAA TAAGANGGGG CTTTTNTTTC        450
GNNNNNGGTN NGACAANTNT NANTCTTCCN CCCNATNCAA TNCCTNNCTG        500
GCCCGTNNNN TTCGNCTCCN NTTCNTTTNT CTTNGGTCCT GTNNTTTNCT        550
CATNNNCNNN ANNTCCTCCT NGNNCTNCTC CCCTATCNTC NNNCTNNTTT        600
TNNNTNNCTC NCCNNNNNNT CNTNTCNCTN TCNTCNTCTN TNNCCNNNNT        650
NTTCNNTCTT NCCCTTCTCT TNNTNNNTTN NTTCNNCTCT NNTNTNTCNT        700
TTNTNCNTTN TCTCC      SEQ ID NO. 18                           715
```

Plasmid: 13

```
TTTTTTNNNN NNTTTTTTTN CGCACCNNCG CAATTAACCC TCACTAAAGG         50
GAACAAAAGC TGGAGCTCCA CAGCTTTCCC TTGGCATGGA AAGGGCCAGA        100
AGAGCCAGTG GAAGGGACCT GCCATGCTAA GGGGCGAGGT GACCCCATGA        150
TGAAGGCCAC AGAGTGTTTA ACTTAGTAAG GGTCAGGTGG AGGGTGCATC        200
TGAAGCTCAG AAGGCCGAGC AGAGCAGTGA GGAGCTGGGA TGGGGCAAGT        250
CGGCAAGGGA AGAAGACAAA TTTCAGGTTC ATCTCCATAC TCCGGGAGAG        300
AAAAGCCAGA AGTAGNCCAT GGACCAGGCG TCTCTGNCTC TACCTCCTGC        350
ACCTTCTCCA GTTCCAGNCA CTCCCGNTCC CCCTTCACTG NAGNCACAAC        400
CAGACTCCAG NCCTCCAGNN NTGNCTNGNT GCCTNNGGNC CACAGNNCTC        450
CCNNACCTCC CNTCTCTCCT CCNNNNTCAN ANTCANNTTC CNNNATCTTC        500
CTTNNNNTTN GNNCANNNNC CNNCTCTCNT CATNCTCTNT NNNNNTTNNN        550
NNNTNTTCAN NNNNCTNNGN NNNNNNNNTT CNNNNTTNNN TNNNNNGNAN        600
NNCNTNNNNA CCNNTTCCNN NNNNNNNNNN NNNNNNTCNN NNNNGNANNN        650
NNNNTNNNNN NNNNNTNNNN TNNNNNNNNN NNNNCCCNN NNNNNNNNNN        700
NNNNNNNNNN NCNNNNNNNN TNNNNNNNNN NNNTNTT      SEQ ID NO.     737
19
```

FIG. 1D

Plasmid: 14

```
GGTTTNGNAA CTCTTGAAGC TCTCGNTCCC CTAGAAACAA GGCTCAGTAC      50
GTGGAAGGGG TGTGGCNTCA CGCCTACACA CCTGGGCTGC TCGACCATCA     100
TAACGTGTGT GATCTGGAGG GGNTTCTTTA CCTGTTGTGC TGCGGACCCC     150
GNAGTTTCTG CTCGCGGNAC ACGTGTTTCG GGCGGGAGAA GCACGGTTGA     200
CCATTCCCCG CCCTGCTCCC CAAGGATCTT TTACGAGCCC GNTCGCGATT     250
ATATGACGNA TGTGAACCTG GCTGAACTTC TACGTTTATG TGTGGNATCG     300
CGGCTATGAT CGCCCTTCGA CTTCGGATCC NACGCCAGGG GNTGATGACG     350
ACCGANCTNC NGNCNGNCTT TTAATAGANC CGCCCTCNCN TNCNCACCNN     400
TCTCAACAGG ANNTTGCTTA AAAGNCGTGA TCCNANCGNC NGCTTCTTNG     450
GCCGTCNCNA TANTTCNCTC TTCNACNTNC CTNNCTTNNT CCTNACANTC     500
TNNCTTCNTC CNTCNNGCCT CNNTGCACNN CNTATTTCTT CTNCATCTNT     550
TTANCCTCCC NTCNNANTTT NNNTTNNCNA TCACTCCANN CACNNCCNNN     600
TNTTANCCCC CANNTCCCCC CCCATTNTTN NCANCTNCTC CNCTGCCAAN     650
NNCCTNNTTT TTANCCCCNT CTNNCCATNT TTTNCTTNGC TTCNCNTANA     700
TCCANANTCC CCCTNNACCT TACANCTCTN TATCCTCTNA TCCCTCCNAC     750
TATACCCCTT NTTNTATCNT NTCCNCCCC      SEQ ID NO. 20         779
```

Plasmid: 15

```
GAGCTCACAA AACGGTGCTG GTTTGGTTTT TTACTTGGCC CACGGATACG      50
GGGGAGAGGT AGACAGGCCC GACTTCTTTG TTANTCTCCG GGTCGTCGGC     100
GTCCGCCACG CTGGTCAGCA GGTGTTGTTT ACTCTGCACC AATTCCGACA     150
GCGGTGTACT CGCCATCGCG CCCGTGCCCG ACCACATGTN AAAAAGCAAG     200
TACGTGAAGC GCTCGGGGGA CGGAGTGCTG TGTTCTGTAA ACATCTGTAG     250
AAGTTGCTTC GGNGCCTCTG GGATTTTCAC AACGATTGTC TGTTTGTGGT     300
GGCTAAATCG CCGGTGTTTG GTGTACGGTA CCGTCTCGTC ACCCATCACC     350
ATGGCTTTTG GACCACTGCC ANATGGCTCA GGGTTATGTT TTCGGTTCTT     400
CCACTGAATC TCCCAACTGC TTTTCGAAGC AGCGATTAAT ANAAAAATGN     450
AGATGGAAAT CAAACAACNT CAANGAAATN TTGTCGAAAA GAGNTNGTCC     500
ACGTGAAGGT CCCNANNNTT CTTGACGCAA AGTATGATTC AACTCGGNNA     550
TNGTNANTNG CAAACTTTAA GGCGCCCNCN NGGCCCATTA NATTANACNA     600
NAGAAACTTC NCCGNATGCN AANTTGTCTT ACTTGTCAAN AGTTTATNNG     650
GAGTTTGACG TTNNTCNAGG GNCAAGTTTT CT   SEQ ID NO. 21        682
```

Plasmid: 16

```
TGTTTTNCAN CTTCTCAAGG GACCCCCCCC CGAGGAAGAC GGTATCGATA      50
AGCTTGATAT CGAATGCCCT GCAGNCCGGG GGNATCCACT AGTTCTAGAG     100
CGGNCGCCAC CGNGGTGGAG CTCGAGACAG GTGNCGCGAT ATGCCNCGGC     150
CTGGCACCGC GAACACAGCG GCCCTGGCC GTGACACGTG AGCTTCAGGA      200
GTCGCGGGAT AGTGACGGAG CGCACCACCA CGGTGGAATC GCACGTCCGC     250
GCAGAGCACG GTAGAATGAT GTCAAACGTG ACGAGGTGGT CATAGACCGC     300
ACACGCGGTG TTCANCCCCA AGACTGNCTT CCAACCAAAC CGNAAACAAC     350
GTTGCCCACA NATCGTCTCA GAGACANCTT CGTAAACACG TTCTTTTAAT     400
GACACGCTGA CTTCCACAAA AGAGAACAGT GCANCAGTTC GGCGTTAGTA     450
TTGAAANTGA CACTCTTTTC TTGGCGGTCT CTATANTAGA ACATAGAGTT     500
AAGGGGGGAA TTCTGCTCGC AGNGNAGGTT CTCCTGGCCA AGTTCAAGCA     550
GGGGNCGAAT TTCGGANAAC ACGGNGACAG GATCTTGGTT TAGTGGNGTC     600
NACTCAGNGA AAAGCACAGG NGGTTTATAC GTTCTTTNTC CCGAGNCNCC     650
ATCTATATTT GGTGTCNGGC CCNTTTTTTT    SEQ ID NO. 22          680
```

*FIG. 1E*

Plasmid: 17

| | | | | | |
|---|---|---|---|---|---|
| GNNTNTGCAC | NTNNTTATAG | GTCTNANTCN | CGTTNAAAAC | ATTTGNGGGT | 50 |
| ACAGCGNTGC | CACCGNCCGA | TGGAGAACGT | GTTGTATGNC | CATNTTCTNC | 100 |
| GNACAGCCNG | GGAGATGATC | TGATGANACA | NGNNCCACTG | ANGAGTGGAG | 150 |
| GANGATNATA | ACGACTACCC | GNCNATTCCA | CAGGTGCGAC | AGGTTCCCCA | 200 |
| GTATCGATCG | TCCATCAGCN | TCGGCTGGNA | CCCACTGANG | GTGANCGCCC | 250 |
| NNATTCACAC | AGTTAAGATG | GCTGAGCAAN | GNNGAGGAAG | ATNACGTCTC | 300 |
| GCTGCACANN | ANCGCCGCAT | TGACCCGTCN | GAAGNNCGGC | ACCATATGGT | 350 |
| GCTNACCCTC | GNNCCCCAGT | CCTGTCGACG | GCTATTGANT | NNNTTNNTTN | 400 |
| AANNCCTTGG | CTTANTGTTC | NTTTGNNCAG | NTTCACGATN | TTCTNNGCCC | 450 |
| CNANTTTTTC | NGGATCCCCT | CNACATCTTA | NATGTTCGNN | TCGTTTTTAA | 500 |
| NAATCCTNCG | GNTTCCCGTT | CNTTTANTCC | ANTCNNTCNT | NCGNNTTNTC | 550 |
| ACNATGNCNN | ACTCNNGTNN | TNTCANTNTA | TTNTTTACAC | GNATCTTTAN | 600 |
| NCTTTTCNCN | CCCATTCCCC | NCNGNCNNCN | ANGTTNTTNT | CANNNNTCCC | 650 |
| NTCNNNCGTC | NNCNANCTCT | NCAANCANNA | GCNTCTTTNN | TTGCNCATNT | 700 |
| NGTCNTTGGA | ANCTNTNNCN | TTNNAAGNNN | ANNGTACNNC | CTCTTTNTTT | 750 |
| NANNTNACNC | CANANACANG | NNCATTCTTA | AATCNNCNTT | ACNCCCTTAC | 800 |
| TCCATATCTN | TATCTATANT | TT | SEQ ID NO. 23 | | 822 |

Plasmid: 18

| | | | | | |
|---|---|---|---|---|---|
| GAGCTCATAC | TCCGCTGCTG | AGATGGTGGC | CTGATAGAGT | CGTCTTATGG | 50 |
| CGGTGACGGG | TACGGGTAGG | TGTTCCACCG | AGGTGTGCCG | GGAGGTTGGG | 100 |
| CGTNTCTGCA | GATGGGTTAT | ACACANGTTA | CGANTTAAAC | ATTTGGAGTG | 150 |
| AACGTCTCCG | TCCTTTGGCG | CGCGANTCTT | GTAGGGCGGC | ATCGCGCAGC | 200 |
| ATATAGTTCG | CGATTCGCNA | TTCCTCGTTC | CCCGTCTATC | GTCCATTGGN | 250 |
| NGAGGGNACA | CAGANTATAG | TCTCCNAGGA | CACAAAAGCG | TCTAGGTGCC | 300 |
| CTCAACGGCT | CGCAGGNAAA | TCAANAGAGC | CCANNTTNTT | TNCTTCGANG | 350 |
| CAAAGGTTTC | GNCACCCCG | TCCGTTTATT | TTGTCNCCGA | NAANATGGCT | 400 |
| TCCGCCNGAN | TTTGNTTTGT | TAGTCANTTC | CCGNNGNNGA | GGNGNATTTT | 450 |
| NTNANNTANC | NTTCANATTA | NNTTAANCNT | CNCCAAGCNT | TCTCTTACCT | 500 |
| NTTACNNCNA | ATNCAACCA | AATCATCNGN | TTCCGCTGNT | TAAACTGAAT | 550 |
| NTNACATCNT | TCTCCACTAA | ANCCNNTCNT | NCANACNCNT | NNCCTCCAAT | 600 |
| TCTCCTCANA | ATACCNAATA | NCNCNNCCAT | CCNNCTNANT | TNTGNNTCAC | 650 |
| TCNTT | SEQ ID NO. 24 | | | | 655 |

Plasmid: 19

| | | | | | |
|---|---|---|---|---|---|
| NGTCTTTGNA | CCTTNTCAAA | GATCGAGGCN | CCCCGAAATC | GTTGTGTCGG | 50 |
| GGCTGCGCCT | TGGTGNCCNC | AGACNGNGTG | TCACGGCAGN | AGTCATGTCG | 100 |
| TCTAGCTCGA | GNAACACGGG | TACCAACGTT | ANGAAGGATG | AGGAGNAGCG | 150 |
| GCGCCACGTG | TGTGTGAATG | TATTGGATCT | GCCCCAGGAG | TCCATGGAAC | 200 |
| ACCCCGNGAC | CGGNACCATG | TTGTCCAAGT | ACGTCCGGAT | GTCCAGCTTC | 250 |
| TTTACAGACA | AGTTTGCCTT | TAAGCTGGAC | TTACTGCGCA | TGTTGGCGGT | 300 |
| AGCCAGAACC | CGTCGCTAGC | GGGCGTCTCC | TCGCTACAGT | AGATAGAGGA | 350 |
| AGCGCAGACG | GTTAATNGTT | TCGGTAACC | GATTTAGCCA | TCGATTGAAG | 400 |
| ATCTACGGCG | CACGGATCGT | NGGATTTGAA | TNGCGTTTAC | AACATTTGA | 450 |
| GTTTAGAGTC | NTCAATTGGN | GGGATTTGGN | AAACTNCGAG | CTGGCGGNCN | 500 |
| NAGGGGAGAN | CGGCAATAAA | AACTTCCTCT | ACGANCGATA | GCTTNACAGN | 550 |
| TTNCTNGCGG | AAANAGGTTC | GACCANCNTC | ACACGGAGGG | AGCTTTTNNT | 600 |
| CCTTCCTCTN | NNAAAGCCTT | NAGNCCTCNA | TCNCCNNTA | NNTCGTATTT | 650 |
| CCANCACGAT | ATCCGNNCC | CCTNNACTCT | CNCTAATCCN | CCCCTNNNC | 699 |
| SEQ ID NO. 25 | | | | | |

*FIG. 1F*

Plasmid: 20

```
GAGCTCACCA AACGTTGCGG AGACAGGTGG GCGCTCGGGA CTCACATCCA       50
CCGACTCATT GCGCTCTTGG ATCACGACAA CCATCGCGAA CTGTGCAATG      100
TGCTGGTCGG NCTGCTACAC CAAACACCCC ACATGTGGGC CCGTTCCATC      150
CGTCTTATCG GCCGATTAAG AAACTATCTA CAACAGAAGT TTCTCAATAT      200
CTTGGTGGAT AGCGGANTCC AGATCGATAG TCTTTGTGAG GGTTGTTACC      250
ACAGCGAAGC GTACCGNTTG NTGGTCCAGA TCGAAAAAAA CGAACTCCAC      300
GCCTAGNTCT CTAGCCTGTG CAAGNACCGN NTTCACCTGT CGGTGAAAAC      350
GAAANTGNAN GGGACACCTG TNCCGNCCGT NTTTTTAATN AAATAATAAA      400
ATTGGTTCTC ATNAATTTAN ACGGNCTTAA NTNTCCGNNT TNGGGAAGGN      450
AAANTTTTNN TTNTCCCCCC AAACATTCCC CCCCTTGGNC CNNNNTNNNA      500
NCTNNACTTN CNNNCGGCCN TNTCCTNANN AAANCNNATT TTTTCNNNTN      550
CCC      SEQ ID NO. 26                                     553
```

Plasmid: 21

```
GAGCTCGAAT GAGATCACGA TGATCCGTGG NGTTCACCAC GACAGGCCAT       50
TCCGAGTAAA CCATGGAATC CGATACCCCG TAGGCCGAGT CCAGAAACAC      100
CGAGGCGAAA CTGAACCCCA GCTCGCAGAT CACGGNGTCG CTGAGCATTA      150
AGTGGTCTTT TTCCAGANTG GTCAGCTTCT GGGTCGTGTA CCCGAAGTAC      200
TTCTTGTGCG GAGNCAGCTT GACGGACTGC TGGNTGTCGN TCACGAACTG      250
NTTCAGGGNC GNTTCGATCA AGCANCTTGG GTCTCTGAGT AAGGGNAGGG      300
GTTTGGCACC ACGAANGTTN TTNAACNATA ATAGAANAGG GTTTTCCGTT      350
CANCCCNAAG GNAAGGTCNA ATCCCCCGNN GATTCCANGA ANCGANNTTG      400
GGTTTTTCCA GAGAAAAGTT NANCCCNATT CCNAAATCGG CCTNNAAANA      450
ACAAAGAGGT GGGNNGGGTN AAANNNNNNA NGNNNACCNN TCGANTTCTC      500
CAANNNNNTT TGNNCCCCCC CNCCNNAGAA GGGTTNANTT NCCCNATTAT      550
TAATTTTNTT      SEQ ID NO. 27                              560
```

Plasmid: 22

```
NTNNTNNNNN NNNNNGTTTT NNAACTCTTA AGCTCTACTA CCCGCGGAGA       50
GACGNGTTCG CGACGGAAAA ATTCCGGTCC CCTTTGTGGA TCGCGATAGC      100
CTGTTGGCCA ACGTTATTCC CGTCGCCCCC ACTCCAATC CGGAAACTGA       150
AGGANGACCG GAGAAGAAAG CACTGACACG ACAGTGTTCG CTCCCTACCC      200
CCCACCCTAA GAAGCTCGGA GTCCAGCCTG ATTCCNATAG CGACAGCGAT      250
ACGATTATCG ATTAACTAT GGAAGGCGCG GGATCTCTGT AGATTTGTTT       300
TTTGNTGAAT TGTGCAACCC GCATTGCTTG GTGTCACTGT AGACACGCCT      350
TCTGTCAATC ACTAGTGTGC TTTTGGTAAT AAACGGNTNT GGTTGGTATT      400
AGCCACGCAG NNNGTGTGTC TCATCTTCTT GGCGGGTGAT GGAGNGCCTA      450
CCCGCCTGTG TNAAGGTTAA TGGGNTTCAC AGTTNGGGAG TGTGANTTTG      500
AGATTTTGTT NAACCCNAAT TGTTTATTGG NTTAANTCAA GNGTCCTTTN      550
TTNTTGGNNT NTTNTANGNT CTTTNATTNT TNAATTCCNT TNTNTTTTTT      600
ACGGTNNGGC GGTTGGNNTC NTNANTTNNA ANNCCNNNGN AAAANTNANN      650
ANAAANNNNN NNNNTTNTNN ACTTTNNTTC ANCTGNANAA TTTA      SEQ  694
ID NO. 28
```

FIG. 1G

Plasmid: 23

```
TGTTNNNNTG TCCNTAAAAC CCTTGAAGCT CCGGGTNCCC CGGATTTTAT          50
TGACGAGATC GGAAGTTCTA GAAGNNTCCA CCACGCCCCC AATTTCCTGA         100
ACCACGCCCA TTTCGGATTG CAAATCGGAG AGCGGGGCC GCTGGGTAGA          150
AAACGGGGGA TGGGGAACCC GCAATGCAAC CCTATGGGAG CAGGCCGTCG         200
AGNACCGTGG GGGGAGGGGC GGTNTANCNA ACCCTGCCAT GCACGCTGGT         250
GCGAGGTGGG GGTTGGCCAC TGNAAATGAN TCTGGGGTCT CCTGAATAGG         300
GGGATNNGGC TGNAGCCNCC AACCCNNANT NATTGGTGCA TCATGGNGGA         350
TTNGNNACAC AAACCACCTT TNTTTTTTTT TTNTTNATTG GANGTTTCTN         400
NCAACCANAT NCCTNAACTT CTTTNTTTGC CCCAGNTTNC TCNNGGNCCC         450
NNNTNTNTCC NCCNTCNTTC CTNNANTCCN TNACCTGNGT NTCTTNNNNT         500
TAAAANCCNN TATCCCCNTC NATCANNNGT GGANTGGGNG NNTNNNNCTT         550
NNGNTNNATN NNCTCNTCCC NNNNTTTNNT NTTTTCCTTN NANTNATNCN         600
NTNNNNNTTT NNTNTTTTTN TTTNNTNCCN CTTNNNNNCT CTNNCNTTTN         650
TCNANTTCAN ANCTTNTCNN NNNTNCNTTN TNNTCTTTNN TNNNTNNNNT         700
TTCT     SEQ ID NO. 29                                         704
```

Plasmid: 24

```
TTTTTTTTTG CNTTCTNAAA GCAACNACAC NCAAGGNAAC ANAAGATGGA          50
GNTCCAGCGG NGNATCGGCT CGCGCGACCN GTCGGAAGGT TCGGAAGCCN         100
GGCGGNGTTC AGGGAAACCG ANTCNTTGGA NNCCNANNTN AGNCNCANNN         150
NTTNTTNNAT NTANGNNGGA GACANNAGNN CNTCCCATNT NGNANCATAT         200
NNTTANNTNN NTCCANACNT ACCCCANNAA ANCGGTCNTT TTTTTTTTTT         250
TACANANNNT ACTTAATTTA AAAANCCTCA ATANNNAANC NANNTNNTCC         300
CANGNACCAN NNCGCNNTAT NNCAANCTA TCNNTTNCCN NGNNNNGCTA          350
TNANCGACAT CATNCATNAA NTATNNAANC NAAANNCATN ATAGAGTTTT         400
NNTNANATTN CNANNNCTAC AGNNANTCAN TCNGNNNTTA ANCANAGNGG         450
NGGATATCTC CNCAANCANN NTANNAANTN GACNCCTANN TATANNTTNN         500
NNTNNTNTAA TNCANNCTAN CANATCNNNN CNCTCTACAT TTNTACNNNA         550
ANACANATAN NCAAANNNTN TNNATNTATN NNTCCNCCNA NNTNATNANT         600
AATTGTNANT ATNTACNAGT GCTNTNCANA ANGNTNANGC NATCNNACTC         650
NCTACTTNAC TTAATNNAAN CACNNNANTT NNTTCACTAT NTTNNCNATA         700
ANTATATATA NTCNNGNACN NNTANCN     SEQ ID NO. 30                727
```

Plasmid: 25

```
GAGCTCGGAC CTGGTCTTCG ATAGCAGGGA ACTCATTATC AGGAACATGA          50
GGGATCATTG ACAACACCTC ATCCTCCAAA ACGTCCCCAT TGGCCGNCAC         100
CTCATCCACA GCAGTGGTAC CAGTCGCGTC CAAAATTGAG GTGCTTTGAT         150
CGCAATCCAT GTCCACCAAA CCCATAACTT TCTGAACTTC ACACAGNGCC         200
ACTTGGTCCG TAGAAAACTT ATTCAGCAAC ANCCTCCAGA GTGTCGTCCT         250
CAGACATGGT AATTTCGCCC ACCACCAGTT TTCAAGATCA TATNGTTCCA         300
GAGNCTNCAA TANTCCCGTT GCGCAATTCT GATTCCTCCA CCTCGGAGGT         350
GGGGNGCGCT ANTCGGCTGG CATTTATTCC TCAAAGAAGT NCNTGCAGNA         400
GNNGAAATTT NATCTTGCAC TNNCCNATCN AGGNGGGTTC AAGCTTGGAG         450
CAGNTTCTTC GNNANTTCNT TGTTCCTACC GAAATTTCTT AANAANCNTC         500
GNGCNCCNTC CCAACNTACT TATNTTATCN TCGCNGTNNA NC                 542
SEQ ID NO. 31
```

FIG. 1H

Plasmid: 26

```
GAGCTCTGCC GGGGGTGTGG AGGTGGACNG TTTGACCGGC TGCTCCGTGA      50
CTGATGGCCG CAGCGGCGGC CGACGGGTTA GGATNTTGAC GACCTAACAG     100
TTCAGTTATG TGAGGAGGAT GAGTGGTGAG CGGTGAAATC ATAGTNCACA     150
GGTACAGGCG AGGGATATCG CCGCAGCCGT NTTTCCAGAA CTCGTCAGCA     200
TCGGTGGCCA CGAGATGCAG AGTTAGTCGA GGAAAGTCGA GAAGATNNTT     250
TATTNTTNTN GGGTCCCNNG AGCGAAGGTA CAGACCTNCA TGGCGANCAG     300
ATAGTNGGNT TNANNAGCCA NNGCCAGAAG TNGTTTCCGN NNAATGNTAC     350
AAGGCACCTT AACAAGACCC GNCGCTTTTT TNGGGNNAAA GTNTGGCGNA     400
AGCNCAANNN NCNNACCNAC TNTCNNNGNA TTTNAAANAC NNNNGCTNTC     450
CNTCTNACTC ANTCTNAACC NATCCCNNCN GGCTANNNNN ACTNNNTCNT     500
CCCNNCCCTT CTNTNANACC CNNTGGCNN  CCCTCCANAA NNNCNTTCTC     550
NCTTAAANTN CCG        SEQ ID NO. 32                        563
```

Plasmid: 27

```
NNTNTAGGGN GTTTTNTNGN NCGGGATNNN NTAAGCCCNN NTCTNTTTAG      50
GNATNNNGGC CAGTCGTCAC CNCNNTNCNN GCNAAGNANT AATGGGGGNG     100
NNGGGGGGGC TANGGNATNT NGAACNTCAN NNGTGNACCN CCANTCCNAG     150
TCAGCGANNG CNAGTGANGA GNCCACACAA NANCGNNAGT ANANCGACAT     200
CNATGNGTCT ANCCTNACAN GCNNCTTTTA TCNNATCCAN NNGTANATNN     250
NCAGAAGAGN TNTCAANCAT NTNCGCTATA NTNNCNGNAC ATAATTCGAA     300
NNANNTCTCT TCGNANNNNT CGCTNNNNNG GCNTNTNGTN GAACTATAGN     350
CNNCNANNTN CCTCNCNNAA CTNGCTNNAA TNANTTTTTT NNTTTTATTN     400
CNNNCTCCGA CTCGANCNTC CCCTNNGCNN TTCNNNNNTN NTNTNATTTT     450
NNNNCCACCC NCTNGCCATN TCCNACANCN NCTCNTNNCN NGCNCCNNNT     500
TTTNTCANAN CNNNCTTNTN NANAANTTCT CTCCATTNTN CNNCNCCCNT     550
TCNANTNTTC CTATATCCNC NNANANCAAT AACTNNTTTN TNANTTCACC     600
NTACTTTNNT NGTATACTTA AACNNTCCCA CTCCNTCTCC ANTTTTNTNA     650
ANTCCNNCNC CCNAATCNNC CACCCNNTNC NTTTTTNNCT TTTATA        696
SEQ ID NO. 33
```

Plasmid: 28

```
GTTTGCAACT CTGAAGCTCA TAATCCCTCC AAATCGGTAG CGTGGCAGTA      50
GTAACGATGT CGCCTATGGT AGCATTCAGA AAGTAGACGT CGCTGGCAAA     100
GGTANGTTTT CGCCTTTTGA TTAGGACCAG TAATNTCAGT ATGTTTGCTA     150
TGAGTCCGAC GCATATGGNG ATGCTATAGA AACCGACGCT GACATCGCGA     200
GATGCGTCGT CGATCTTAAA CACTTGCAGA AGGTTACAGG AGGAGTTGTT     250
CANGTTTGTA AAAAGTCTGT TCGCAAATCG AACAATCTCG ATTTGCAATG     300
TCGGGGTTNG TGACCGGNCT CAAACATATA TCGGNTGGTN GTGTCGTTGC     350
GCTATCAACG CGCAATAATT TAGAACGCGG ATTCATATTC CCTGGGCGGA     400
AGCTCTGGGG GATCGTCCNT TCANGCTATT NGGGAGACAT NAGCTTTTAC     450
AACGTTCCCC AGCTTATGGN ATGGTTGGGC ACTCCCATTA AACANTTCGG     500
AGGTACCCNC CTATTGATNT TACGACTTNA CACATNTTCN AACTTNATAG     550
GACTTAAGGA CGGGTCTTTN NNAACANAGA NGGTTTTACC CNCCCCCCCA     600
AAAAGTTTG  GTCGTTTCCA ANTTTTCCNA ACTTTTCNGN CGCGATCATC     650
NCCCCNNCNC TCGAAGNTTT ACGTTGGCAG CCCNNGAAAA NATGTAAAGC     700
CCNTTATNCN CCACTNCCCC CTCCNCTTNN NNCTNCCCNN CT             742
SEQ ID NO. 34
```

FIG. 1I

Plasmid: 29

```
NNGAGCTCTG CCGGGGGTGT GGAGGTGGAC NGTTTGACCG GCTGCTCCGT      50
GACTGATGGC CGCAGCGGCG GCCGACGGGT TAGGATNTTG ACGACCTAAC     100
AGTTCAGTTA TGTGAGGAGG ATGAGTGGTG AGCGGTGAAA TCATAGTNCA     150
CAGGTACAGG CGAGGGATAT CGCCGCAGCC GTNTTTCCAG AACTCGTCAG     200
CATCGGTGGC CACGAGATGC AGAGTTAGTC GAGGAAAGTC GAGAAGATNN     250
TTTATTNTTN TNGGGTCCCN NGAGCGAAGG TACAGACCTN CATGGCGANC     300
AGATAGTNGG NTTNANNAGC CANNGCCAGA AGTNGTTTCC GNNNAATGNT     350
ACAAGGCACC TTAACAAGAC CCGNCGCTTT TTTNGGGNNA AAGTNTGGCG     400
NAAGCNCAAN NNNCNNACCN ACTNTCNNNG NATTTNAAAN ACNNNNGCTN     450
TCCNTCTNAC TCANTCTNAA CCNATCCCNN CNGGCTANNN NNACTNNNTC     500
NTCCCNNCCC TTCTNTNANA CCCNNTNGGC NNCCCTCCAN AANNNCNTTC     550
TCNCTTAAAN TNCCGNNNTA TNNNNTGTCT TTATTCNCTT CAAGGCCCCC     600
CTCCCAGGTA GAGGTTTCGA TAAGCTTGAT ATCGAATGCC CNCAGCCCGG     650
GGGATCCACT AGTTCTAGAG CGGCCGCCAC CGNGGTGGAG CTCCGTTTTC     700
GCAGCGAGTG CGGCAGATGG TAGCGATTCA ACGTTCAGAT CTGGATGAAT     750
TCACGTACCC CTGTCAAGCT CTTAAAAGGA AAGGGATCGC TGTACGTCAC     800
CAACCGTGAC TGATGCACCA AAGCTACCAG GACGCGTTCC GTAGGTCTTT     850
CTCGCGTCGA TTGACTTCGT CCGTTACGAG GCAGTGGAGA CGAGGGCCAG     900
GGTCTTCCTG ATGGGTCGCT GNCTCGNGCT CCGNTGCCTC GACACGAACG     950
AACTTGAGAC TCGANGGACA TAGGTCTTTN TNGGANCCG TATTCGTAAG    1000
GGGNGGAAGG AACCAGNGTA TTGGNNATCT TAGNTTCTTC CCAGGCTTCC    1050
CCTGATACGG GTCCGGAAGG CGNTCTTTTT AAANAAGAGC CAGTCGGNGG    1100
NNTTTTCTTT AAAAAGTTN TGGNGGGGNT CTTCCCNNNN NNNNGGGAGC    1150
AANNNNNTTC GNNGNGGGNN ANCCATTTNN NANNNCNNNC CNNNNNGGNN    1200
NTTTTAATNN NTTNCNACCN NNTNNNNNNN TAAGTNNGGC NCNNGGNTT    1249
SEQ ID NO. 35
```

Plasmid: 30

```
GAGCTCCGTT TTCGCAGCGA GTGCGGCAGA TGGTAGCGAT TCAACGTTCA      50
GATCTGGATG AATTCACGTA CCCCTGTCAA GCTCTTAAAA GGAAAGGGAT    100
CGCTGTACGT CACCAACCGT GACTGATGCA CCAAAGCTAC CAGGACGCGT    150
TCCGTAGGTC TTTCTCGCGT CGATTGACTT CGTCCGTTAC GAGGCAGTGG    200
AGACGAGGGC CAGGGTCTTC CTGATGGGTC GCTGNCTCGN GCTCCGNTGC    250
CTCGACACGA ACGAACTTGA GACTCGANGG ACATAGGTCT TTNTNNGGAN    300
CCGTATTCGT AAGGGGNGGA AGGAACCAGN GTATTGGNNA TCTTAGNTTC    350
TTCCCAGGCT TCCCCTGATA CGGGTCCGGA AGGCGNTCTT TTTAAANAAG    400
AGCCAGTCGG NGGNNTTTTC TTTAAAAAAG TTNTGGNGGG GNTCTTCCCN    450
NNNNNNGGG AGCAANNNNN TTCGNNGNGG GNNANCCATT TNNNANNNCN    500
NNCCNNNNNG GNNNTTTTAA TNNNTTNCNA CCNNNTNNNN NNNTAAGTNN    550
GGCNCNNGGN TT        SEQ ID NO. 36                       562
```

Plasmid: 31

```
GAGCTCCGTT TTCGCAGCGA GTGCGGCANA TGGTAGCGAT TCAACGTTCA      50
GATCTGGATG AATNCACGTA CCCCTGTCAA GCTCTTAAAA GGAAAGGGAT    100
CGCTGTACGT CACCAACCGT GACTGATGCA CCAAAGCTAC CAGGACGCGT    150
TCCGTAGGTC TTTCTCGCGT CGATGACTTC GTCGTTACGA GGCAGTGGAG    200
ACGAGGGCCA GTGTCTTCCT GATGGCTCGC TGNCTCGCGC TCCGCTGCCT    250
CGACANCGAC GGATCTGAGA CTCGAGGGAC ATAGGTCTTG TTGCAACCNT    300
ATCGTAACGG TGCAGCAACA GCGTATTGGG ATCTTAGCTT CTCCCAGGNT    350
CCCTGATACG GGTCGAAGGC GTCTGTTAAA CAGAGCCAGT CGGNGNGTTT    400
TCTTTAAAAA GTGCTGGCGG NGCTCTTCCC GNCCGTAGG GAGCAAAAAA    450
GTTCNTGGG GGGGATCCCA NTGNNNATNC GTCCNGGTNN GGGAATNTNA    500
NTNNTNTTCC ATCCGATTTN TTCTTANGNT CCGGCTCGAG GGCCGNACCA    550
AATANTNANA GCCCCCAAAA ATTTNNTTTT TNGCCCNCCC ATTTGCATTG    600
NNCCCNTNGN TTNCGGCCAC CC    SEQ ID NO. 37                622
```

FIG. 1J

Plasmid: 32

| | | | | | |
|---|---|---|---|---|---|
| ACCNNNTCNN | NANNATTTTT | NNNNAGNCNC | TTNANNTNCT | AAAGCNCATN | 50 |
| TANNCCTNAA | AAAAATTTAC | CGNGNGGNTC | TCACTCAGGC | CCCNGCCAAA | 100 |
| NAGGNTTTGG | TGTTTGCGCG | GCCGGTCGAG | CCCGATGTGG | CGGTGCCGGA | 150 |
| TNACGTNTCG | GTGTGGTGAC | GGTGCGGCCG | GAGAGGGGGA | GGAGNAGACA | 200 |
| GACNGNGANC | AGNGCGGTCG | NGGNCGGACN | GAGCCGAGNC | GTCTTNTTTT | 250 |
| NGGAGCNGCT | GTATNTCATG | NCCCGACANN | NCCGNNGGGA | NGNCTTCGGA | 300 |
| GCTACGGGTC | ANTTCNNCCA | CNACNTCATT | CNGTNGNCCT | NNNNANTCNGT | 350 |
| NTGGGANATT | TATCCCCNGG | NTTAANNNAC | TNNGNCCCTT | TTTTTTTTTT | 400 |
| TTTTTTTTTT | TTTGCNNNGG | CCCCGCACNA | NNNCACNCGN | AGTTGNTNAG | 450 |
| CCCNNNNCCC | CANCNNCTCC | CTTNNTATNC | CTAACNCTCC | CGGATGGCCC | 500 |
| NTTTTNTTNT | CTCNCGCCGC | CTCTNTGCTN | CTTCTCACAT | TANCATAACN | 550 |
| TCTACTTTNN | TAGCTTNGTC | TCCTTTNCNN | NTTTTCTNTC | TNATAAANNN | 600 |
| NCNNNNCNTT | CNNNCTNTTN | NCNTTACNTT · | NNCCNTGCTA | TCCNCCCNTN | 650 |
| NCCNNACCCN | TNNCAGTGGN | NNCNTCTCCN | NNACTTCTTN | NNCNATANTN | 700 |
| SEQ ID NO. 38 | | | | | |

Plasmid: 33

| | | | | | |
|---|---|---|---|---|---|
| NNTNTAGGGN | GTTTTNTNGN | NCGGGATNNN | NTAAGCCCNN | NTCTNTTTAG | 50 |
| GNATNNNGGC | CAGTCGTCAC | CNCNNTNCNN | GCNAAGNANT | AATGGGGGNG | 100 |
| NNGGGGGGGC | TANGGNATNT | NGAACNTCAN | NNGTGNACCN | CCANTCCNAG | 150 |
| TCAGCGANNG | CNAGTGANGA | GNCCACACAA | NANCGNNAGT | ANANCGACAT | 200 |
| CNATGNGTCT | ANCCTNACAN | GCNNCTTTTA | TCNNATCCAN | NNGTANATNN | 250 |
| NCAGAAGAGN | TNTCAANCAT | NTCGCTATA | NTNNCGNAC | ATAATTCGAA | 300 |
| NNANNTCTCT | TCGNANNNNT | CGCTNNNNNG | GCNTNTNGTN | GAACTATAGN | 350 |
| CNNCNANNTN | CCTCNCNNAA | CTNGCTNNAA | TNANTTTTTT | NNTTTTATTN | 400 |
| CNNNCTCCGA | CTCGANCNTC | CCCTNNGCNN | TTCNNNNNTN | NTNTNATTTT | 450 |
| NNNNCCACCC | NCTNGCCATN | TCCACANCN | NCTCNTNNCN | NGCNCCNNNT | 500 |
| TTTNTCANAN | CNNNCTTNTN | NANAANTTCT | CTCCATTNTN | CNNCNCCCNT | 550 |
| TCNANTNTTC | CTATATCCNC | NNANANCAAT | AACTNNTTTN | TNANTTCACC | 600 |
| NTACTTTNNT | NGTATACTTA | AACNNTCCCA | CTCCNTCTCC | ANTTTTNTNA | 650 |
| ANTCCNNCNC | CCNAATCNNC | CACCCNNTNC | NTTTTTNNCT | TTTATA SEQ | 696 |
| ID NO. 39 | | | | | |

Plasmid: 34

| | | | | | |
|---|---|---|---|---|---|
| GGTTTNGNAA | CTCTTGAAGC | TCTCGNTCCC | CTAGAAACAA | GGCTCAGTAC | 50 |
| GTGGAAGGGG | TGTGGCNTCA | CGCCTACACA | CCTGGGCTGC | TCGACCATCA | 100 |
| TAACGTGTGT | GATCTGGAGG | GGNTTCTTTA | CCTGTTGTGC | TGCGGACCCC | 150 |
| GNAGTTTCTG | CTCGCGGNAC | ACGTGTTTCG | GGCGGGAGAA | GCACGGTTGA | 200 |
| CCATTCCCCG | CCCTGCTCCC | CAAGGATCTT | TTACGAGCCC | GNTCGCGATT | 250 |
| ATATGACGNA | TGTGAACCTG | GCTGAACTTC | TACGTTTATG | TGTGGNATCG | 300 |
| CGGCTATGAT | CGCCCTTCGA | CTTCGGATCC | NACGCCAGGG | GNTGATGACG | 350 |
| ACCGANCTNC | NGNCNGNCTT | TTAATAGANC | CGCCCTCNCN | TNCNCACCNN | 400 |
| TCTCAACAGG | ANNTTGCTTA | AAAGNCGTGA | TCCNANCGNC | NGCTTCTTNG | 450 |
| GCCGTCNCNA | TANTTCNCTC | TTCNACNTNC | CTNNCTTNNT | CCTNACANTC | 500 |
| TNNCTTCNTC | CNTCNNGCCT | CNNTGCACNN | CNTATTTCTT | CTNCATCTNT | 550 |
| TTANCCTCCC | NTCNNANTTT | NNNTTNNCNA | TCACTCCANN | CACNNCCNNN | 600 |
| TNTTANCCCC · | CANNTCCCCC | CCCATTNTTN | NCANCTNCTC | CNCTGCCAAN | 650 |
| NNCCTNNTTT | TTANCCCCNT | CTNNCCATNT | TTTNCTTNGC | TTCNCNTANA | 700 |
| TCCANANTCC | CCCTNNACCT | TACANCTCTN | TATCCTCTNA | TCCCTCCNAC | 750 |
| TATACCCCTT | NTTNTATCNT | NTCCNCCCC | SEQ ID NO. 40 | | 779 |

*FIG. 1K*

Plasmid: 35

```
GAGCTCGTCT TGCAGCAGAT TGCGGGTGGA ATACACGTNT TCGCTCACAT      50
CGCACAGCTG CGTCTTTTGA CTGCTGACGG GTTTGACAAC AGAACCCAGG     100
GGTGAGAAGC AANAACGACG CGAGCAGCGA AACCAAAAAG AGCCCTGCCT     150
AATGAATCCC CGCAAAGTCT CGGCGAGTTT GAGCATCACG GTCCCGTNAA     200
TTAAAACGTG TACGCAACCG NNTGATNTCC ATGAACACGG CCCTGTTAAC     250
AAGGCTCCAA CCAGCCAATC ACCGNGTACT TGGNCTTNCT CCAAAAATGC     300
CAATAACGAG GNNGGGNTAG CCTCGNNNGG GNCTCTTNCA ACGGTNCGAG     350
GGATCCCGNN AGTTGAAANN TGNATNANGG GCCNTTCCCC CCCAGGNNNA     400
ACCTTGGNCC CCANNNTTTN GNTNNANANN AANNGGACCN NCGNCTGGGT     450
ACCCCNNCAA GANCTTTNAA ANTTNCCCNC CCANNTNGGA AAANTGTNNT     500
TNTNCCAANN NTTTTCAAAA NTTCNNCCAA ANCGNNNNNC CNNTTNNTTG     550
CAANNAAA       SEQ ID NO. 41                               558
```

Plasmid: 36

```
TTTTGANACT TNTTAAGCTC GATGACACCN TGANCTGATN GCGACAAACC      50
AGGAGCGGCT ACANCCACCG AAGACGATTT ACGCGCGCGC GATGCACAAG     100
CTCTTGGGCT ACCGCCCAAC GCCGGCTGCA ATGCCCTCT GAGCGACCTG      150
GNTCAGCTGA GTCGTGCTCT ACGTTGCGAT TGGCGATACT GGCGACTCAC     200
TACTGNCCCG GAAGAATNGG NTGATCCCGG CGAAGACGAT TCTTATAACG     250
AGTTACCATA CCGTACGTGG GCCCCCACCG ACTATANNCC TCAGNGGGAN     300
CCACAGACCG CATTCGGGGC AANCACAACC NTCGCTCGTC GNTTGTCTCA     350
TCACCGAGCC ANTGCCNTTT TGTTCCCTAC GGCGTCCCTT GGCCCTTNNA     400
GNCCNTCGAT CNNGTTGNN NGNCANTTTT TCCCNTCTCN AGTACCCNNN      450
GGNGGTGNTT NGNCNNTTCC TNTNNNACGA TTTTNNNAGT NNNNCCANAT     500
TCTTCAGNNT CCCTCTCANT CNCNTCTNNG NANTNTCNCC CCNANTCTGT     550
TTTTTCTTTN GTNNATTTNT TNNTNAATTT TCTTTCTNNN TCCCCCTNAN     600
NACCNTNNNC NTTNTTCTNT TCTTCTNCNC NNNTCTCCNN CNNTNTTNNT     650
CNTNTTNNTN NTNTNCNNTT  SEQ ID NO. 42                       670
```

Plasmid: 37

```
GAGCTCTCCG AAAGCTGGAT GNACGNGAGT CTGGTGAACT GGATCTACAG      50
GTTTCGCTGC ATCGTTTCAA TTTACAGAAA TATTCTCTTC GAACTCGCCG     100
GCACCTTCAG CACTTGNGTG CTTCTCTGGT TTAGTTTCCC AACAGTTGAA     150
ATGTGTCTGC TGTGCACTGT CCCGACGGGA GCCATATTAA TTCCCACCCT     200
GTGCCTCGGA ATAGCCTGTT GNTGTCAGAA AGAGATGNTG CGATACTCGG     250
GATCCTCTAC GCTCGNTTGT GTNTTAATTG ACACTTCAAT AACAAGTTAT     300
GACCGGTTTC TTGTNGTCCN GGGNAAAAAC CTCAACCTCG GGAATNGGCT     350
TGAGGTNGGG TGATGATCCN NTATTTTTNA CNCCCTNGGA ATTTANGCCN     400
NCCNNAAGAA AGGCCCTTGN NAATTTTCCC NTCCCNAAGG GGGGGGCCCN     450
NCCCCTTTTT NTTNCTTTNN CCNGGNTNGG GCAAAGGGGC CANCANTTAA     500
AATTTTCCAC CNNNTTTCTC CTTCCTANAA GGGGGTTNAA TTNTT  SEQ     545
ID NO. 43
```

FIG. 1L

Plasmid: 38

| | | | | | |
|---|---|---|---|---|---|
|NCNNTTTTNN|NTGTTCTTCT|ACTCTGAAGC|TCGAGATCNC|ACCGATGCAT|50|
|TNGNCGTGAT|GGAGATCCAG|GCACACCGTA|TCNATGTTCA|CGGTAAAAAG|100|
|CAGNCCCATG|AACTCGTNCT|GAATGTTCTT|GGACGATTTC|CAGACGTGAC|150|
|TGTCCGTTCA|AGTAATTGTC|CGGCAGGGTT|CCCTTGAACT|GCGCGGTATA|200|
|GCGAGTCATC|TTCTTGTGAC|CGTGACAAGT|GACTCTNTTG|NTTGTCCACG|250|
|TAAGCTGTTC|CGCGTGGACG|ATTAAGTGG|CGTCCTGACG|GGTGAGGGTG|300|
|GNCTTGTCAA|ACGGCACTTC|TTCGATCCAA|CAGTAGNNAA|NGTNGNCGGT|350|
|CAGGGTTAGG|AAAGGCAACT|CCNTGTNTTN|TNTTTATNNC|CNNNCNGCTA|400|
|ACGATNANGN|NTNAACCCTT|ATCTNTTTTG|CNCCANNNNN|CCCCCNTCTT|450|
|CTNCNCNNNT|NANANNNNNC|CNCGGNCNTC|TTCNTCCNGG|NGNCCCCNCA|500|
|NCNTNNCCCN|CNCTANNCNN|GCCNCCTTCN|NCNANTNNCT|TCTCTNCTNC|550|
|TTNCCCCCCA|NCTCCCTTTT|CTCTCNANNC|CNCNCNCCNC|NCTNTNCCTC|600|
|NTANNNCTTC|NCNNNNTCAC|CNCTNTCNCC|NNCTTTNCCN|ANCCCCCCCT|650|
|CCTTTCCCCC|TNCNTCCTTA|TCTTNTNTTT|TCANNTCN|SEQ ID|688|
|NO. 44| | | | | |

Plasmid: 39

| | | | | | |
|---|---|---|---|---|---|
|TTTTGANACT|TNTTAAGCTC|GATGACACCN|TGANCTGATN|GCGACAAACC|50|
|AGGAGCGGCT|ACANCCACCG|AAGACGATTT|ACGCGCGCGC|GATGCACAAG|100|
|CTCTTGGGCT|ACCGCCCAAC|GCCGGCTGCA|ATGCCCCTCT|GAGCGACCTG|150|
|GNTCAGCTGA|GTCGTGCTCT|ACGTTGCGAT|TGGCGATACT|GGCGACTCAC|200|
|TACTGNCCCG|GAAGAATNNG|NTGATCCCGG|CGAAGACGAT|TCTTATAACG|250|
|AGTTACCATA|CCGTACGTGG|GCCCCACCG|ACTATANNCC|TCAGNGGGAN|300|
|CCACAGACCG|CATTCGGGGC|AANCACAACC|NTCGCTCGTC|GNTTGTCTCA|350|
|TCACCGAGCC|ANTGCCNTTT|TGTTCCCTAC|GGCGTCCCTT|GGCCCTTNNA|400|
|GNCCNTCGAT|CNNNGTTGNN|NGNCANTTTT|TCCCNTCTCN|AGTACCCNNN|450|
|GGNGGTGNTT|NGNCNNTTCC|TNTNNNACGA|TTTTNNNAGT|NNNNCCANAT|500|
|TCTTCAGNNT|CCCTCTCANT|CNCNTCTNNG|NANTNTCNCC|CCNANTCTGT|550|
|TTTTTCTTTN|GTNNATTTNT|TNNTNAATTT|TCTTTCTNNN|TCCCCCTNAN|600|
|NACCNTNNNC|NTTNTTCTNT|TCTTCTNCNC|NNNTCTCCNN|CNNTNTTNNT|650|
|CNTNTTNNTN|NTNTNCNNTT|SEQ ID NO. 45| | |670|

Plasmid: 40

| | | | | | |
|---|---|---|---|---|---|
|CNNNNTGTNN|NNNGTCCTTA|ACNCTTAAGC|TCCTTGACCC|CAGNNACGGT|50|
|GTCCACGGGC|AGCAGGAATT|TGTCACNGCA|AAGGTATTTC|TTCTCCAAAT|100|
|CTCTAATATT|GAGATGGCCA|AAAGCTCCCG|CGCGAAGAAA|ATCAGAAAAG|150|
|GTAAAATACC|ATCCAGGAGG|CCAAGCGATA|GGAAAAGTTT|CCCCGTTCAC|200|
|CTTCCGAACA|AACTTCATCA|GACGCTTAGG|CGCGTCCTTG|GTGCTCACGG|250|
|AGCAGTTAAA|AAATTCACGG|ACAAGCAATT|CGTGACGCTT|CATGTCGGAA|300|
|ACAATCATGA|TGGACGGGGT|TACCAGTGTG|GAACGAAGTC|GGGCACGCCC|350|
|GGGCTCGCAG|GAAATAGATA|TAGCTCGTGC|CAACCCACAA|AAATCTGCAT|400|
|CTGCGTCAAT|ATTTTTTAGG|GTACAACTTT|CTTGCTTTTT|NGGGTTGCTA|450|
|GGGTNCGGAA|TTCCGNAATT|GGANAGATNC|GTCGNTTTGT|CCGNNCTTCT|500|
|TCCTNGGGNN|NNCGNTAAAG|GTANTNAGAN|TTTTNTNTCC|CGGGGNNTNG|550|
|GGAACCCCCC|TGGGNTTTTT|AANNTATTGG|NCNNACTTTG|TGTTNANCCN|600|
|NCCTTNNCNG|GNNNNNNGGG|GNCGTTTCCN|NNGGNTNTNN|CGNNNGGCAT|650|
|CCNTNGNNTT|GGNNCCCNNG|NTNNGGGGGN|NTTCNTTN|SEQ ID NO.|688|
|46| | | | | |

*FIG. 1M*

Plasmid: 41

```
GAGCTCTAAA GTATAANTAA CTTTTNAGGA CCCTGACCCT GTTCAAATGG        50
AGCCAACAGG ATGACACATA AAGTTATTCC ACTGATGGGA AATTTAGTCT       100
ATTAGAGCAG TGGTTCTCAG ACTTCTACAT TTCATGANCA GAACAACAAC       150
AATAATAAAT GGAGAACTTA CATGGGATTA ACAATTTTAC CACCTACCTT       200
TTGGTCAGCT CACTGAAAAA AAAAGAAACT GAACAGCAAG GAAAGAACAG       250
NTTACTGCCA CAACTGCCTT TCTTGTATTC CATTTNGNTA CAGACTGGTT       300
AANAAAAAAA AAAAAANGTC ACANNTTGGG NAACANTCCA CAGACCCATT       350
NTTGGGGAAA AAATGGGTTA GAGAGTTTTT TANGGGCCCT NCTTATTTTT       400
NAAANTNGGA CGNCTTTAAN TCATNTTTTG GGGGNCNTNA CNATGCCNNC       450
CTTAANTTTN NGNTTACATC TTGNANGNTT CTCAANGCCA ANAATNTTTN       500
ANTNCCCTNC NATTNAANCA ATTNTGCCCA ATTCCCCTNT TT   SEQ ID     542
NO. 47
```

Plasmid: 42

```
TNGGNAACTC TCAAGCTCCC CACCCCATTG ANAAATATAT TAACATCACG        50
TCATCTACTA ANCCCCATTC AAGTTGTGGT CTATGGATCA ATATCGGCAT       100
CACTGGGGAG CTTGTAGGAA ATGCAGACTT TCAAGNTCGA TCCCAGATCT       150
GCTGCTGAAT CAGAAGCCGC ACTTTCACAA CATCCTAAGT GATTCGTTTG       200
NACACTGCAG TTTAAGAAGC ACCCCACATT TTGTTGGATA TTCAAAANAA       250
TGAGAACCTG ACTTTAGGGT CTCCTCTCTC CCACCCTACC ACTACCTCCA       300
GCAGTCTCCT TGTCTTCCAG ATTCCACCTT AAAATTCAGG AATCACCATG       350
CACTGAGGAC AGGCCTGCAC AAACATCTAG TTCCCCATGC TTTAGGAAAA       400
GTGACAAAAA CCCACAACCG CCTTCCCTTT CCCAGGGTCC CTCCTGCCCC       450
CAGGAAAAAT AGGAANTTCC CTCAAATCTT CCCCCAANGG CCGGGTGNAG       500
GNGGGTCAAA ACCTGGTAAT CCCAGGACTT NGGGAGGGTT TGANGCAGGA       550
GGGGTCAACC NNAGGNCAGG GNGTCNAAGN CCAGGCCCGG CCGAATGGGN       600
NAAACCCCNC CTTTCNAANN GTCAANANTT GTGGNGGGGN NNNNNGNCCN       650
NNNGNCCCNN TTTTCGGGNG GTTGTT      SEQ ID NO. 48             676
```

Plasmid: 43

```
NGNCTTANAA TTNNNNNATA GCCTTAAAGC NTNCTAAACT AGTTTGGNAA        50
NTCATTATCA GGGAACNTNC CGNTTCANNG ACAACACCTC ATCCTCCANA       100
ACGTCCCCAT GGGNCGTCAC CTCATCCACA GNAGTGGCAC CAGNCGCGTC       150
CAAAATGGAG GTGGTTTGNT CGGAATCCAN GTCCACCAAG CCGATAACTT       200
NCTGAACTTC ACACAGNGNC ACTTGNTNCN NNGAAAACTT ATTCAGCAAC       250
ACCTCCAGAG TGTCGTCCNC AGACATGGNA NACTCGNCCA CCACCAGTTT       300
CAAGATCATN NCGTCCAGAG CCTGNATAAT CCGCTGCGAC TTCTGATTCT       350
CCACCTCGGC GGCGGGGTGN NTTTGTGGTT GGNANTTATC CGANANGAAG       400
TCCTGCNAGC AGGACGACAT CTTCATCTTG GNANCTGCCG NTTNNAGNGG       450
GATCAGNTTG GAGCAGGNTG CTTTCGNTCA CTTCCTGGAT CCCTTCGCNA       500
TNNGTNTTAN TTTTCCTNCG GCTGTTGATC NCTTNNGTTC TGAAGTTTTT       550
CCTCGCAGGA AGCAGTGAAT CTTNTNGAAT CNTNCATTTT CTNNGCTAGG       600
NNTGTANCAA GGANATTNCN CNATTCTTC GATTCTCNTC NTNCNNAATN       650
TNNNATNTTC ATANTAGNNT CNGNCAAGGN TNNTTCNCCN TCGTAANG       698
SEQ ID NO. 49
```

FIG. 1N

Plasmid: 44

```
GAGCTCCAGA GGAGATNGGC TCGCGGGNGC GGTCGGGAGG NTCGGAAGCC     50
TGGGGGNGAC CAGGGAANCN ANGCCGTGNA NCCCGCNATA GGNCGCGGAC    100
TGGTTTTTTT TTTNNTTNAT GNGGTGCNCG GACNCAGGGN CCNGTTCGGN    150
TCGCAGACTC NAATAGNNCN CNATTCANCC TNGCCTNANN ATTCANGTAA    200
ACCCCACNNN TTTNTAANAA ANNGCCTANG TCCCNNCTGN TAANACGCCC    250
CCCCGCCTTT TNTTTTTTTN TTTTTTTTTT TTTAATNCCC NACNCNNAAC    300
NGAAANCTCN AAANTTTCNT TNCAAANTNA TNANNCTNTT NNANATANTT    350
NTNTCTNACT ANNTACTCNN NCNAANAATA ATTNTAAAAT AANCNATATA    400
NTNANAATAA AATTATATAA NNATNTCCNC CTAAATTTCC NTCTTTATAT    450
ACACTCCANA TNAANTNAAN NTTTATCTTT CTATTATNTN ACTACANCAA    500
NATNNTCATA ATAATATTCA ACTNCTNATC ATTNTACATN CTCTATATCA    550
TNANCNNANA CAANTCNTAT TATANNCNNA NTACAATACA TTNTTTTNTA    600
TAAAATATTT     SEQ ID NO. 50                              610
```

Plasmid: 45

```
GAGCTCGTCC CTTGCGTACA AGACAGCTGG TTCGTGATGT TCGCAATAAT     50
GACGGAGCTG AGCCGTGAAC ACCAGCTGAT TGAACAGAGT GCAGACGTGC    100
GAGATGGTGG TTTGGATCTG CCCGCCGGCT AGCGGCGGGT CTTGAGTGTG    150
CGGTTGCAGT CGACACTTTA TATTTTNTGT AACGTTCACG ATCTCTGATG    200
AATCAACTCG CGTGCGAGTT CGTTTTAACT GTATGATGCC TTGGATGGAA    250
CTTTCGATAG TCCCGGTCGT TATAAAATAT AAATAAATTA CTGTTGGGGC    300
GAGTGCAGCC GAAAGTGGNA GGCAGGTTGC GAATAAGCAG TTTCTTCTTA    350
CCTTCCGCGC GAATCGGACT CCGGTAAGCT TTAGAAAGGT TATTGGACGN    400
NNGGTTTGNN GTCCCCGNGC TCTCTTTACG GTTCCGCATG GAGAATCGNG    450
NNNCGGTATA TATTTTCANA GGCATGGGAN GCGGTNTCNN CNNGGAAAAG    500
GCTAACGGGG GNTCCANNGG GTTGCCNNCG GTTCNATANC CNNNCCCCAC    550
CACGTGGCCN ATCCAAANNA CAATNCTNAA ANCACT     SEQ ID NO. 51 586
```

Plasmid: 46

```
TNATTTGAAG TCNNNNNATA CNCTANAGCN TTNNAAACTA CATNATCGAT     50
ATTGAGGCCG ATATTNCCCT TCTNGGAAAG AGCTGNGAGC GCTTNCACTT    100
TTGGCAGANG CTCGTCCATG ACGCGCNCGC TCTGCGCGGG AGCATAACGC    150
GGGTGCAGTG CCGAAAGCTT GATTGAAATA CCCGGGNCAT CATAGATGCC    200
GCGACCGGCC GACGCGCGAT CANTCGNGTN GATCGGANCC TCATAATCCT    250
TGTAATAGCG TTCTGCATCA GNCGNCGNGG TNGGCTGGGT TCACCCAGCA    300
TATCATAGGA GTGGCGGAAG NCGNGTTCTT CAAGCGACTT TGNACGNTTG    350
GANTGCTNCA TCANTGGTTT NNNTNATTTT AAGAGACTGN TCGGCCGTCA    400
GGNGCATNGC CAATATCCAC GNCACGANGG GTAACCCCNN TTCAANCNCA    450
AGGGAGCAAT NGAAGGCGCN TNCANTTNCT TCCGNACAGG GCNNNTCNNC    500
ATTAANGNNN NTTCCNNCAA NTTGACNNNT GNNCAAAAAN GNCCCANCCC    550
NNTNGAATCA GGNCAAANNA AACGGNCACG GGGGAANTTN TAANTNCCNN    600
TNNCCCTCCC NNNTNTTTTC ATNTCNAAAG CATNCNAANN NNNNNTCCTT    650
TCCNNCTGGN NNCCCCNATC ATG     SEQ ID NO. 52               673
```

FIG. 10

Plasmid: 47

| | | | | | |
|---|---|---|---|---|---|
| GTTTTGCACA | CTCNTGAAGC | TCCCACTGCC | ATCGAGTGGN | GGATAACAAA | 50 |
| CTAACAGCCA | GANACATGCC | ACGATCATTT | GTATTTTATT | TATTGTTGGA | 100 |
| AAATCANCAA | CAGTGTACTC | TGCAGTTCAA | TCGTAACCCC | TGCTTATTTT | 150 |
| TCAGCGGTGA | CGGTCTGAAC | AGTCCGCTTC | TACACGAGCC | CAACCCCTTT | 200 |
| CACCTAACAG | TCCACGCTCC | CTACGACATT | AACTTCGGTC | ACCACTCCAG | 250 |
| NCAGACGGTG | GAGATAGACA | TCCGCTACGT | ACAGACTGGC | GGCCGCTGCT | 300 |
| TTTTGGTCGN | CAACCTGCCA | CACGAAGACT | CGTTCTACAC | CGGGATGTGT | 350 |
| CTGTGGCGAA | CAGAGGCACT | GAAGATCACC | CTCTGGTCCC | GGNTGCGCAC | 400 |
| TACCATTATC | CCTCAGGGNA | TCCCTATCGC | CGCGTTGGTA | TCAAATCAAC | 450 |
| GACATCGACG | GCAATCTTNA | CGCGTATAAC | CATAACACGG | TTTTCCCGNA | 500 |
| NAGTTCATCA | TNNCCGACAG | GAACANCCTT | CTTCCCTTAG | GGATTTTAAG | 550 |
| CTCCCCACCA | ATAGTTTCCC | TAACCTCATC | CTANGGGCAA | TTATTCCNCA | 600 |
| TCTNAGGGGN | ATCTTCCTTA | ATTTNTCTTT | ATGGATAATG | GTAGNCGGG | 650 |
| GNCCNTCCGT | CTTCTAGTGG | GGNTGANCCC | CAANTNGGCG | GGGTANCATN | 700 |
| CNGTTTTNGG | TTGACCTGGT | SEQ ID NO. 53 | | | 720 |

Plasmid: 48

| | | | | | |
|---|---|---|---|---|---|
| CTGNCACCCG | TNAAGCTCAN | TTACCACTTC | TTGGGAGGAG | GAAATAGATT | 50 |
| TTATCTATCT | NTGGAGCAAT | ATTTAAAGTT | TAGAATTCTT | TTGTTTTCAT | 100 |
| ATATCATTTG | CATCAACTAA | TGGAGAGTTA | AAATGAGAAC | CCCTACTACC | 150 |
| TGCCAACATC | ACTGCTCTGT | GGTGACTATG | AAACGAGTAA | GAGAAACCAT | 200 |
| AGATGCATTT | TGACCTTGTG | TCTGCCTTGC | ACTGCTCCTG | TATCCAGCTC | 250 |
| TACTTGGAGT | TTAATATTGA | CTCTTAAGAG | GACAAATTAN | TTANTGTAAT | 300 |
| AGTACATNGA | AAATGTAAAA | CACACANCAC | CACNCANNNG | CCTNCTCAGC | 350 |
| ATTGGCCTCA | TTCCCATTTT | TCCTCTGTGA | CCCTGTGATA | GACATTAGAG | 400 |
| GTTTCTGCCT | TTCAGAAGCT | TCTNCCCTCC | CNCNCTCGGA | GATGGAGTCT | 450 |
| CACTTTGNTT | GNCCAGNCTG | GAGTGCAGTG | GTGTGATCTC | GGNTCACTGN | 500 |
| AACCACCGNC | TCCCAGGTCA | AGCAATTCTC | CCTGTCTTAG | CCTCCCGAGT | 550 |
| NNTGGGATAC | AGGCANACGC | CACACGCCCA | GGTAATTNGG | GTTTTANGNN | 600 |
| GAGNTGGANT | CCACCAATTG | GCAGCTGGTC | TT SEQ ID NO. 54 | | 632 |

Plasmid: 49

| | | | | | |
|---|---|---|---|---|---|
| GAGCTCCCGA | CCTCAGTTGA | TCCATCCGNC | TCTCAGTCTC | CCAAAGTGTT | 50 |
| GGGATTACAG | GCGTGAGCCA | CTGTACCCGG | CCAAGAAGTG | TTTATAAAAT | 100 |
| TGTTGAAAAA | TCTGCTGTTT | GTGGGAGCTT | NTACTCAGGC | ATTCTAAACT | 150 |
| GCTTACCGGT | GTCTTTTTGG | CCAGTATCGT | GGATTGCCTA | CTTGAACAAG | 200 |
| ACTNGTAGGG | GAAGCAGATG | GTCTTGTCAC | TGGCCATGAG | CTGCTTACCA | 250 |
| TATATTGAGG | AGCCACATTC | ANCTAACTGN | TTTCCGAGCG | ATCATGGAAG | 300 |
| TTTCTATTAG | CAGCCTGCAG | TACATCAGAG | AAATGATAGC | TTTNCTTTTN | 350 |
| TTNTCNTCAA | CTTNAACGTN | CTGGGATACA | CGTCTTGAAC | ATGNAGGTTT | 400 |
| GGTACANAGG | TTTTCATATG | CATGGAAGTT | TGTTNGNTGG | CCCTATCAAC | 450 |
| CACCATTTNG | GTTTAAGCCN | NCATCNTAGG | AGGTGCCCAA | TNCCTCCCCC | 500 |
| CTTTCCCCCT | ACCCCAA | SEQ ID NO. 55 | | | 517 |

FIG. 1P

Plasmid: 50

```
ANNTTTNNNN  TTTCNTGAAC  TTNTANAGCT  CATGNTCCCC  NNAANTGTGG        50
AAGGGGGTGG  GCACAGANAG  CCTGACCTCC  TGNGATGTGT  GGGTGGNGGT       100
GACCACGGAA  GGCTGAGGTC  CACCGNGGTG  GCGGTCACTC  TANGAACTAG       150
TGGATCCCCC  GGCCTGNAGG  AATTCGATAT  CAANCTTATC  GATACCGTCG       200
ACCTCGAGGG  GGGGNCCGGT  ACCCATTTCG  TCNTATAGTG  AGTCGTATTA       250
CGTGCGCTCA  CTGGGCGGCG  GTTTACAACG  TCGNGACTGG  GAAAACCCTG       300
GNGTNACCCA  NCTTAATCGA  CTTGNAGNAC  ATCCCCCTTT  CGCCAGCTGG       350
CGTAATAGCG  AAGAGGCCCG  CACCNATCGN  CCTTCCCAAC  AGTTGNGCAG       400
CCTGAATNGC  GAATGGGAAA  TTGTAAGNGT  TCANTATTTN  NGTTNAAAAT       450
TNCGNNTTCA  ANNTTTNNGN  TTAANTCAAC  NTCATTTCTT  TNACCAATAG       500
GCCCNAAATC  GGNAAAATCC  CTTATTAAAT  TCAACNCAAT  AGNCCCANAT       550
AGNNTTNGAN  TTTTGGTACG  ANTCTGGGNA  NAANANTTCC  CCNATTCAAN       600
TACCTTCGCN  TCCAATNCCA  AACGGTCTAA  AACCCNNTTC  AGNNCNNATC       650
NCNCNTNNNN  TNAACCATCA  CNCTNTCAAT  NTTNA    SEQ ID NO. 56       685
```

Plasmid: 51

```
GAGCTCAGGC  TCCGGAGGTC  ACCCCNATGC  ACACATCCCA  GGAGTTCAGG        50
CTTCTNTGGA  CACCCCCTTC  NACACATCCC  AGGAGAAGGA  GCTCCAGCTT       100
CTGTTCCCTT  NAGTGAGGGT  TAATTGCGCG  CTTGGCGTAA  TCATGGTCAT       150
AGCTGTTTCC  TGTGTGAAAT  TGTTATCCGC  TCACAATTCC  ACACAACATA       200
CGAGCCGGAA  GCATAAAGTG  TAAAGCCTGG  GGTGCCTAAT  GAGTGAGCTA       250
ACTCACATTA  ATTGCGTTGN  GCTCAACTGC  CCGCTTTCCA  GTCGGNAAAC       300
CTGTCGGGCC  AGGTTGNATT  AATGAATCCG  GCCAACGCGC  GGNGAGAGGN       350
NGGTTTGGGG  TTTTGGGNGN  TCTTCCGNTT  CCTCGGTCAA  TTGATCGTTG       400
GTCGGNNCGT  CCGGTTGGGG  NAANGGTTNA  ANTCACTCAA  AGGNGGGATN       450
CGGTNTCCAA  GATCANGGGT  TCCGAGGNAA  NANATTTANN  AANGGCANNA       500
AAGGCAAGAC  CAAAAGCCNT  TNGTTGNTTT  TTNNA    SEQ ID NO. 57       535
```

Plasmid: 52

```
GAGCTCTACT  AGANGCGGAG  AGACGGGTGC  GCGACGGAAA  AATTCCGGTA        50
CCCTTTGTGG  ATCGCGATAG  CCTGTTGGCC  AACGTTATTC  CCGTCGCCCC       100
CANTCNCAAT  CCGGAAACTG  AAGGAAGACC  GGAGAAGAAA  GCACTGACAC       150
GACAGTGTTC  GCTCCCTACC  CCCCACCCTA  AGAAGCTCGG  AGTCCAGCCT       200
GATTCCGATA  GCGACAGNGA  TACGATTATC  GATTTAACTA  TGGAAGGGGC       250
GGTATCTCTG  TAGATTNNNN  NNNNNGNTGA  ATTGTGCAAC  CCGNATTGNT       300
TGGGTGTCAC  TTGNAGACAA  GCCTTCTTGT  CAATCANTAG  TGTNNTTTTN       350
GTAATAAACG  GNTTNGTNGT  TTAACAAGAA  GNNNGGGTNT  CTCATCTTCT       400
NGGGGGTGAT  GAGNGNCTAC  CCCCCTTNTA  AAGNNATCGN  TTANANTNGN       450
NGTNTNATTT  GAGTTTTTTC  ACCCCNATTT  TATNNNTATC  AANNTCTTNN       500
TTGGNTNTNN  NTTCTAATNT  CATNCCCN  SEQ ID NO. 58                  528
```

FIG. 1Q

Plasmid: 53

```
GAGCTCGTCC TGGGGCTCGA TCCAAGCGNA ATTCACGACG GGGACTTTCA        50
AGTGTCTCTG CATCACAGTG GNGAAATAAC AGTCCTCGGT GGGTGGACTG       100
ATGGGNAAAA CGGTGTTCTC CTCGACGATT TTGTCTTTTG CGGNCCACAC       150
CGAAGGGGTT ACACTCCACA GATGGGCAAC GTCCTCGTCG GGACCGATAG       200
CCAGAAACTG CACATTGCGC GACCCGTATT GTTGCATCTC AGTCCGGAGG       250
GTCTCCCACT GCGTCGTTGG GAGGCGACAG NCGGGGGTTT NCGATACAAT       300
TTCANAACTA AACTNGCCCN CCTTTGTCNG ATGGTGCGAT CAAACCCACT       350
CGTAAGGGTC GGNAGACCGN NTCTTTACAC AGGTCCANCG CTNGTGCCGC       400
AGNCNCCGNA TTAGTACATT TTNTNCAAAN ANCCCCTCTC AATTNAACTC       450
CCCAGGAGGC NANATTGGTT NAACCCCCAG ACGCATTAAC ACCNTNTTTA       500
AGNCCCCTTN AACNAAGTT  TAANNCCCNC ATTTTANAAA AGCCNCTNTA       550
AAGCCANNTN CAGCCAATCA TGATNCAANC CTTTGGCCAA NCCCCTNCTT       600
CNCATTCCGG AANACTTTAG TCAAANTANC TTTNGTTNCC CCC SEQ ID      643
NO. 59
```

Plasmid: 54

```
GAGCTCCGNG TTTCACCCNC TCCGAGGAGT NTCCCTACTG CCACGNTAAA        50
TATGAAACTT ACCTCAGAGT CATGTCGGAC TTTCGNGAAC TGTTNCTGCG       100
ACAGNNCANC TTCGANGGAG TACGNTCGCG GGTGAGTGAC CACATCGATC       150
AAGTTATGTC ATATAGGAAN CCCCAGGAAC TGGNTCGNGC ACGTCAGGTC       200
CGGTGGACAC ATACCGGNNC TGAGAGATCA GCTGNTGGNC NGACAAANAN       250
CTNTTTTTTT TTTNTCTTNT TNCGNGGCGA CNGGANAATC NTATNCATGN       300
TGGGGTGNGG GACCCTCATG GTGGGAGANN GGGACCCCNN TCGTTNNCAT       350
NGGGGCNNNC CACCAANANT TTCATCTTAC NNCCCCCNTC AACNAATTTC       400
CTATTCAANG NNGGNTTNAN ATTTCCNCCC NACNNGNCNA ANNCCGNNTT       450
CTTCACCCNA ATCCCNTTTA ANNAANNTCN CANCNNCAAA CNCACCNCCC       500
TCACANCANC NCNTNNNTNC CCCTGCNNTN NNNCNCNNCN NANTTTCNNT       550
TT       SEQ ID NO. 60                                      552
```

Plasmid: 55

```
TTTTTGNCAN CCGTGAAGCT CAGGNCACCT TAAATCGTTA CTCTCACCTA        50
AAACGTGTTA GCATCTACGA TCCCCTGAAC ATTGGTGTTA ACTGTTTTGA       100
TTAAACACTT GACTCTTTGT ACCCGCGTGT CATGTGTGG  GTATCTGAGA       150
TGAGGGCCCC GCAACATATT TAGAGGTGTG GGCTCTTCAC GAACGATCGA       200
GAACTATGCG ACTTCGTTCG GAAGAAACGG AGACGGTTCG TTCCATCTTT       250
CTATTACGAG TTTACATTCT CATGTGGATC GAGGGCATGC TCTTGTTGAG       300
CACGTGCGCA CTCTGCTGGC TGGTGTTGCC AGAGCGCTTT GTGCACCTTT       350
TACCGAGTAT TCGTAGGANG TTATTTTGGT TTAATGCTTC CTATTATCTG       400
GNNGGGGAAT ACTTCACTTG GGCCCGAGCC TCCAGTTTCC CAGGGGAGCT       450
TGTACGGTCT TGTTGGANTT ACACGTCCAC ATGGCCNNNG GGGACACCGN       500
GCCGNGGNTT CAATCCGNAA ACCCNTCGAC CCCTTACGCC ATNNNGGCTA       550
TATCTTGNTG NNATCNNCC  TNACCCNTTC AAGCTTCNTT NGGCNNAGNC       600
NNNGACCTTC ANCCNNGGN  NNNGNCCCNC CNNCCNNATN NTNNCCNNAN       650
CNT      SEQ ID NO. 61                                      653
```

*FIG. 1R*

Plasmid: 56

| | | | | | |
|---|---|---|---|---|---|
| GAGCTCACGT | TAATGGCAAT | TTGCAAGGGA | ACACATCACC | CACTGGCTGA | 50 |
| CTGTGGGATT | TTTATTGGTC | TCTTTACTTT | TTAAGCGTTC | TCGCCATCTT | 100 |
| GTGGCTACTT | TCAATATTGC | AGTTGAATGA | TTGGGCACAG | GTTCAACCAC | 150 |
| CTTGCAAATC | ATTAACTCAT | CTATTCAAGT | ACTTNGGGAG | ACTCTAATAT | 200 |
| CTCAAGTACT | TACACAGAAA | AGCAAGTGGA | CAAAAGCAAA | TAATAAGAAA | 250 |
| AAAGCCTAGG | AGGAATTAAT | GTAATTATTT | TTCACTACAC | TTTTAANCCT | 300 |
| CAAGTAGNCA | GGCTTGTCGC | TGCCAGAGGN | CATCAAAACT | TTTCCATTTG | 350 |
| GGNGGGGAAG | GNNNGNTTGA | CGCCTNTTTC | AAAGATTGGG | GGGNAAANNN | 400 |
| NGGNAGGNAG | TCATTTGNGG | TNAANNNGTN | CNNNACCAGC | NNGNCANATN | 450 |
| GNANNCCCCN | CCTNTTCTNN | AANANANATT | NNCGNTNTTG | NNCAANCNCN | 500 |
| NTNNCCCCCC | NCNGGNNGGN | NNNNATTNNN | TCNNNGGG | SEQ ID | 538 |
| NO. 62 | | | | | |

Plasmid: 57

| | | | | | |
|---|---|---|---|---|---|
| GGGTTTTGAA | AGCTCTTGAA | GCTCACCAAC | CCTTGAGGAG | ACNAGTCGGC | 50 |
| GCTCGGGACT | CACATCCCCC | GACTCATTGC | GCTCTTGGAT | CACGACAACC | 100 |
| ATCGCGAACT | GTGCAATGTG | CTGGTCGGGC | TGCTACACCA | GAACACCCCA | 150 |
| CATGTGGGGC | CGTTCCATCC | GGCTTATCGG | GCGATTAAGA | AACTATCTAC | 200 |
| AACAGAAGTT | TCTCAATATC | TTGGTGGATA | GCGGACTCCA | GATCGATAGT | 250 |
| CTTTTTGAGG | GTTGTTACCA | CAGCGAAGCG | TACCGCTTGC | TGTTCCAGAT | 300 |
| CGAAAAAACG | AACTCCACGC | CTAGCTCTCT | ANGCTGTGCA | AGCACCGTTT | 350 |
| TACCTGTCGG | TGAAAACGAA | ACTGAAGGNA | NACCTGTCCC | CGNCGGCGTN | 400 |
| TTTTANTGAA | ATNCTNAAAT | GGCTCTCATG | AAATATGACG | GCCTTAGTTT | 450 |
| CGTNTTNGGA | NNGGANAATT | NTGNNTCTCC | CCCCAAACAT | NCCNGNCNTG | 500 |
| GNCCCGTGNN | TTNGACCCTG | AACTTCGCG | GGGGNCCNNT | NNCCTTNTGA | 550 |
| CAAACNGNCA | NTTCNTTCNT | NGNTCTCGTA | NCCCACCNNT | TTAGCGGTNT | 600 |
| NNTGG | SEQ ID NO. 63 | | | | 605 |

Plasmid: 58

| | | | | | |
|---|---|---|---|---|---|
| GNTTGCAACT | TCTCATAGNT | CAGACACCCC | CTNANACAAN | TTGGCGGCTT | 50 |
| GTTCGAGTCG | TGTCCGCATG | GACTGGAGTT | CCTCAACGGG | CAGGGCAGCC | 100 |
| ACTAATGATT | TGATTGTATC | TTCTTTGCAG | CATGGCGGTG | NTTTGGCGTT | 150 |
| TAAGATCTCC | CTGCAGTTCG | GTTATTNTTG | TGTTTCCTCG | NTGCAGTAGT | 200 |
| GTCGTCTGCG | CCTGACTATC | GANTTTCGAT | AGGATCTGTT | TTGTGTCTTN | 250 |
| GTTGTCAAG | GAGATTCTTT | CCAGGTCGTG | ACTATCGATT | CCATAGATGG | 300 |
| CGGCAGATAG | CTGCTGTAGC | GCTAACTGGA | CCTGTTTTTG | CTGTTGGCTG | 350 |
| GTGATCGTC | GNCGACCGNT | GACGGCATTC | ACTACCGCCG | AAAAGTCTTG | 400 |
| TNGTNGAAGG | CAGACGAACC | TTTCGNCGAC | GTCAANTGGC | TTCTCCTCCN | 450 |
| CNTNTTCCCA | GCAGNCCCNA | NAGGGAAGTN | CCGTATTAGN | AGGNTTCTNC | 500 |
| CTTCCGGCCT | TCAAAAATCT | GNCGAACCCA | TTTCAATAAC | CTTTNNGCCC | 550 |
| CAAANTGNA | ACCTANGTNA | ATAAAAACCG | CGGCAAAGTN | NGCCTATCAT | 600 |
| ACACCCCNTT | GTACGGTAAA | CTTTAAGNTT | AAAANTTTCA | AANTCTCGCC | 650 |
| ACCCANAGTG | AATCCNTGCT | AGCNANGAAA | GGNTNNATCG | ATTCNCTCAA | 700 |
| ATCCCNANTT | CNCCCCCNTT | NAATCCANNN | TT | SEQ ID NO. 64 | 732 |

FIG. 1S

Plasmid: 59

```
TNATTGNATA CTCTTAAGCT CTCCGGCCCC GCCNAAAACC ANATTTCTCG      50
TTCGCTAGTT GGCTGNCCAT CANCTNGCTG TCATTCCTTT TTAATCAGTG     100
CAACGAGTTC TGGGGGTGGT TGGAATGGCT CGCCCTCCGA GAGNGAGGAA     150
ACATCGTCGC TATCTCCTAC ACTACCGATG TGTAGCGGAG ACGACGGNTG     200
GGTATGATCG NCGCCATNCN TNTTTTNATC ANNCTCCTCG GNGTCGNNCN     250
CCTCCNCTCC GGTGTCCTCG TATTCATCCN CGGTCTCCTC GACACCTCTC     300
AACGTACTGG NCGNGTNACC TTNAGATACG CNANACACGN NAANGCNCCN     350
AGACTNCGNN GGTGGATTTT NTTTTNTTTT TCTTCCCAAA NCCACTNTTC     400
CGGNGGTCCC NNNCANTCCG NCTCCATAAN TTCATCCCNN CNNTNTNCNN     450
NNCCCATCTN GGGGNNTTCT TTGNAATCAG AACCNGTNNG NAANACACNN     500
TAANNNCNNT TCCNNNNTAAN NNGCTNNCCT CTNNTAACCT NTTCCNANNA     550
NNCTNTCCTN NCNCNNTTTT TCNNATNCAT NTCACTCTTC TNCNNTTNTN     600
CCTNCTTCNN NCTNNCCCTT CCNNTTTCNC NACCTNNTNT NANCTCCNCT     650
CNNCCCNCTA TCNNCCNTCT ACANCNACGN CNTTACCTAC ATTNTNCAA      699
SEQ ID NO. 65
```

Plasmid: 60

```
GAGCTCCATC TCTGTAAAAC CGTGGCCGCT CATAATGCGA TGTTGTGCCC      50
TCGTTTCGGG AGCGTTGATC GTTCTAAGCT TAGTTCGGNA AACAGTCTGT     100
CTTATGGTGT GGGTAGTGGA TGTGCACTTG ACGTCATTAT GTGCGAGAAT     150
CGGAGGCGAA CCACCAATTG TACCGATTTA GCTTGAAGGT GAAAAAAGAG     200
GAATGGTTAG TCTGCCAAAA GACGGNATCC GAAAATCATG AGTCCAGTAA     250
TATACAATGA TGAGAATTTC CACGGTACAA AACGAATTAA CAAGGGGAAC     300
GGCTCCACCG AGAAACTCCG TACTTGAGCG GGGGANAGGA AGTCNGNNGG     350
NTAGAAAGTC CCGGGGGAGA AAGTTAACAA GNAGAGCCAA GGTAGCANCC     400
CNNCCCATTT TNTTTAAAAN GATGGACTNT TGGGGAGGGG NATTNNCANN     450
AANNNGTTTG NANAAANATC AAGGGAANAA GCCNCCCNAA ANNTTNACCC     500
CCCCGGAANG GNCNGGTTCC CGNTTTTTAA ACNNTGTTTT CCNAAAATTA     550
AATTANNAAA A   SEQ ID NO. 66                               561
```

Plasmid: 61

```
GAGCTCATGN CACNCTGGAA NAAAGCAGTT TCTTGATCAA TCGTAATGTC      50
ATACACTTTC CTCAACAATT CCTTCTCATT TAGAAAGACA GAGTTGATCT     100
GAATGTGAAA CCACACTGCA GGGCTTATCC TAAGCATAAA GATGTCCTTT     150
GGGAGTCTTT TCAACGCTTA AGCTATTCTC AGTCAACCCA GAAGAGGGTG     200
CAGGCAAACA CACAGTGACT CCAGTACCTG GAAATTGCAG CTTGCCTCTC     250
TTGTCACTGA CTGTTTTATT ACTTTAGTGT CTGATTTTTA TGAATACTTG     300
CAAGTAACTA CAAGGCACAC CCTTTTAATT ATAGTTTTAT TCATTCACTC     350
AGACAAATTA AAGGAACCCT ATTAGCTGGG CTATTTTAAC AAGTTTATGA     400
CATACAGATA TGTCTTGAAA ATTTACATTA ACAGGGTAAA AGGCTGGATN     450
TNTCAACTTN CTCTGGGGGG GCTGGTATTA CTTNATGCCN TNAAANTGAT     500
TATTCCCTCN CTTTNCCCCA TACAACCCCG GATTAGGAAA GTAAACCCNG     550
GTGAAAGGAT TTTCNTTGGC CCCTNACTNT TTNCAAGAAT TTTAAGGNNT     600
GGNAATCAAA ATAGGTGGGC CCCCCGGNGG NGGCAGCCCT NN SEQ ID     642
NO. 67
```

FIG. 1T

Plasmid: 3B11 T3
Accession 1: U27475

```
GAATTCAGCG TGTCGGAAAC GCTGTATATA TGCGAGTGGG CCGGGTATCC       50
ATGACGTTGA TTTGCGTGGT TTGTGGTTAC TGATCGGCTG TCGGCGGTCG      100
CATTTCCACG GAAATGTGCA CGTNCTTCGC GTTCCGAATN ACATTTTTG       150
GTAAANCAAG CNGCTCCAAA GACTNGGCCA CAGGGGNGTA GGTTATGTTC      200
NGTGCGTANG ATCNATNAAA CAATTGGACC GGTNTCCCTG TGGGTTTGNC      250
GGGGGNTTAT TGNNGNAAAN ANGCGGAANC CCCCTNGTTT CNCCAACCCT      300
CTTTNCCCCT TGGAACCCAA AACNCAGGTG NGGGCCCCTC NNNGNTTNTA      350
AACCNTCANA CTTTTTTTTG GNGAAGGCAA NCCNTCTCCG GTTCANTNTN      400
GGGNTTCCCA GGGCTTGGNT CNNANTTTTT CCANNNAAGA AACNGCCCN       450
AANNTNTTTT AAACNNACAA CCCCNTAAAG GCCCGNNGGT NTCNCCGGT       500
TTTCCCNTTT TCTTGGNCGC TTTCCNCCCC CCCTNNAAAT TGNTAGTTTA      550
TTANNCAACN ANGTTNGNTT TCANAGNNCA AAGTCAAGCC CTTTCCANNT      600
TGTTTTGGNN GGCAANTTTC GGCANTANTT TTTNGGTNTT NGANGGNCTT      650
TTNANAACCN NNGGGGNCGG TTTTNTAAAA TTTANNNCNN TTTCCCCNAN      700
TTCNTTATTT CTNCCCNCCC GGGGNNCCCC NCCN       SEQ ID NO. 68  734
```

FIG. 2

Plasmid: 3B11 T3

```
GAATTCAGCT TGTCGTAATC TCTGTATATA TGCGAGTTGG CCGGGTATCC       50
ATGACGTTGA TTTGCGTGGT TTGTGGTTAC TGATCGGCTG TTTTAGTGA       99
SEQ ID NO. 69
```

FIG. 3

Plasmid: 3B12 T3
Accession #: U27476

```
CNNCNTTNNN NGACACAAGC TGGAGCTCCA CCNCGGTGGC GGCCGCTCTA       50
GAACTAGTGG ATCCCCCGGG CTGCAGGAAT TCGAAGTGTT GACCAGCGTG      100
ACTGTAGCTA CAGTGCCCGG TAGCCAAATT ACAGGACGCG TGATGAGCCC      150
TAGCTGCGCC ATGTGGCGGG TTCCCACTAC GAGGGCGCAA GTGCTGGGGG      200
CTTGAATAAA GGCGGTGTCA AGGTACACCG TGTGGGTGTA ATTGGGTTGG      250
ATGATAATCC GTTGCTGCAC ACGTAGGGAG AAGAAGTGGT TTTCGTTTGG      300
GGGTGACATG TTCATGAGTT GCCAGGGCTC GGGACGGAAA CAGGGGAAGA      350
TGCAGATGTC GCCCTCGATG GTGCCCGGNG TGATGGCTTG GAACGTGTAG      400
TTAAGATTAA TAACTTCCAT GCTGAGGTTT CGTAAGCCGG GTTCGATGAA      450
TTCTGGCATG NAACAATTTG AGAATCCAAA CATTTATTAA AACGTAATTC      500
CGAAGTNTCC NATGGATTN TAAGGTTGAT GCCNAGGGTG TTGAAGTNTT       550
GGNTGGTCCG GTAGCAATAT GTTTGGTGGA ATTNATGCTT TCTTGGTTGN      600
GAAAATTGAG GGTCCCTTTC GGATTTNGGC NNGNNAATTT CCNCN   SEQ    645
ID NO. 70
```

FIG. 4

Plasmid: 3B12 T3

```
GAATTCGAAT TGTTGACCAG CGTGACTGTA GCTACAGTTC CCGGTAGCCA    50
AATTACAGGA CTCGTGATGA GCCCTAGCTG CGCCATGTGC GGTTCCCACT   100
ACAGGGCGCA AGTTCTGGGG GCTTGAATAA AGGCGGTGTC AAGGTACACC   150
GTGTGGGTGT AATTGGGTTG GATGATAATC CGTTTGCTGC ACACTAGGGA   200
GAAGAAGTT    SEQ ID NO. 71                               209
```

FIG. 5

Plasmid: 3B12 T7
Accesson #: U27874

```
GAATTCCTAG CCAGCTGTAT GTCCAAAATA CAACCGCGCA ACCACTCTGC    50
TCATGTACCC TGGTGCGGTT GAACTAGCTA ACAGAACTTT AAAAACTAAC   100
GGAGACATCT CCAGCGTCCT CACCGTAGCT CGGCTGGTTT ATGTGTTAGT   150
TAAGCAAAAC CGTCAAGACC TGGTTACGCA CACCGCCATG CAACACGTCC   200
GTGACCTCAT NNTGCGTCTC CATAAATCAC ATATAGCTTC TTTCCTATCA   250
CGGTTTGCTC GCCAGGAACT GTATCTTGCC AGCAGCATTA TTCATTCCAT   300
GCTAAATTAC TCTACCGAAA GACGAGACAT ATTTGTCTTC GAAACAGGAT   350
GTGTTCACTA GCTGAACTCT CACACTGGTC ACAACTCATC GGNGGCCACG   400
AAAACGTCAC ATCAGCGATT TNTCAGTCCA TGCGTTGGAG NGGGGNAGAG   450
ACACGCCTAG ACACTNTNTA CATGTTNCAA AGNACTATCT GGACCTAAAA   500
TGTCTTTTTT TAGACTTAGC AAAATTTCAT CCAGATAATN TCCAGGGAAT   550
TNGGCGTTAA AGTCCNTGAA                SEQ ID NO. 72      570
```

FIG. 6

Plasmid: 3B13 T3
Accession 1: U27610

```
GAATTCCATC CCCCCGATGA ATTTGCGGCG ACTGGCGGCG TGCCGCTGAG    50
CCGCCAGCTG TTTGTGCCGG TGGTGTTCCT GAGCGGCCTG GCGCAGGGTG   100
TTGCCGGTAA AATCAAAAGC GCTGCCCTGC TTCTCTCGAC GCCACAATTG   150
TCCATATCGA ACGAACATGA GTCTAGAAAT GATACACACG TACCGCTTTA   200
GGCGATCGCC GCTCGAGTCC CGGCGAACTA CGCTATGCGT TCGCGCCACC   250
AGGGACGACG ACGCACCGGG AACACCACCG CAGTGGNGAG AGGAGGCAGG   300
AGGGGGATGA TTTTTGTTTA TAGGCTCGGC CTTANCGATT TCATAGTACA   350
CATAGAATAA ATTACGNCAG ACGGTGTCAT GCTCGCCGAA AGCCAGACTC   400
AAGCGCCGGT ANANAGTATT TTCCNTACA AAACCGNTTG GTNTTGGCGT    450
AGGTGATGNN AGNTTAAGTC AANATTGGNG TTAAACGCCA GGTAAGTNAT   500
GAATGAANGT GGTCCGAGGA ANGCACATAG NTCCANCCT TAATCCGNGA    550
GAGGTCAAAN CCT                       SEQ ID NO. 73      563
```

FIG. 7

Plasmid: 3B13 T7
Accession 1: U27875

```
GAATTCGTAC AATCTCACCC AAGAGTTGTC GTTAGTGGAG GACGCTCGGT       50
TTTGCCAGAC GCGGCCCGTG AACGCCGAGC GCGTTCGCGG TGTCTTCGGC      100
GCGCTCTATC GCGCCGCGTC CCCGCACATG CGGGAGGAGA GTGACCGCAT      150
CAAGCTGATT TTGGGACGCT TGTTGCTGGG ACCCGTGGCC GTGCCCTGCT      200
ACTGTGACGA ATGGGAGGCG AATGACTACA TGGTGGAGGC GGCGCAGTTT      250
TGCACCGGCC CCCTGCTGTA TGTGNACCGA CGCTGCCACT GTCCCGGTAT      300
GGGGGGCGCG CTCGCTTTCA CCGTGATGGA AGGGCATNTC GCGACGCATN      350
TTTTTAGAGG GNTGCTGTCA CTCACTGAGT GGAACCAGNA CTGCCCCACA      400
TTTTTTGGCC NTGCNAACG GTGANCAGNG GGATCGGACA NGAATNGCTG       450
TCTNCCCGNN AACTTACGTT TTNTNTAAGG AATATCCTAA TTATGGGGAG      500
ACGGGTTTCT CACCNATAGG GTTATAGTAT NTATACAATC TGGGANCCNA      550
NCCCCNCTAA TTAAAAAATT TNGTGGGTA   SEQ ID NO. 74             579
```

FIG. 8

Plasmid: 3B412 T7
Accession #: U27888

```
GAATTCACGT GTACGGGGAC ATTGACGACC TGGGGTTCCG CCGCCGACTC       50
CACTATTAGA GCGTCCTGGG GCGCGCGACA CTGAAAGACG GTTGGCGAGG      100
AAGCCATCGC CGCACGCCGT CATGGAAAAC TGGACGGCAG TCGAGTTACT      150
CCCGAAAGTC GGGATCCCGG CCGACTTTCT CACGCATGTA AAACCAGCG       200
CCGGGGAAGA AATGTTCGAC AGTCTGCGCA TTTACTACGG AGATGACCCG      250
GAACGCTACA ACATCCACTT CGAAGCCATC TTCGGCACCT TCTNCAATCG      300
TCTCGAATGG GTTTACTTCC TCCAGACGGA CCTGGCATCG GCNGCGNACG      350
CCATCAAGTT CGATGACCTG AACAAGATGA CAACAGGGAA AATGGTTGTT      400
TCACATCCAG NTTGCCGCGT AACAAGATGA CAACAGGGAA AATGGTTGTT      400
CAGACACCAC ATNGTTACCA ATNCAGTAAA AAGCCCCTCA CCNCCCCTC       500
NCCTCANGGC CCCTTTTATG ACCTGGAAAN NTCNGACNCA ACCCGANGTC      550
NTATTTCGAG CNNGAAACCA CTTNNTNTTN NAAANC       SEQ ID NO. 75 586
```

FIG. 9

Plasmid: 3B413 T3
Accession #: U27622

```
GAATTCTGTA ATCCATGCCA CTTGATTGCG ATACGTTTCA TGCAAGCTGG       50
GTTGCAACTG TTCTTAATCT CGATTGGCCG TCGCGGGCTT CCACTCTCAT      100
TGAAGATGAT TCCGAACGGG TAAAGCGTCA GAAAAAGAG CTGGTGCGGA       150
TGTTTGATGA GGCGTCGGAG CATGGCATCA ATGCCATGAT TTTTCAGGTC      200
TCTCCTGCTG CCGATGCTTT CTATAAATCG GAGTATCTGC CGTGGTCGTC      250
TTATCTCACG GGTACGCTCG GAAAAGATCC GGGCTTCGAT CCACTNCGCT      300
TTGCAATTGC GGAAGCGCAT AAGCGCGGGA TCGAGCTGCA TGCATGGCTC      350
AATCCTTATC GCGTTTCGAT GGATGTGCGA CCAGCAACGC GGAAAGNACT      400
GAAAAAACTC TGCCGGCGAT TCTCCGNCCA GCGTCTATAA AACCAATCCA      450
GGCTGGGTNG NTTATNTCTG CGGATCCNTT ATGTGTTGGA TCCGGGTNTC      500
CCGGATGTTG NCAGTGGNTG AGAATTTAAG GCCGAAGCCG TCANAATTTA      550
TGTCGAGGAT CAGTCC                SEQ ID NO. 76              566
```

FIG. 10

Plasmid: 3B413 T7
Accession #: U27888

```
GAATTCATTC ATCTTCATGG GGNAGNAGAA AAATGAACAT CAGGACCAGC       50
TTCCACATTG ACACCATGGC TGTCACCATG CTCTTTTTCA ACGGGCTGTT      100
CAACCTTAAC ATCTTTCGAG ACGTAGTGGC CGATGACTCA CAACAAAAAA      150
GTTGTGATTA TATGAAACAA CAACACTTTT TNCGCACGAT GGGTATAGCC      200
TCTGTGTTTC TCAGACCCGT CTTTAGTCCT ATCATTTACA TATGTGTCAG      250
TCGNAAAATC ATACAGGGTA TCTGCAAATT GTTTATAAAA GTACCAAACC      300
ATACCATAAG CTCGGAACGT GTAAAGCTTA TGTCTCCAAA TAGAATGAAC      350
GACGATGCCC CAGAGCTTCC GCCCAGGGGA ATATGAATCC GCGTTCTANA      400
TTATTGCGCG TTGGTAGGGN AACGACACAA CCAGCCGATT TNTGTTTGGG      450
ACCGGTCACA ANCCCCCGAC ATTGGAAATC GACATTGTTC GGTTGGNGAA      500
CAGNCTTTTT ANAACATGAA CAACTCCCCC GTACCCTCTG AAGTGTTAAG      550
ACGCGAGNAT TCGGAGTAGG                                      570
                                       SEQ ID NO. 77
```

FIG. 11

SEQUENCE LISTING ( 1 ) GENERAL INFORMATION:

( i i i ) NUMBER OF SEQUENCES: 104

( 2 ) INFORMATION FOR SEQ ID NO:1:

( i ) SEQUENCE CHARACTERISTICS:
        ( A ) LENGTH: 1485 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GATGAGCTGA  CAACGCGTCC  ATCGGAACAT  GACAGCACGG  AAACTACCCC  TATCTTGTCC    60

GCCTCGCACA  AACCCAGCAC  GAACACACCC  CCGGCTGTCT  CACCTAAGCC  AACCATCTCC   120

AACGGCACCA  AAAAGCCCAT  TGTTCCACCA  AAACCTAAAC  CGAAGCCAAA  GCCGACGATG   180

CTCCAGTTCC  CCGCACCCAA  AAGCGCCAGA  CCACGCCCAA  GAACACTCAA  AGTCCCAAAG   240

TGTTTACTTT  TAACGAGCGT  GACATAAGAA  AGCACAAAGA  AGAGATGGGC  GCGGAGGCCA   300

CGAAACCTAG  AATCATCCAT  CACACAGAAG  ACAGAACCAC  CGTTGACAGC  GTCCTAACGC   360

CGCTACTGCC  ACCTCCACCG  CCAGCTCCCC  GACGGTATCA  ACATCGCGGG  TGCCAGTGAT   420

GATTCCCTGG  GACAACACGC  AATCTCCCGC  GAAGATGAGT  CCCTGGAAAG  ACACTTGCGA   480

ATCCCTGCCC  ACGGAGCTGG  ACCCTTGGGA  GTTAGGCCC   CGCCGTGGTT  GTAGTAAAAA   540

GAACTTGGAC  TGTCAATCAA  ACTGCAGATT  GTATAGCTAT  TTAAACTTTA  TTTCTGTATA   600

TATGTGTAAA  TAATAAATTT  ATTCCTCGTA  TCACACATCT  GCATCCTGGT  CATTCACATC   660

TAGTATTCGC  AGCGCAATTC  GGGGCCCGGG  AGGGTGCATC  ATGGCGTCCG  GGGCTATCTC   720
```

-continued

| | | | | | | |
|---|---|---|---|---|---|---|
| TTCCATGATT | AAGATAATCT | CATCTCCCAA | CGGAGGCCTG | TTTTCCTGGT | CCTCAGCCTG | 780 |
| TATTTCCATA | GCGATCTCTA | CCACCTCAGC | CACCTCGGGA | GGAAACTGCA | ACGGCTGGAT | 840 |
| CTGCAGTTGA | AGCTGCTGTC | GTTGCAGATA | GTTCTGAAAC | AGTCTCCGCC | GAGCCCGAGG | 900 |
| AGCATACATG | CCTAGAGGGC | GATGGGCAGG | TTGGTTTAAA | CGATAAAACG | AAGCCCGGAT | 960 |
| AGAAGGCATG | AGACCGCGGA | CGGCCTCTGA | TAAGAGGGGA | TCGGTGCTGC | CTCCCATAGT | 1020 |
| GCCAGTAAGA | TTCTGGGAGA | GTAGACATTC | CTAAATACTA | GCCTGGATCT | GACGTCAACA | 1080 |
| CTATGATTCA | CGCCCAATTC | CACCCACAAA | GCCCGTTAGA | ATACCAGACA | ACGTCCCCGT | 1140 |
| TAGTGATGCC | ACCCACACAA | GATATTTAAT | GATAACAGAG | TTTCAGACCG | CCTTTGTTGA | 1200 |
| ATCGATTCCA | ATACCGGCAT | CATGAGGAAT | CTACAGCTGA | TCGCAACTTT | GCTAGTTATC | 1260 |
| GGTTTGGTGG | CAGTTCATGC | CATCCCCAGG | TTGGAATATG | TAACCATATA | TATCGCGCCC | 1320 |
| TAGTTATAAC | CATATTTGAC | CTGAAATACT | AATGATTCTT | TCCTCTCACA | TGTGCAGGAG | 1380 |
| AACCACAGAT | GATAATAAAA | AGACAACAAA | CTCAGACTTA | AGCAACCAGA | CCGACGGTGG | 1440 |
| CGCTGGCTTC | GGCAGCACAT | ACGATGGACG | CGTTGTCAGC | TCATC | | 1485 |

( 2 ) INFORMATION FOR SEQ ID NO:2:

( i ) SEQUENCE CHARACTERISTICS:
        ( A ) LENGTH: 1540 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

| | | | | | | |
|---|---|---|---|---|---|---|
| GATGAGCTGA | CAACGCGTCC | ATCGGCCAGA | TACATAAGTT | TACACTCACT | GGTACTTGTC | 60 |
| ACTCACTTGA | TCACTTTGCT | GCGGACGTGA | CGGCCAATCG | TTTCGGGCAG | GAGTGGCCAA | 120 |
| ACGGCATTAT | AACGAAACGC | CGACCGGGGC | CACACGCCAC | TTGGAAACGC | CGCCGTTAGT | 180 |
| CCTTTTTTCA | ACGGTACGAT | ATCGGCAATC | CCCATGACTA | TGAACATAAT | TATAACCACC | 240 |
| CGCGAATTCT | CCAATGACGA | ATCCGTCACA | GAGAGCACGG | AACCGCAAGA | CAACGTTGCC | 300 |
| AATAACCTTT | CTAAAGCTTA | CCGAGGTACG | ATTCGCGCGG | AAGGTAAGAA | GAAACTGCTT | 360 |
| ATTCGCAACC | TGCCTGCCAC | TTTCGGCTGC | ACTCGCCGCA | ACAGTAATTT | ATTTATATTT | 420 |
| TATAACGACC | GGGACTATCG | AAAGTTCCAT | CAAGGCATCA | TACAGTTAAA | ACGAACTCGC | 480 |
| ACGCGAGTTG | ATTCATCACA | GATCGTGAAC | GTTACAAAAA | ATATAAAGTC | TCGACTGCAA | 540 |
| CCGCACAACT | CAAGACCCGC | CGCTAGCCGG | CGGGCAGATC | CAAACCACCA | TCTCGCACGT | 600 |
| CTGCACTCTG | TTCAATCACC | TCGTGTTCAC | GGCTCAGCTC | CGTCATTATT | GCGAAACTCA | 660 |
| CGAACAAGTT | GTCTTGTACG | CAAGGGACGA | GCTCACCAAA | CGTTGCGGAG | ACAAGTCGGC | 720 |
| GCTCGGGACT | CACACTCACC | GACTCATTCC | GCTCTTGGAT | CACGACAACC | ATCGCGAACT | 780 |
| GTGCAATGTG | CTGGTCGGCC | TGCTACACCA | AACACCCCAC | ATCTGGGCCC | GTTCCATCCG | 840 |
| TCTTATCGGC | CGATTAAGAA | ACTATCTACA | ACAGAAGTTT | CTCAATATCT | TGGTGGATAG | 900 |
| CGGACTCCAG | ATCGATAGTC | TTTTTGAGGC | TTGTTACCAC | AGCGAACGGT | ACCGCTTGCT | 960 |
| GTTCCAGATC | GAAAAAACGA | ACTCCACCCC | TAGCTCTCTA | GCCTGTGCAA | GCACCGTTTT | 1020 |
| ACCTGTCGGT | GAAAACGAAA | CTGAAGGCAC | ACCTGTCCCG | CCGTGTATTT | AATGAAATAA | 1080 |
| TAAAATGGTT | CTCATGAATA | AGACGGTCTT | AGTTTCGTTT | TTGAAAGGAC | AAGTATGAGT | 1140 |
| GTCCCCCAC | ACATCCCCGC | CTTGGCCGTG | GACTCGAGCC | TGAACTTTCG | TGCGCACCTG | 1200 |
| TTTTCTGACC | ACAACCGACA | CTTTCTAGTC | GATTTAGTAA | CCCAAAGCTG | CAGCGGCTAT | 1260 |
| GTGGGACTGT | GTAACGCCGG | AATTCCCATC | CCCACCTATG | TACTGGAAAC | GCTAATTGAC | 1320 |

|  |  |  |  |  |  |
|---|---|---|---|---|---|
| TTTCAGGTTC | CAACCACATA | CACGAAAATT | AAGCCCATTG | CCGTAAAAGT | GCTAAAAATC | 1380 |
| TGTATTCTGG | CTAACTACCT | AAAAAACAGT | AAGAATTAT | GGATTGATTT | CAAAGCTAAC | 1440 |
| CTAGACGAGA | TTAATTCTGG | TGCAAATAAG | CAAAGACTGT | ACAGAGGCTT | TTACAAACTA | 1500 |
| TGTCGTGATA | AAAACTCGAT | GCACGCGTTG | TCAGCTCATC |  |  | 1540 |

( 2 ) INFORMATION FOR SEQ ID NO:3:

( i ) SEQUENCE CHARACTERISTICS:
        ( A ) LENGTH: 1554 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

| | | | | | | |
|---|---|---|---|---|---|---|
| GTGGCGCCCC | GGCTTCATTA | TAACGCCACG | TCGGAGCCCC | TGCGCCAC | AACGCCGTCC | 60 |
| GGCGCAACTT | CTGTCTCGGC | ACGGTACGAT | AAAAACAACG | TCCCCGTCG | ACGTTGTTTT | 120 |
| CTCCGAGCGG | TGATCGTTCC | CGTCCTCTC | CTCCCTCCGC | GGCCCCACG | GCGGCGGCCT | 180 |
| GCTCGCACGG | ACCTATACTA | TTACCGCCCG | ACCGCCGTCG | TCGTCATGAA | CTTCATCATC | 240 |
| ACCACCCGAG | ACTTCTTCAA | CGACGATTCA | GTCCTGCGAG | CCGCCGAGAT | GCGTGACAAC | 300 |
| GTGGCAGGCT | CGATTTCCAA | AGCTTACCGA | GGTACGATTC | GCGCGGAAGG | TAAGAAGAAG | 360 |
| CTGCTGCTGA | AGCACTTGCC | CGTGCCGCCC | GGCGGCTGCT | CGCCGCCAA | CAGCAACCTC | 420 |
| TTCGTTTTCT | GCACCGAGCG | CGACTACCGC | AAGTTCCACC | AGGGCATCGC | ACAGCTCAAG | 480 |
| CGCGCGCCGG | CCGAACTGGA | CCGCCACGAG | ATCCAGCAAG | TCACGGCCAG | TATCCGCTGC | 540 |
| CGCCTGCAGC | CCAGTCTCCG | CGAGCCGCCC | ACGCCGGCCG | ACGAGCTGCA | GACGGCTGTG | 600 |
| TCGCGCGTGT | GCGCGCTCTT | GAACCAGCTG | GTTTTCACGG | CCCAGCTGCG | CCACTACTGC | 660 |
| AGACACCAGG | ACAAGGTGGT | GAGCTACGCG | CGCGACGAGC | TGACTAAACG | CTGCGGCGAA | 720 |
| AAATCGGCGC | TGGGCGTGGA | AGTGCATCAA | CTGGTAGCCC | TGCTGCCACA | CGAGCGCCAC | 780 |
| CGCGAACTGT | GCCACGTCCT | CATCGGCTTG | TTGCACCAGA | CGCCGCACAT | GTGGGCGCGC | 840 |
| TCCATCCGTC | TCATCGGACA | CCTGCGCCAC | TACCTCCAGA | ACAGCTTCCT | ACACCTGTTC | 900 |
| ATCAACTCAG | GTTTGGATAT | CGCACAAGTT | TTCGACGGCT | GTTACCACAG | CGAGGCCTAC | 960 |
| CGCATGCTCT | TCCAGATCGG | TCATACGGAC | TCGGTGTCGG | CGGCCCTGGA | ACTCTCACAC | 1020 |
| GGCGCGGCGG | CCGGGCCGCC | CGAGGCCGAT | GAAAACAACG | ACGAGGGAGA | GGAGGACGAC | 1080 |
| GACGAGCTCC | GTCACAGCGA | CCCGGCGCCG | CTTCACGAGT | CCAAGAAGCC | CCGCAACGCC | 1140 |
| CGTCGTCCCC | GCACACGCGT | CCCGCCTCAC | GAGCAAAAGC | CCGAAGAAAA | CGACCAGCAA | 1200 |
| GAAGACGACC | TGTTTCCCTC | CTGCAAGGCA | ACCGCACCAT | TCCTGCGCCC | AGAACCCTCC | 1260 |
| GTCTCCAACG | ACGACGGCAA | CGGCGGCGAA | CGCTGCGACA | CGCTAGCGAC | CGCCCTGCGG | 1320 |
| CATCGCGCCG | ACGAAGAAGA | CGGACCTCTA | GCCAGCCAGA | CCGCTGTGCG | GGTCGCCGCG | 1380 |
| ACCCCCTCAC | CTTCAGTCAC | CCCAGCCCTT | ACCCCCGTCA | CGTCCCCCAT | AACCCCGTTG | 1440 |
| TGTATTTAAC | GTCACTGGAG | GACAATAAAG | CGTTGATTTC | TCAACTTCCG | CTCTGGTTTT | 1500 |
| GGTTTCGTTT | TCAAAGGGAG | CCCCATCATG | GCCCAACGAT | CGCGAGCCCC | ATCC | 1554 |

( 2 ) INFORMATION FOR SEQ ID NO:4:

( i ) SEQUENCE CHARACTERISTICS:
        ( A ) LENGTH: 666 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

| | | | | | | |
|---|---|---|---|---|---|---|
| GGAATTCGAT | CGGATACCCC | GTCTACGTGT | ATTAATATTA | CATAAAATAG | GCTTTTTTTT | 60 |
| AAAAAAAGA | AAAGACATTT | TTCACTAATG | GTGTCATATC | ATTATAATAA | ACCTTGTTTT | 120 |
| CATCAGGAAG | GTATAAAAAC | AAATTCATAT | GCACTAAATA | ATATAGATTC | AAAACAAATA | 180 |
| AGGCAAAAAT | CAATGGCAAC | AGAATAAGCA | TATATATAAA | CATGGTGAAA | AATTACATAT | 240 |
| AAACACCAAG | AATGTGGAAG | ATTTAGCTGT | GATTAGCAAA | TTTTGCCTAA | TGGATATATA | 300 |
| TGTATAAACT | TGTCCCAATA | TCTACAGAGT | ACTCATTCCT | ATCAAACACA | AATAAAACAG | 360 |
| TTCTTAAAAA | TTCAGTACAT | ATTGTGTCAA | TTTTAAAAAT | AAGCTTCAAA | GTTTGATAC | 420 |
| TATAATTTAG | AAACTATCTC | GAGGGAAATA | ATATAAATAG | TTAAATAAA | AGTGAGGTGA | 480 |
| AACTAATGTA | TATTTAGATG | AAGCAGTATA | GTTTAAATT | TACATATTAT | AAAAGAAGAA | 540 |
| TATTAATGAA | CTAAACATAC | ATCCTAAGAA | GTTAGAAATA | GAATAGCAAA | ATAAACTCAA | 600 |
| AGAAAGCATA | AAAAAGAAA | CTGGTGGAAC | GGGAAACACA | CGTAGACGGG | GTATCCGATC | 660 |
| AAGCTT | | | | | | 666 |

( 2 ) INFORMATION FOR SEQ ID NO:5:

( i ) SEQUENCE CHARACTERISTICS:
        ( A ) LENGTH: 517 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

| | | | | | | |
|---|---|---|---|---|---|---|
| TATCGATAAG | CTTGATTTCG | CGTTGCTAGG | CCACCACTAA | TGCATGATTT | TTCTTTCAAA | 60 |
| TATACCAACA | CATAAAATAC | GATAGTAGCC | ACACAGCAAC | AAATAATGAA | ATCATGTACC | 120 |
| GAAGAGGTTC | AGGTCCAGTT | AAAAATAGAA | AAGTATGAAT | AAAGTGCCTC | CATCCCTTAG | 180 |
| GGAATTCGAT | TTCGCGTTGC | TAGGCCACCG | CTTTGTTTTT | TGCAATCTCC | TACGGTAAAA | 240 |
| GTAATACAAG | GGAATGGAGA | GCCGCCGCTC | GATACGCACT | AGCACTGCAA | TTGGAAATTC | 300 |
| GATCCAAAGA | AGAACCGTGG | ACGCCACTTG | AACCTCGCAT | ATTTCAGCGC | GTGTATTTGG | 360 |
| AACACGACAC | GACTTCCCAA | CTCAACAATG | ATCAACTACA | TGTCAGCGGA | ACTGTGATTG | 420 |
| GAAATTTTAC | AAATACAGCT | TGGATGCATG | TTAGTCTGAG | TTATCCTAAG | TTCAAGGAAA | 480 |
| TGTTCGTCAT | GTCTACCAAC | CCAGACATCA | CAGTGAA | | | 517 |

( 2 ) INFORMATION FOR SEQ ID NO:6:

( i ) SEQUENCE CHARACTERISTICS:
        ( A ) LENGTH: 567 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

| | | | | | | |
|---|---|---|---|---|---|---|
| AAGCTTGATC | GGATACCCCG | TCTACGTGTA | ACACCTGGAA | AGTTAATGTT | CAGTGAAGCG | 60 |
| CCCCAATGTC | GCTGAATCCA | CCCAGCTCCT | CACCTGCAAG | TTGGCCAACA | TGATGTGTCA | 120 |
| AGTTGGGGAC | ATGAATGCTT | GTCCCACCTG | CCCTGGGAGA | AAAGATCATA | GAAGTGAAAT | 180 |
| GACCTTGTAA | ACAGCAAAGT | CCTGTGCAAA | TATAATGGTC | CTTGTTGAGT | CTTTTCCACA | 240 |
| TTCATAATCG | ATGTTTGTCT | GACGCTGACC | CCTGCTCCAG | AACCACCCCC | CCCACTCCCC | 300 |
| GGTCTGCTGT | CGGGGAGCGC | CAGGACACAC | TTGGCTCTTG | GGCAGTTTTA | AGTAGGTTTA | 360 |
| ACGTTCTCAC | ACTGATAGAA | GTGGTGTACT | TTAAAGATGA | ATTAAAATGA | ATACTTTATT | 420 |

| | | | | | |
|---|---|---|---|---|---|
| AGTAACTCAG | CTGTGCTTAC | TGCTAGATTC | CTTAAAATAA | TGCCCCTGCC | TTTCCCACAA | 480
| TGACAGGGCT | TGAATTTCTT | TTTTTGCGAA | GTGTGGTGGT | GAGTCACAAT | CATTTCCGAT | 540
| GGACGCGTTG | TCAGCTCATC | GAATTCC | | | 567

( 2 ) INFORMATION FOR SEQ ID NO:7:

( i ) SEQUENCE CHARACTERISTICS:
        ( A ) LENGTH: 160 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

| | | | | | |
|---|---|---|---|---|---|
| GAATTCTGGT | ATGAGACGGA | CGGCACGCCG | GTTCAATCCC | GGAAATTATT | ACAATGTCGG | 60
| CGGCAATTCC | AAATTCTATG | GCGCAGTGCT | GGTGCGCTAT | CGGCGAAGAT | TTGAGGAGC | 120
| TTGCGCATCT | TGAAGGCGTG | TCTCCGGCAT | GGCCTTTTGG | | | 160

( 2 ) INFORMATION FOR SEQ ID NO:8:

( i ) SEQUENCE CHARACTERISTICS:
        ( A ) LENGTH: 784 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
            " N"represents any base.

( x i ) SEQUENCE DESCRIPTION: SEQ ID NO:8:

| | | | | | |
|---|---|---|---|---|---|
| TANGTACACN | CNCTNGAGCT | CTCGCTNTCT | AGTAACAAAG | GCTCAGTACG | TGGNAAGGGG | 60
| TGTNGCGTCA | CGCCTACACA | CCTGGGCTGC | TCGACCATCA | TAACGTGTGT | GATCTGGAGG | 120
| GGCTTCTAN | ACCTGTCGTN | GNTGNGGACC | CCNCAGNTTT | NTATCNGTAG | CATACTNACN | 180
| NAACGCTCTA | CCNCNTCNAC | ATTGANNCN | TTCCTATTTT | TTTCCCCCA | CACTTTTTNT | 240
| TTTTCANTTT | ACCTCTNANC | TANTTTCCNA | CATTCTNCNN | NNNNCATNTC | TNCATCCCCC | 300
| ACTAATNTTC | TTCANTCNNT | TATNNATCAA | NCCNCNNTCN | CACNTTNCCA | TTNCAACCAC | 360
| CNANNNTNTT | ANCTCNCTTA | NNNTTTCTCC | TTNNNACTAT | CAATCTTNTN | TNACTNNACA | 420
| CCNANCACTC | NAANCTCCAT | TTTTAAANNN | TNNANNTNTC | NTNNCCNTTN | TNTAACCCNC | 480
| TTNANCNTAC | NTCNNTAATT | NCTTTTCCNA | ANATTNANNC | CNCACCNANT | TATNNNTCAC | 540
| CANNCAACAT | NTNNTATNTC | TANNNNANNN | TTNTTTNNCN | TAAACNTCCT | ACTTCTANNT | 600
| NTNCANNTAA | TANAATNCTA | NACTNCTCAC | CTTNAACNNC | TNCACTNCAN | ACNTNACNNN | 660
| NTCNNNTTTT | AAACTNCNNT | NNTNNNTTTT | TANATCCCNT | CTCACTTNAT | CTNATAANNC | 720
| NNATCCATNT | TTGNCCNCTC | ATCTATCNTA | CTNNNNACNC | NTNNCTNCCN | TCTTNCTCAT | 780
| CCAA | | | | | | 784

( 2 ) INFORMATION FOR SEQ ID NO:9:

( i ) SEQUENCE CHARACTERISTICS:
        ( A ) LENGTH: 680 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
            " N"represents any base.

( x i ) SEQUENCE DESCRIPTION: SEQ ID NO:9:

| | | | | | | |
|---|---|---|---|---|---|---|
| TGTTTTNCAN | CTTCTCAAGG | GACCCCCCCC | CGAGGAAGAC | GGTATCGATA | AGCTTGATAT | 60 |
| CGAATGCCCT | GCAGNCCGGG | GGNATCCACT | AGTTCTAGAG | CGGNCGCCAC | CGNGGTGGAG | 120 |
| CTCGAGACAG | GTGNCGCGAT | ATGCCNCGGC | CTGGCACCGC | GAACACAGCG | GCCCTGGCC | 180 |
| GTGACACGTG | AGCTTCAGGA | GTCGCGGGAT | AGTGACGGAG | CGCACCACCA | CGGTGGAATC | 240 |
| GCACGTCCGC | GCAGAGCACG | GTAGAATGAT | GTCAAACGTG | ACGAGGTGGT | CATAGACCGC | 300 |
| ACACGCGGTG | TTCANCCCCA | AGACTGNCTT | CCAACCAAAC | CGNAAACAAC | GTTGCCCACA | 360 |
| NATCGTCTCA | GAGACANCTT | CGTAAACACG | TTCTTTTAAT | GACACGCTGA | CTTCCACAAA | 420 |
| AGAGAACAGT | GCANCAGTTC | GGCGTTAGTA | TTGAAANTGA | CACTCTTTTC | TTGGCGGTCT | 480 |
| CTATANTAGA | ACATAGAGTT | AAGGGGGGAA | TTCTGCTCGC | AGNGNAGGTT | CTCCTGGCCA | 540 |
| AGTTCAAGCA | GGGGNCGAAT | TTCGGANAAC | ACGGNGACAG | GATCTTGGTT | TAGTGGNGTC | 600 |
| NACTCAGNGA | AAAGCACAGG | NGGTTTATAC | GTTCTTTNTC | CCGAGNCNCC | ATCTATATTT | 660 |
| GGTGTCNGGC | CCNTTTTTTT | | | | | 680 |

( 2 ) INFORMATION FOR SEQ ID NO:10:

( i ) SEQUENCE CHARACTERISTICS:
    ( A ) LENGTH: 521 base pairs
    ( B ) TYPE: nucleic acid
    ( C ) STRANDEDNESS: single
    ( D ) TOPOLOGY: linear ( i x ) FEATURE:
    ( D ) OTHER INFORMATION:
      " N"represents any base.

( x i ) SEQUENCE DESCRIPTION: SEQ ID NO:10:

| | | | | | | |
|---|---|---|---|---|---|---|
| GAGCTCGCCT | CTGGCTGCAC | CTGTGGGGGG | CTCTTTCCAT | GTCCTCACAC | GTCTCTGTCA | 60 |
| CGTCCGCCCT | CGTACAGNAT | CACCGCTCTC | CTAGCTTTCC | CAATTTGNG | GTCAAACACG | 120 |
| TCACAATTAC | ACTGCGTCAA | CCACCTGCCC | GCGAGCCATT | CACACGGTAC | TTATGAGAGC | 180 |
| GACAGGTAGN | CCCTTGNCAG | TCCCGTCAGT | CTTGCCCCAA | TAGAAGCCAT | CACAGACACT | 240 |
| GTCCATCACA | GNCCATCTAA | ATTACANCAT | NACATTATTC | ACACCGAGAC | GANCNANNNG | 300 |
| GCTCGTNGTG | ATGATCGAAN | TTTGNGATCG | CNACTGCGGT | GANCAGTTGC | AGATCGAACG | 360 |
| GNTGAGGACG | TCGTNGTAGA | CAGGAGTNTC | GNCAGNGCAA | ANCTTACTGN | TNGGCANCGG | 420 |
| CCGANTGANG | CCGANAGCCA | NAGACCGACG | TCTCGANTCA | ATTCAAACAA | AGACGTCCGG | 480 |
| TAGCAGGGTC | CGTAAATAGG | GCTGCGTTAA | AACNCNTGNC | G | | 521 |

( 2 ) INFORMATION FOR SEQ ID NO:11:

( i ) SEQUENCE CHARACTERISTICS:
    ( A ) LENGTH: 514 base pairs
    ( B ) TYPE: nucleic acid
    ( C ) STRANDEDNESS: single
    ( D ) TOPOLOGY: linear ( i x ) FEATURE:
    ( D ) OTHER INFORMATION:
      " N"represents any base.

( x i ) SEQUENCE DESCRIPTION: SEQ ID NO:11:

| | | | | | | |
|---|---|---|---|---|---|---|
| GAGCTCCATC | TGTGTGACGT | TAATCTCCAA | ACACCCTTCA | AAGAAATGCA | CGAACAGTTA | 60 |
| AGTTACCTGA | TTACAGGACA | CACCTCAACC | ANCTCCATGT | CCTTTTCCGA | CGAGCTGCTT | 120 |
| CAACTACGCT | CACAGTTCAC | GTACGCTACT | CAGGTAAAGG | AAGACACCGA | AAGCAAAATC | 180 |

| CATGACCTGA | TGCTCAACAT | CGAAACCGNC | ATCCAGGAAC | CTACCACCCG | CAGCTCCAAT | 240 |
| ATCGNCATGG | NCATGGTCCA | AGAACAGCTA | AANGAACTTC | AACAGCTCGG | AGGNGCCANC | 300 |
| ATCCCTGAAA | TAGCTACCCG | TCTGGAAAAG | GTACACAAGG | TGTTGAATTC | CCTCCAACAN | 360 |
| GAAGNACAGG | GGGGCAGAGT | CTTCGTCAAC | GGGCTAAATT | ATGACACTTA | CCAANCGATC | 420 |
| AANCACTCAN | NAGACANGCG | GGCTTTCAGA | CTGNTGGGGA | GGNGGCAGCT | CACGAATTTC | 480 |
| ATCCAGAANT | CNGGTTTTTT | CAAACCTCTG | GCCT       |            |            | 514 |

(2) INFORMATION FOR SEQ ID NO:12:

( i ) SEQUENCE CHARACTERISTICS:
        ( A ) LENGTH: 671 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          " N"represents any base.

( x i ) SEQUENCE DESCRIPTION: SEQ ID NO:12:

| NGNTTGACAC | TNTTAAGCTC | GATGCCNACA | TAAGCTGACG | GNGACAAACC | AGGAGCGGGT | 60 |
| ACAGACACCG | AGGACGATTT | ACGCGCGCGC | GATGCACAAG | CTCTTGGGCT | ACCGGCCAAC | 120 |
| GCCGGCTGCA | ATGCCCGTCN | GAGCGACCTG | GGTCAGCTGA | GTCGTGCTCT | ACGTTGCGAT | 180 |
| TGGCGATACT | GGCGACTCAC | TACTGCCCCG | GAAGAATACG | AAGACCCCGG | TGAAGACGAT | 240 |
| TCTTATAGCG | AGTTACCATA | CCGCACGTNG | GNTCCCANCG | ANTATNACNC | TCAGTGNNAT | 300 |
| CCANAGATCG | TATTCGGNNC | AANCACAACC | GTCGCTNGCC | GACTGTNTCA | TCACCGAGCC | 360 |
| AGNGTCGGTN | GACCCCTNCA | CGCCCCCCCC | CNCNCCCCCT | TTTAGCCNNC | CCTCCCCCCG | 420 |
| NNCNCNTGTC | CACCCCCCCC | CTANCCAAGN | NCCCCCCGC  | CNNCCCTNCN | CCNTNCCCNT | 480 |
| NNTTNAGNTT | CTTTTCAAGT | CTTTCATATT | TCTNNATTNN | CNCCTTTTCA | TTTCGATGNA | 540 |
| GGAANCTNCG | TNNNGNTTTG | NNNTTTCTTC | CNGCCTANGT | TGTTTNANNT | TTTTNTTNNN | 600 |
| CNNTTNNNTA | NAATCCNGAG | NNNNTTNCTC | NCTTTANTNT | CGTATTTNTG | AAANTGTTTT | 660 |
| TCACCCCCCC | A          |            |            |            |            | 671 |

(2) INFORMATION FOR SEQ ID NO:13:

( i ) SEQUENCE CHARACTERISTICS:
        ( A ) LENGTH: 616 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          " N"represents any base.

( x i ) SEQUENCE DESCRIPTION: SEQ ID NO:13:

| GAGCTCTGCC | GGGCGTTTGG | AGGTGAACAG | TTTGACCGGC | TGCTCCGTGA | CTGATGGCCG | 60 |
| CAGCGGCGGC | CGACGGGTTA | GGATATTGAC | GACCTAACAG | TTCAGTTATG | TGAGGAGGAT | 120 |
| NAGTTGTGAG | CGGTGAAATC | ATAGTACACA | GGTACAGGCG | AGGGATATCG | CCGNAGCCGT | 180 |
| ATTTCCAGAA | CTCGTCAGCA | TCGGTGGNCA | CGAGATGCAG | AGTTAGTCGA | GGAAAGTCGA | 240 |
| GAAGAAAAAC | ACNGAAGTGG | GGTCCNAGAG | CGANGTNCAG | NNCTNCATNN | TGACAGATAG | 300 |
| TTGNTTGANA | NNCANNGCCA | GNAGTNGTTT | CCTTNCACNA | TNCANGNCAA | TNTAANANCC | 360 |
| NCCCANTNCG | TCNTTTTGNT | NNACANTTNN | CCGNANTTCC | AANNTNNNCC | CACCNNTTNN | 420 |

| | | | | | | |
|---|---|---|---|---|---|---|
| NCNTTTNCNT | NNCCNNNNNT | TNNTCNTTTC | AATATNACCC | NNCCNNNNCN | TCTATTCANN | 480 |
| NNTNTNNNCN | CCTCTCCCNT | CNNAACNNTT | TNTNNTNNTN | NNTNNTNCNC | TTCNNACNNC | 540 |
| NTCCCTCCCC | ATCCNTCNAN | CNNNNTNCNC | NTTNNCNNN | NNNTTTTTT | TTTANTNNTC | 600 |
| CCATTNNTCN | TCNTTA | | | | | 616 |

( 2 ) INFORMATION FOR SEQ ID NO:14:

( i ) SEQUENCE CHARACTERISTICS:
        ( A ) LENGTH: 601 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           "N"represents any base.

( x i ) SEQUENCE DESCRIPTION: SEQ ID NO:14:

| | | | | | | |
|---|---|---|---|---|---|---|
| GAGCTCTACT | AGACGCGGAG | AGACGCGTTC | GCGACGGAAA | AATTCCGGTA | CCCTTTGTGG | 60 |
| ATCGCGATAG | CCTGTTGGCC | AACGTTATTC | CCGTCGCCCC | CACTCCCAAT | CCGGAAANTN | 120 |
| NAGGAAGACC | GGAGAAGAAA | GCACTGACAC | GACAGTGTTC | GNTCCCTACC | CCCCACCCTA | 180 |
| AGAAGTTCGG | AGTNCAGCCT | GATTCCGATA | GCGACAGNGA | TACGATTATC | GATTCAACTA | 240 |
| TGGAAGGNGC | GGNATCTCTG | TAGATTTTTT | TTTGNTGAA | TTGNGCAACC | CGCANTNGCT | 300 |
| TGGTGTNACT | GTAGACAAGN | CTNCTNTNAA | TCANTAGTNT | TNNTTTNGTA | ATAAAACNGN | 360 |
| TTNGTTTNNT | TTAATCCACN | NAGTNGCNNT | GTNTTAATCT | TNNTTGTGGG | NTGATNAGNN | 420 |
| CCNNCCCNCN | NCTTTNACTA | ANTNNTTNTA | ANTTNGNNNN | TNNACNNNNT | NTNNTNTNTN | 480 |
| TNTTCCCNNT | NTNTNTCCCC | NCTTTNNNNT | TNNNNTTNNN | CNTNNTTNTT | NCNNNCCNTC | 540 |
| TNTNTNTNNN | CNTTTNCNTT | ATCTNNTCTC | NCNTATTNTN | NNCCCCTCNC | NTCNCNNTTN | 600 |
| T | | | | | | 601 |

( 2 ) INFORMATION FOR SEQ ID NO:15:

( i ) SEQUENCE CHARACTERISTICS:
        ( A ) LENGTH: 590 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           "N"represents any base.

( x i ) SEQUENCE DESCRIPTION: SEQ ID NO:15:

| | | | | | | |
|---|---|---|---|---|---|---|
| GAGCTCCTAC | CCTGTGCCCT | TATACCATTC | TAGGCACTTT | ATTTTTTACA | TGGCTTGCCT | 60 |
| CTGTTAAATG | TCACCGTAAC | TCCAGATAA | CCTCTTCTGA | TAGCTGGGAA | AACCAAAGCA | 120 |
| CAGATTGGTT | TATAAACTTG | CTCACACAGC | TAGCATCAGA | GAGACCTGGG | ATGTCTATC | 180 |
| ATTTCTGTTC | TCGTATCAAA | GAGGGCCCTT | GTGAGCCTCT | CAGTTGGCCG | ATCCTAACAC | 240 |
| TGGTCAATTG | GAATCTACTC | CCCAATGTTC | CAAGGAATGG | ATGTCATGAA | CCATGGNAGG | 300 |
| TGGNATGGNT | GCTGGAATCC | AGNNNGGTC | CAGGTGANGN | CTCAAGCCAT | ATTGNAGGTT | 360 |
| GGCCTCAAGA | NTTGGCCTC | CCCATGGGT | TATGATGNNG | GGGGTTNCAT | NTTTCACCAA | 420 |
| ATTNGNAANT | TTNGGNCAAN | TCTTTCTTTT | ANNNAAAANT | NTTGGNCTCA | CCNGGNAANA | 480 |
| AANANNAAAG | GGGGGAANNN | TNNNNNNTNN | GGNTTTNGNN | NNNNTTCCCN | NTNCTNTTTT | 540 |
| TANNNNGNNN | NNNNNTGGGG | NNNANNNNNT | NNCCCCNNNN | TCNNNNNAAA | | 590 |

( 2 ) INFORMATION FOR SEQ ID NO:16:

( i ) SEQUENCE CHARACTERISTICS:
        ( A ) LENGTH: 637 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          "N"represents any base.

( x i ) SEQUENCE DESCRIPTION: SEQ ID NO:16:

```
GAGCTCCTCG GTGGGACAGA GCGTANAGGC TGGAGTGCTC GGGGCGCTTC GTGACATTTT    60
ATATCAATAC GCTGACAACG ATGAGTATGG GCTATACGTG GACTGGTACG TCACGGTTGG   120
AATCATCCCT CTGATGGATG TCAAGTCTAA ACCCGCCGAC ATCACGCAGC GCGCAGGCTT   180
CGTCCGAGCC GCAATCCACA GAGCCACAGA GACTCACCCG CTAGCTCAAG ATTTACTGAC   240
CGNTAACCTT CCCGCTTCTG CAGNAAGTGN GTAACGCATC TTNTCGCGG  GTCCCCAATC   300
GTTANCTCCC CCGNAGNTNN CGGATCTTCA AACGAATCCC CTCCGGNAAA GATTGNNGNG   360
CANCCTANNT GAAAAGCATA CCCGCNGCTA TNTTCTTACA GANCCNNTTN GCCTNNNAAC   420
GNNAACANNT TNTTCTTCAN CNNCCCCATC GNCCCACCTT CAGNAAGANA TTTGGCGTT    480
NACGAATNCC TNTTTNCCTC ACNAGNAGTT CTTCCNATTN CNTNNNAANT NTTCANTCAA   540
GCCCNCACCN CNCCCCNTNN TTTACTTAAA AATCNCCNNT CTGNAANCAC NCCCNGAGCN   600
ATTCNANNNN NCCCANAACT NTTTTTNTCT TNTCCNN                             637
```

( 2 ) INFORMATION FOR SEQ ID NO:17:

( i ) SEQUENCE CHARACTERISTICS:
        ( A ) LENGTH: 669 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          "N"represents any base.

( x i ) SEQUENCE DESCRIPTION: SEQ ID NO:17:

```
GAGCTCCTCG GTGNGACAGA GCGTACAGAC TGNAGTGTTC GGCGNGTTNC GNGACANTTT    60
CTATCAATTN GCTGACAANG ATGACTANNG NNNTATTCNT TTNCTGNNA  CNTTATTTTT   120
TNANNTNAAC CCCACTTATN NTTCNCATAT NCTCTNACNN NNCTNANATC AACCTNATNA   180
ATCTTCCNAT ANTNCNTNNT CTTACTACCA TTTTNCTNCT NGATTNTCCN ATTTNCNTTC   240
CACTTNTNTT ANNNTCCANN TTTNCTACTN CNANTNNCNT TTATNCNCNC TCCATCTCTN   300
TTTCCCTCAT NNTCNACTTT TNATANTNCN CTTNACNNCT CNNACNCTAT NNTTTNNACC   360
TTCCANCTAN NCAATCNTNT ATNNCTTTNT ATTAATTNCC TAANCNCNCC TTNNCCNNTN   420
NANTCAAAAT TNCACTATTN NATTTATNNA CNCNTNTTNN TTNCTANTNN CACTCATCNC   480
TCTAAATTNN CNNCTANNAN TTATNTCAAA TNTANTCTTT NTNTATTTAA NATNATCTCA   540
CCNATTTCTC TTATACNCNA TNTNNNANNN CATTTNTANT TAAAANTANA NTATTTTNTT   600
TNTTNTNNTN NNTTNTCNCT CNCATCTNAC ANNNTTTANA NTNCAANNTT TTTNNCCTTC   660
TATCANATN                                                            669
```

( 2 ) INFORMATION FOR SEQ ID NO:18:

( i ) SEQUENCE CHARACTERISTICS:

(A) LENGTH: 715 base pairs
(B) TYPE: nucleic acid
(C) STRANDEDNESS: single
(D) TOPOLOGY: linear (ix) FEATURE:
(D) OTHER INFORMATION:
" N"represents any base.

(xi) SEQUENCE DESCRIPTION: SEQ ID NO:18:

| | | | | | | |
|---|---|---|---|---|---|---|
| GNNTTTGACA | AAGCCCGTNG | TCACAAACGT | CNCGGAGACN | AGTCGGCGCT | CGGGACTCAC | 60 |
| ATCCACCGAC | TCATTGCGCT | CTTGGATCAC | GACAACCATC | GCGAACTGTG | CAATGTGCTG | 120 |
| GTCGGGCTGC | TACACCAAAC | ACCCCACATG | TGGGNCCGNT | CCATCCGTCT | TATCGGTCGA | 180 |
| TTAAGAAACT | ATCTACAACA | GAAGTTTCTC | AATATCTTGG | TGGATAGNGG | NCTCCAGATC | 240 |
| GATAGTCTTT | TTGAGGGTTG | GTACCACAG | CGAAGCGTAC | CGCTTGCTGT | TCCAGATCGA | 300 |
| AAAAACGAAC | TCCACGCCTA | GCTCTCTAGC | CTGTGCAAGC | ACCGNNTTAC | CTGTCGGTGA | 360 |
| AAACGAAACT | GAAGGNACAC | CTNGNNCCGC | CCNNGTNTTT | ANTGAAATAA | TAATATGGGT | 420 |
| NCTCAANGAA | TAAGANGGGG | CTTTTNTTTC | GNNNNNGGTN | NGACAANTNT | NANTCTTCCN | 480 |
| CCCNATNCAA | TNCCTNNCTG | GCCCGTNNNN | TTCGNCTCCN | NTTCNTTTNT | CTTNGGTCCT | 540 |
| GTNNTTTNCT | CATNNNCNNN | ANNTCCTCCT | NGNNCTNCTC | CCCTATCNTC | NNNCTNNTTT | 600 |
| TNNNTNNCTC | NCCNNNNNNT | CNTNTCNCTN | TCNTCNTCTN | TNNCCNNNNT | NTTCNNTCTT | 660 |
| NCCCTTCTCT | TNNTNNNTTN | NTTCNNCTCT | NNTNTNTCNT | TTNTNCNTTN | TCTCC | 715 |

(2) INFORMATION FOR SEQ ID NO:19:

(i) SEQUENCE CHARACTERISTICS:
(A) LENGTH: 737 base pairs
(B) TYPE: nucleic acid
(C) STRANDEDNESS: single
(D) TOPOLOGY: linear (ix) FEATURE:
(D) OTHER INFORMATION:
" N"represents any base.

(xi) SEQUENCE DESCRIPTION: SEQ ID NO:19:

| | | | | | | |
|---|---|---|---|---|---|---|
| TTTTTTNNNN | NNTTTTTTN | CGCACCNNCG | CAATTAACCC | TCACTAAAGG | GAACAAAAGC | 60 |
| TGGAGCTCCA | CAGCTTTCCC | TTGGCATGGA | AAGGGCCAGA | AGAGCCAGTG | GAAGGGACCT | 120 |
| GCCATGCTAA | GGGGCGAGGT | GACCCCATGA | TGAAGGCCAC | AGAGTGTTTA | ACTTAGTAAG | 180 |
| GGTCAGGTGG | AGGGTGCATC | TGAAGCTCAG | AAGGCCGAGC | AGAGCAGTGA | GGAGCTGGGA | 240 |
| TGGGGCAAGT | CGGCAAGGGA | AGAAGACAAA | TTTCAGGTTC | ATCTCCATAC | TCCGGGAGAG | 300 |
| AAAAGCCAGA | AGTAGNCCAT | GGACCAGGCG | TCTCTGNCTC | TACCTCCTGC | ACCTTCTCCA | 360 |
| GTTCCAGNCA | CTCCCGNTCC | CCCTTCACTG | NAGNCACAAC | CAGACTCCAG | NCCTCCAGNN | 420 |
| NTGNCTNGNT | GCCTNNGGNC | CACAGNNCTC | CCNNACCTCC | CNTCTCTCCT | CCNNNNTCAN | 480 |
| ANTCANNTTC | CNNNATCTTC | CTTNNNNTTN | GNNCANNNNC | CNNCTCTCNT | CATNCTCTNT | 540 |
| NNNNNTNNN | NNNTNTTCAN | NNNNCTNNGN | NNNNNNNNTT | CNNNNTTNNN | TNNNNGNAN | 600 |
| NNCNTNNNNA | CCNNTTCCNN | NNNNNNNNN | NNNNNNTCNN | NNNNGNANNN | NNNNTNNNN | 660 |
| NNNNNTNNNN | TNNNNNNNNN | NNNNCCCNN | NNNNNNNNNN | NNNNNNNNN | NCNNNNNNNN | 720 |
| TNNNNNNNNN | NNNTNTT | | | | | 737 |

(2) INFORMATION FOR SEQ ID NO:20:

(i) SEQUENCE CHARACTERISTICS:

( A ) LENGTH: 779 base pairs
( B ) TYPE: nucleic acid
( C ) STRANDEDNESS: single
( D ) TOPOLOGY: linear ( i x ) FEATURE:
  ( D ) OTHER INFORMATION:
    " N"represents any base.

( x i ) SEQUENCE DESCRIPTION: SEQ ID NO:20:

| | | | | | |
|---|---|---|---|---|---|
| GGTTTNGNAA | CTCTTGAAGC | TCTCGNTCCC | CTAGAAACAA | GGCTCAGTAC | GTGGAAGGGG | 60 |
| TGTGGCNTCA | CGCCTACACA | CCTGGGCTGC | TCGACCATCA | TAACGTGTGT | GATCTGGAGG | 120 |
| GGNTTCTTTA | CCTGTTGTGC | TGCGGACCCC | GNAGTTTCTG | CTCGCGGNAC | ACGTGTTTCG | 180 |
| GGCGGGAGAA | GCACGGTTGA | CCATTCCCCG | CCCTGCTCCC | CAAGGATCTT | TTACGAGCCC | 240 |
| GNTCGCGATT | ATATGACGNA | TGTGAACCTG | GCTGAACTTC | TACGTTATG | TGTGGNATCG | 300 |
| CGGCTATGAT | CGCCCTTCGA | CTTCGGATCC | NACGCCAGGG | GNTGATGACG | ACCGANCTNC | 360 |
| NGNCNGNCTT | TTAATAGANC | CGCCCTCNCN | TNCNCACCNN | TCTCAACAGG | ANNTTGCTTA | 420 |
| AAAGNCGTGA | TCCNANCGNC | NGCTTCTTNG | GCCGTCNCNA | TANTTCNCTC | TTCNACNTNC | 480 |
| CTNNCTTNNT | CCTNACANTC | TNNCTTCNTC | CNTCNNGCCT | CNNTGCACNN | CNTATTTCTT | 540 |
| CTNCATCTNT | TTANCCTCCC | NTCNNANTTT | NNNTNNCNA | TCACTCCANN | CACNNCCNNN | 600 |
| TNTTANCCCC | CANNTCCCCC | CCCATTNTTN | NCANCTNCTC | CNCTGCCAAN | NNCCTNNTTT | 660 |
| TTANCCCCNT | CTNNCCATNT | TTTNCTTNGC | TTCNCNTANA | TCCANANTCC | CCCTNNACCT | 720 |
| TACANCTCTN | TATCCTCTNA | TCCCTCCNAC | TATACCCCTT | NTTNTATCNT | NTCCNCCCC | 779 |

( 2 ) INFORMATION FOR SEQ ID NO:21:

( i ) SEQUENCE CHARACTERISTICS:
  ( A ) LENGTH: 682 base pairs
  ( B ) TYPE: nucleic acid
  ( C ) STRANDEDNESS: single
  ( D ) TOPOLOGY: linear ( i x ) FEATURE:
  ( D ) OTHER INFORMATION:
    " N"represents any base.

( x i ) SEQUENCE DESCRIPTION: SEQ ID NO:21:

| | | | | | |
|---|---|---|---|---|---|
| GAGCTCACAA | AACGGTGCTG | GTTTGGTTTT | TTACTTGGCC | CACGGATACG | GGGGAGAGGT | 60 |
| AGACAGGCCC | GACTTCTTTG | TTANTCTCCG | GGTCGTCGGC | GTCCGCCACG | CTGGTCAGCA | 120 |
| GGTGTTGTTT | ACTCTGCACC | AATTCCGACA | GCGGTGTACT | CGCCATCGCG | CCCGTGCCCG | 180 |
| ACCACATGTN | AAAAAGCAAG | TACGTGAAGC | GCTCGGGGA | CGGAGTGCTG | TGTTCTGTAA | 240 |
| ACATCTGTAG | AAGTTGCTTC | GGNGCCTCTG | GGATTTTCAC | AACGATTGTC | TGTTTGTGGT | 300 |
| GGCTAAATCG | CCGGTGTTTG | GTGTACGGTA | CCGTCTCGTC | ACCCATCACC | ATGGCTTTTG | 360 |
| GACCACTGCC | ANATGGCTCA | GGGTTATGTT | TTCGGTTCTT | CCACTGAATC | TCCCAACTGC | 420 |
| TTTTCGAAGC | AGCGATTAAT | ANAAAAATGN | AGATGGAAAT | CAAACAACNT | CAANGAAATN | 480 |
| TTGTCGAAAA | GAGNTNGTCC | ACGTGAAGGT | CCCNANNNTT | CTTGACGCAA | AGTATGATTC | 540 |
| AACTCGGNNA | TNGTNANTNG | CAAACTTTAA | GGCGCCCNCN | NGGCCCATTA | NATTANACNA | 600 |
| NAGAAACTTC | NCCGNATNGC | AANTTGTCTT | ACTTGTCAAN | AGTTTATNNG | GAGTTTGACG | 660 |
| TTNNTCNAGG | GNCAAGTTTT | CT | | | | 682 |

( 2 ) INFORMATION FOR SEQ ID NO:22:

( i ) SEQUENCE CHARACTERISTICS:

( A ) LENGTH: 680 base pairs
( B ) TYPE: nucleic acid
( C ) STRANDEDNESS: single
( D ) TOPOLOGY: linear ( i x ) FEATURE:
( D ) OTHER INFORMATION:
" N"represents any base.

( x i ) SEQUENCE DESCRIPTION: SEQ ID NO:22:

| TGTTTTNCAN | CTTCTCAAGG | GACCCCCCCC | CGAGGAAGAC | GGTATCGATA | AGCTTGATAT | 60 |
| CGAATGCCCT | GCAGNCCGGG | GGNATCCACT | AGTTCTAGAG | CGGNCGCCAC | CGNGGTGGAG | 120 |
| CTCGAGACAG | GTGNCGCGAT | ATGCCNCGGC | CTGGCACCGC | GAACACAGCG | GCCCCTGGCC | 180 |
| GTGACACGTG | AGCTTCAGGA | GTCGCGGGAT | AGTGACGGAG | CGCACCACCA | CGGTGGAATC | 240 |
| GCACGTCCGC | GCAGAGCACG | GTAGAATGAT | GTCAAACGTG | ACGAGGTGGT | CATAGACCGC | 300 |
| ACACGCGGTG | TTCANCCCCA | AGACTGNCTT | CCAACCAAAC | CGNAAACAAC | GTTGCCCACA | 360 |
| NATCGTCTCA | GAGACANCTT | CGTAAACACG | TTCTTTTAAT | GACACGCTGA | CTTCCACAAA | 420 |
| AGAGAACAGT | GCANCAGTTC | GGCGTTAGTA | TTGAAANTGA | CACTCTTTTC | TTGGCGGTCT | 480 |
| CTATANTAGA | ACATAGAGTT | AAGGGGGGAA | TTCTGCTCGC | AGNGNAGGTT | CTCCTGGCCA | 540 |
| AGTTCAAGCA | GGGGNCGAAT | TTCGGANAAC | ACGGNGACAG | GATCTTGGTT | TAGTGGNGTC | 600 |
| NACTCAGNGA | AAAGCACAGG | NGGTTTATAC | GTTCTTTNTC | CCGAGNCNCC | ATCTATATTT | 660 |
| GGTGTCNGGC | CCNTTTTTTT | | | | | 680 |

( 2 ) INFORMATION FOR SEQ ID NO:23:

( i ) SEQUENCE CHARACTERISTICS:
( A ) LENGTH: 822 base pairs
( B ) TYPE: nucleic acid
( C ) STRANDEDNESS: single
( D ) TOPOLOGY: linear ( i x ) FEATURE:
( D ) OTHER INFORMATION:
" N"represents any base.

( x i ) SEQUENCE DESCRIPTION: SEQ ID NO:23:

| GNNTNTGCAC | NTNNTTATAG | GTCTNANTCN | CGTTNAAAAC | ATTTGNGGGT | ACAGCGNTGC | 60 |
| CACCGNCCGA | TGGAGAACGT | GTTGTATGNC | CATNTTCTNC | GNACAGCCNG | GGAGATGATC | 120 |
| TGATGANACA | NGNNCCACTG | ANGAGTGGAG | GANGATNATA | ACGACTACCC | GNCNATTCCA | 180 |
| CAGGTGCGAC | AGGTTCCCCA | GTATCGATCG | TCCATCAGCN | TCGGCTGGNA | CCCACTGANG | 240 |
| GTGANCGCCC | NNATTCACAC | AGTTAAGATG | GCTGAGCAAN | GNNGAGGAAG | ATNACGTCTC | 300 |
| GCTGCACANN | ANCGCCGCAT | TGACCCGTCN | GAAGNNCGGC | ACCATATGGT | GCTNACCCTC | 360 |
| GNNCCCAGT | CCTGTCGACG | GCTATTGANT | NNNTTNNTTN | AANNCCTTGG | CTTANTGTTC | 420 |
| NTTGNNCAG | NTTCACGATN | TTCTNNGCCC | CNANTTTTTC | NGGATCCCCT | CNACATCTTA | 480 |
| NATGTTCGNN | TCGTTTTTAA | NAATCCTNCG | GNTTCCCGTT | CNTTTANTCC | ANTCNNTCNT | 540 |
| NCGNNTTNTC | ACNATGNCNN | ACTCNNGTNN | TNTCANTNTA | TTNTTTACAC | GNATCTTTAN | 600 |
| NCTTTTCNCN | CCCATTCCCC | NCNGNCNNCN | ANGTTNTTNT | CANNNNTCCC | NTCNNNCGTC | 660 |
| NNCNANCTCT | NCAANCANNA | GCNTCTTTNN | TTGCNCATNT | NGTCNTTGGA | ANCTNTNNCN | 720 |
| TTNNAAGNNN | ANNGTACNNC | CTCTTTNTTT | NANNTNACNC | CANANACANG | NNCATTCTTA | 780 |
| AATCNNCNTT | ACNCCCTTAC | TCCATATCTN | TATCTATANT | TT | | 822 |

( 2 ) INFORMATION FOR SEQ ID NO:24:

( i ) SEQUENCE CHARACTERISTICS:
    ( A ) LENGTH: 655 base pairs
    ( B ) TYPE: nucleic acid
    ( C ) STRANDEDNESS: single
    ( D ) TOPOLOGY: linear ( i x ) FEATURE:
    ( D ) OTHER INFORMATION:
        " N"represents any base.

( x i ) SEQUENCE DESCRIPTION: SEQ ID NO:24:

```
GAGCTCATAC  TCCGCTGCTG  AGATGGTGGC  CTGATAGAGT  CGTCTTATGG  CGGTGACGGG    60
TACGGGTAGG  TGTTCCACCG  AGGTGTGCCG  GGAGGTTGGG  CGTNCTGCA   GATGGGTTAT   120
ACACANGTTA  CGANTTAAAC  ATTTGGAGTG  AACGTCTCCG  TCCTTTGGCG  CGCGANTCTT   180
GTAGGGCGGC  ATCGCGCAGC  ATATAGTTCG  CGATTCGCNA  TTCCTCGTTC  CCCGTCTATC   240
GTCCATTGGN  NGAGGGNACA  CAGANTATAG  TCTCCNAGGA  CACAAAAGCG  TCTAGGTGCC   300
CTCAACGGCT  CGCAGGNAAA  TCAANAGAGC  CCANNTTNTT  TNCTTCGANG  CAAAGGTTTC   360
GNCACCCCCG  TCCGTTTATT  TTGTCNCCGA  NAANATGGCT  TCCGCCNGAN  TTTGNTTGT    420
TAGTCANTTC  CCGNNGNNGA  GGNGNATTTT  NTNANNTANC  NTTCANATTA  NNTTAANCNT   480
CNCCAAGCNT  TCTCTTACCT  NTTACNNCNA  ATNCNAACCA  AATCATCNGN  TTCCGCTGNT   540
TAAACTGAAT  NTNACATCNT  TCTCCACTAA  ANCCNNTCNT  NCANACNCNT  NNCCTCCAAT   600
TCTCCTCANA  ATACCNAATA  NCNCNNCCAT  CCNNCTNANT  TNTGNNTCAC  TCNTT        655
```

( 2 ) INFORMATION FOR SEQ ID NO:25:

( i ) SEQUENCE CHARACTERISTICS:
        ( A ) LENGTH: 699 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
            " N"represents any base.

( x i ) SEQUENCE DESCRIPTION: SEQ ID NO:25:

```
NGTCTTTGNA  CCTTNTCAAA  GATCGAGGCN  CCCCGAAATC  GTTGTGTCGG  GGCTGCGCCT    60
TGGTGNCCNC  AGACNGNGTG  TCACGGCAGN  AGTCATGTCG  TCTAGCTCGA  GNAACACGGG   120
TACCAACGTT  ANGAAGGATG  AGGAGNAGCG  GCGCCACGTG  TGTGTGAATG  TATTGGATCT   180
GCCCCAGGAG  TCCATGGAAC  ACCCCGNGAC  CGGNACCATG  TTGTCCAAGT  ACGTCCGGAT   240
GTCCAGCTTC  TTTACAGACA  AGTTTGCCTT  TAAGCTGGAC  TTACTGCGCA  TGTTGGCGGT   300
AGCCAGAACC  CGTCGCTAGC  GGGCGTCTCC  TCGCTACAGT  AGATAGAGGA  AGCGCAGACG   360
GTTAATNGTT  TCGGTTAACC  GATTTAGCCA  TCGATTGAAG  ATCTACGGCG  CACGGATCGT   420
NGGATTTGAA  TNGCGTTTAC  AACATTTGA   GTTAGAGTC   NTCAATTGGN  GGGATTTGGN   480
AAACTNCGAG  CTGGCGGNCN  NAGGGGAGAN  CGGCAATAAA  AACTTCCTCT  ACGANCGATA   540
GCTTNACAGN  TTNCTNGCGG  AAANAGGTTC  GACCANCNTC  ACACGGAGGG  AGCTTTTNNT   600
CCTTCCTCTN  NNAAAGCCTT  NAGNCCTCNA  TCNCCCNNTA  NNTCGTATTT  CCANCACGAT   660
ATCCGNNNCC  CCTNNACTCT  CNCTAATCCN  CCCCTNNNC                            699
```

( 2 ) INFORMATION FOR SEQ ID NO:26:

( i ) SEQUENCE CHARACTERISTICS:
        ( A ) LENGTH: 553 base pairs
        ( B ) TYPE: nucleic acid (C) STRANDEDNESS: single
(D) TOPOLOGY: linear (ix) FEATURE:
(D) OTHER INFORMATION:
"N"represents any base.

(xi) SEQUENCE DESCRIPTION: SEQ ID NO:26:

| | | | | | | |
|---|---|---|---|---|---|---|
| GAGCTCACCA | AACGTTGCGG | AGACAGGTGG | GCGCTCGGGA | CTCACATCCA | CCGACTCATT | 60 |
| GCGCTCTTGG | ATCACGACAA | CCATCGCGAA | CTGTGCAATG | TGCTGGTCGG | NCTGCTACAC | 120 |
| CAAACACCCC | ACATGTGGGC | CCGTTCCATC | CGTCTTATCG | GCCGATTAAG | AAACTATCTA | 180 |
| CAACAGAAGT | TTCTCAATAT | CTTGGTGGAT | AGCGGANTCC | AGATCGATAG | TCTTTGTGAG | 240 |
| GGTTGTTACC | ACAGCGAAGC | GTACCGNTTG | NTGGTCCAGA | TCGAAAAAAA | CGAACTCCAC | 300 |
| GCCTAGNTCT | CTAGCCTGTG | CAAGNACCGN | NTTCACCTGT | CGGTGAAAAC | GAAANTGNAN | 360 |
| GGGACACCTG | TNCCGNCCGT | NTTTTAATN | AAATAATAAA | ATTGGTTCTC | ATNAATTTAN | 420 |
| ACGGNCTTAA | NTNTCCGNNT | TNGGGAAGGN | AAANTTTTNN | TTNTCCCCCC | AAACATTCCC | 480 |
| CCCCTTGGNC | CNNNNTNNNA | NCTNNACTTN | CNNCGGCCN | TNTCCTNANN | AAANCNNATT | 540 |
| TTTTCNNNTN | CCC | | | | | 553 |

(2) INFORMATION FOR SEQ ID NO:27:

(i) SEQUENCE CHARACTERISTICS:
(A) LENGTH: 560 base pairs
(B) TYPE: nucleic acid
(C) STRANDEDNESS: single
(D) TOPOLOGY: linear (ix) FEATURE:
(D) OTHER INFORMATION:
"N"represents any base.

(xi) SEQUENCE DESCRIPTION: SEQ ID NO:27:

| | | | | | | |
|---|---|---|---|---|---|---|
| GAGCTCGAAT | GAGATCACGA | TGATCCGTGG | NGTTCACCAC | GACAGGCCAT | TCCGAGTAAA | 60 |
| CCATGGAATC | CGATACCCCG | TAGGCCGAGT | CCAGAAACAC | CGAGGCGAAA | CTGAACCCCA | 120 |
| GCTCGCAGAT | CACGGNGTCG | CTGAGCATTA | AGTGGTCTTT | TTCCAGANTG | GTCAGCTTCT | 180 |
| GGGTCGTGTA | CCCGAAGTAC | TTCTTGTGCG | GAGNCAGCTT | GACGGACTGC | TGGNTGTCGN | 240 |
| TCACGAACTG | NTTCAGGGNC | GNTTCGATCA | AGCANCTTGG | GTCTCTGAGT | AAGGGNAGGG | 300 |
| GTTTGGCACC | ACGAAGTTN | TTNAACNATA | ATAGAANAGG | GTTTCCGTT | CANCCCNAAG | 360 |
| GNAAGGTCNA | ATCCCCCGNN | GATTCCANGA | ANCGANNTTG | GGTTTTTCCA | GAGAAAAGTT | 420 |
| NANCCCNATT | CCNAAATCGG | CCTNNAAANA | ACAAAGAGGT | GGGNNGGGTN | AAANNNNNA | 480 |
| NGNNNACCNN | TCGANTTCTC | CAANNNNNTT | TGNNCCCCCC | CNCCNNAGAA | GGGTTNANTT | 540 |
| NCCCNATTAT | TAATTTTNTT | | | | | 560 |

(2) INFORMATION FOR SEQ ID NO:28:

(i) SEQUENCE CHARACTERISTICS:
(A) LENGTH: 694 base pairs
(B) TYPE: nucleic acid
(C) STRANDEDNESS: single
(D) TOPOLOGY: linear (ix) FEATURE:
(D) OTHER INFORMATION:
"N"represents any base.

(xi) SEQUENCE DESCRIPTION: SEQ ID NO:28:

| | | | | | | |
|---|---|---|---|---|---|---|
| NTNNTNNNNN | NNNNNGTTTT | NNAACTCTTA | AGCTCTACTA | CCCGCGGAGA | GACGNGTTCG | 60 |

| | | | | | |
|---|---|---|---|---|---|
| CGACGGAAAA | ATTCCGGTCC | CCTTTGTGGA | TCGCGATAGC | CTGTTGGCCA | ACGTTATTCC | 120
| CGTCGCCCCC | ACTCCCAATC | CGGAAACTGA | AGGANGACCG | GAGAAGAAAG | CACTGACACG | 180
| ACAGTGTTCG | CTCCCTACCC | CCCACCCTAA | GAAGCTCGGA | GTCCAGCCTG | ATTCCNATAG | 240
| CGACAGCGAT | ACGATTATCG | ATTAACTAT | GGAAGGCGCG | GGATCTCTGT | AGATTTGTTT | 300
| TTTGNTGAAT | TGTGCAACCC | GCATTGCTTG | GTGTCACTGT | AGACACGCCT | TCTGTCAATC | 360
| ACTAGTGTGC | TTTTGGTAAT | AAACGGNTNT | GGTTGGTATT | AGCCACGCAG | NNNGTGTGTC | 420
| TCATCTTCTT | GGCGGGTGAT | GGAGNGCCTA | CCCGCCTGTG | TNAAGGTTAA | TGGGNTTCAC | 480
| AGTTNGGGAG | TGTGANTTTG | AGATTTTGTT | NAACCCNAAT | TGTTTATTGG | NTTAANTCAA | 540
| GNGTCCTTTN | TTNTTGGNNT | NTTNTANGNT | CTTTNATTNT | TNAATTCCNT | TNTNTTTTTT | 600
| ACGGTNNGGC | GGTTGGNNTC | NTNANTTNNA | ANNCCNNNGN | AAAANTNANN | ANAAANNNNN | 660
| NNNNTTNTNN | ACTTNNTTC | ANCTGNANAA | TTTA | | | 694

( 2 ) INFORMATION FOR SEQ ID NO:29:

( i ) SEQUENCE CHARACTERISTICS:
        ( A ) LENGTH: 704 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          " N"represents any base.

( x i ) SEQUENCE DESCRIPTION: SEQ ID NO:29:

| | | | | | |
|---|---|---|---|---|---|
| TGTTNNNNTG | TCCNTAAAAC | CCTTGAAGCT | CCGGGTNCCC | CGGATTTTAT | TGACGAGATC | 60
| GGAAGTTCTA | GAAGNNTCCA | CCACGCCCCC | AATTTCCTGA | ACCACGCCCA | TTTCGGATTG | 120
| CAAATCGGAG | AGCGGGGGCC | GCTGGGTAGA | AAACGGGGGA | TGGGAACCC | GCAATGCAAC | 180
| CCTATGGGAG | CAGGCCGTCG | AGNACCGTGG | GGGGAGGGGC | GGTNTANCNA | ACCCTGCCAT | 240
| GCACGCTGGT | GCGAGGTGGG | GGTTGGCCAC | TGNAAATGAN | TCTGGGGTCT | CCTGAATAGG | 300
| GGGATNNGGC | TGNAGCCNCC | AACCCNNANT | NATTGGTGCA | TCATGGNGGA | TTNGNNACAC | 360
| AAACCACCTT | TNTTTTTTT | TTNTTNATTG | GANGTTTCTN | NCAACCANAT | NCCTNAACTT | 420
| CTTTNTTTGC | CCCAGNTTNC | TCNNGGNCCC | NNNTNTNTCC | NCCNTCNTTC | CTNNANTCCN | 480
| TNACCTGNGT | NTCTTNNNNT | TAAAANCCNN | TATCCCNTC | NATCANNNGT | GGANTNGGNG | 540
| NNTNNNNCTT | NNGNTNNATN | NNCTCNTCCC | NNNNTTTNNT | NTTTCCTTN | NANTNATNCN | 600
| NTNNNNNTTT | NNTNTTTTN | TTTNNTNCCN | CTTNNNNNCT | CTNNCNTTTN | TCNANTTCAN | 660
| ANCTTNTCNN | NNNTNCNTTN | TNNTCTTTNN | TNNNTNNNNT | TTCT | | 704

( 2 ) INFORMATION FOR SEQ ID NO:30:

( i ) SEQUENCE CHARACTERISTICS:
        ( A ) LENGTH: 727 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          " N"represents any base.

( x i ) SEQUENCE DESCRIPTION: SEQ ID NO:30:

| | | | | | |
|---|---|---|---|---|---|
| TTTTTTTTTG | CNTTCTNAAA | GCAACNACAC | NCAAGGNAAC | ANAAGATGGA | GNTCCAGCGG | 60
| NGNATCGGCT | CGCGCGACCN | GTCGGAAGGT | TCGGAAGCCN | GGCGGNGTTC | AGGGAAACCG | 120

| | | | | | |
|---|---|---|---|---|---|
| ANTCNTTGGA | NNCCNANNTN | AGNCNCANNN | NTTNTTNNAT | NTANGNNGGA | GACANNAGNN | 180
| CNTCCCATNT | NGNANCATAT | NNTTANNTNN | NTCCANACNT | ACCCCANNAA | ANCGGTCNTT | 240
| TTTTTTTTT | TACANANNNT | ACTTAATTTA | AAAANCCTCA | ATANNNAANC | NANNTNNTCC | 300
| CANGNACCAN | NNCGCNNTAT | NNCNAANCTA | TCNNTTNCCN | NGNNNNGCTA | TNANCGACAT | 360
| CATNCATNAA | NTATNNAANC | NAAANNCATN | ATAGAGTTTT | NNTNANATTN | CNANNNCTAC | 420
| AGNNANTCAN | TCNGNNNTTA | ANCANAGNGG | NGGATATCTC | CNCAANCANN | NTANNAANTN | 480
| GACNCCTANN | TATANNTTNN | NNTNNTNTAA | TNCANNCTAN | CANATCNNNN | CNCTCTACAT | 540
| TTNTACNNNA | ANACANATAN | NCAAANNNTN | TNNATNTATN | NNTCCNCCNA | NNTNATNANT | 600
| AATTGTNANT | ATNTACNAGT | GCTNTNCANA | ANGNTNANGC | NATCNNACTC | NCTACTTNAC | 660
| TTAATNNAAN | CACNNNANTT | NNTTCACTAT | NTTNNCNATA | ANTATATATA | NTCNNGNACN | 720
| NNTANCN | | | | | | 727

( 2 ) INFORMATION FOR SEQ ID NO:31:

( i ) SEQUENCE CHARACTERISTICS:
  ( A ) LENGTH: 542 base pairs
  ( B ) TYPE: nucleic acid
  ( C ) STRANDEDNESS: single
  ( D ) TOPOLOGY: linear ( i x ) FEATURE:
  ( D ) OTHER INFORMATION:
   " N"represents any base.

( x i ) SEQUENCE DESCRIPTION: SEQ ID NO:31:

| | | | | | |
|---|---|---|---|---|---|
| GAGCTCGGAC | CTGGTCTTCG | ATAGCAGGGA | ACTCATTATC | AGGAACATGA | GGGATCATTG | 60
| ACAACACCTC | ATCCTCCAAA | ACGTCCCCAT | TGGCCGNCAC | CTCATCCACA | GCAGTGGTAC | 120
| CAGTCGCGTC | CAAAATTGAG | GTGCTTTGAT | CGCAATCCAT | GTCCACCAAA | CCCATAACTT | 180
| TCTGAACTTC | ACACAGNGCC | ACTTGGTCCG | TAGAAAACTT | ATTCAGCAAC | ANCCTCCAGA | 240
| GTGTCGTCCT | CAGACATGGT | AATTTCGCCC | ACCACCAGTT | TTCAAGATCA | TATNGTTCCA | 300
| GAGNCTNCAA | TANTCCCGTT | GCGCAATTCT | GATTCCTCCA | CCTCGGAGGT | GGGGNGCGCT | 360
| ANTCGGCTGG | CATTTATTCC | TCAAAGAAGT | NCNTGCAGNA | GNNGAAATTT | NATCTTGCAC | 420
| TNNCCNATCN | AGGNGGGTTC | AAGCTTGGAG | CAGNTTCTTC | GNNANTTCNT | TGTTCCTACC | 480
| GAAATTTCTT | AANAANCNTC | GNGCNCCNTC | CCAACNTACT | TATNTTATCN | TCGCNGTNNA | 540
| NC | | | | | | 542

( 2 ) INFORMATION FOR SEQ ID NO:32:

( i ) SEQUENCE CHARACTERISTICS:
  ( A ) LENGTH: 563 base pairs
  ( B ) TYPE: nucleic acid
  ( C ) STRANDEDNESS: single
  ( D ) TOPOLOGY: linear ( i x ) FEATURE:
  ( D ) OTHER INFORMATION:
   " N"represents any base.

( x i ) SEQUENCE DESCRIPTION: SEQ ID NO:32:

| | | | | | |
|---|---|---|---|---|---|
| GAGCTCTGCC | GGGGGTGTGG | AGGTGGACNG | TTTGACCGGC | TGCTCCGTGA | CTGATGGCCG | 60
| CAGCGGCGGC | CGACGGGTTA | GGATNTTGAC | GACCTAACAG | TTCAGTTATG | TGAGGAGGAT | 120
| GAGTGGTGAG | CGGTGAAATC | ATAGTNCACA | GGTACAGGCG | AGGGATATCG | CCGCAGCCGT | 180
| NTTTCCAGAA | CTCGTCAGCA | TCGGTGGCCA | CGAGATGCAG | AGTTAGTCGA | GGAAAGTCGA | 240

```
GAAGATNNTT  TATTNTTNTN  GGGTCCCNNG  AGCGAAGGTA  CAGACCTNCA  TGGCGANCAG      300

ATAGTNGGNT  TNANNAGCCA  NNGCCAGAAG  TNGTTTCCGN  NNAATGNTAC  AAGGCACCTT      360

AACAAGACCC  GNCGCTTTTT  TNGGGNNAAA  GTNTGGCGNA  AGCNCAANNN  NCNNACCNAC      420

TNTCNNNGNA  TTTNAAANAC  NNNNGCTNTC  CNTCTNACTC  ANTCTNAACC  NATCCCNNCN      480

GGCTANNNNN  ACTNNNTCNT  CCCNNCCCTT  CTNTNANACC  CNNTGGCNN   CCCTCCANAA      540

NNNCNTTCTC  NCTTAAANTN  CCG                                                 563
```

(2) INFORMATION FOR SEQ ID NO:33:

(i) SEQUENCE CHARACTERISTICS:
        (A) LENGTH: 696 base pairs
        (B) TYPE: nucleic acid
        (C) STRANDEDNESS: single
        (D) TOPOLOGY: linear (ix) FEATURE:
        (D) OTHER INFORMATION:
           "N" represents any base.

(xi) SEQUENCE DESCRIPTION: SEQ ID NO:33:

```
NNTNTAGGGN  GTTTTNTNGN  NCGGGATNNN  NTAAGCCCNN  NTCTNTTTAG  GNATNNNGGC       60

CAGTCGTCAC  CNCNNTNCNN  GCNAAGNANT  AATGGGGGNG  NNGGGGGGGC  TANGGNATNT      120

NGAACNTCAN  NNGTGNACCN  CCANTCCNAG  TCAGCGANNG  CNAGTGANGA  GNCCACACAA      180

NANCGNNAGT  ANANCGACAT  CNATGNGTCT  ANCCTNACAN  GCNNCTTTTA  TCNNATCCAN      240

NNGTANATNN  NCAGAAGAGN  TNTCAANCAT  NTCGCTATA   NTNNCNGNAC  ATAATTCGAA      300

NNANNTCTCT  TCGNANNNNT  CGCTNNNNNG  GCNTNTNGTN  GAACTATAGN  CNNCNANNTN      360

CCTCNCNNAA  CTNGCTNNAA  TNANTTTTTT  NNTTTTATTN  CNNNCTCCGA  CTCGANCNTC      420

CCCTNNGCNN  TTCNNNNNTN  NTNTNATTTT  NNNNCCACCC  NCTNGCCATN  TCCNACANCN      480

NCTCNTNNCN  NGCNCCNNNT  TTTNTCANAN  CNNNCTTNTN  NANAANTTCT  CTCCATTNTN      540

CNNCNCCCNT  TCNANTNTTC  CTATATCCNC  NNANANCAAT  AACTNNTTTN  TNANTTCACC      600

NTACTTTNNT  NGTATACTTA  AACNNTCCCA  CTCCNTCTCC  ANTTTNTNA   ANTCCNNCNC      660

CCNAATCNNC  CACCCNNTNC  NTTTTNNCT   TTTATA                                   696
```

(2) INFORMATION FOR SEQ ID NO:34:

(i) SEQUENCE CHARACTERISTICS:
        (A) LENGTH: 742 base pairs
        (B) TYPE: nucleic acid
        (C) STRANDEDNESS: single
        (D) TOPOLOGY: linear (ix) FEATURE:
        (D) OTHER INFORMATION:
           "N" represents any base.

(xi) SEQUENCE DESCRIPTION: SEQ ID NO:34:

```
GTTTGCAACT  CTGAAGCTCA  TAATCCCTCC  AAATCGGTAG  CGTGGCAGTA  GTAACGATGT       60

CGCCTATGGT  AGCATTCAGA  AAGTAGACGT  CGCTGGCAAA  GGTANGTTTT  CGCCTTTTGA      120

TTAGGACCAG  TAATNTCAGT  ATGTTTGCTA  TGAGTCCGAC  GCATATGGNG  ATGCTATAGA      180

AACCGACGCT  GACATCGCGA  GATGCGTCGT  CGATCTTAAA  CACTTGCAGA  AGGTTACAGG      240

AGGAGTTGTT  CANGTTTGTA  AAAAGTCTGT  TCGCAAATCG  AACAATCTCG  ATTTGCAATG      300

TCGGGGTTNG  TGACCGGNCT  CAAACATATA  TCGGNTGGTN  GTGTCGTTGC  GCTATCAACG      360

CGCAATAATT  TAGAACGCGG  ATTCATATTC  CCTGGGCGGA  AGCTCTGGGG  GATCGTCCNT      420
```

```
TCANGCTATT  NGGGAGACAT  NAGCTTTTAC  AACGTTCCCC  AGCTTATGGN  ATGGTTGGGC      480
ACTCCCATTA  AACANTTCGG  AGGTACCCNC  CTATTGATNT  TACGACTTNA  CACATNTTCN      540
AACTTNATAG  GACTTAAGGA  CGGGTCTTTN  NNAACANAGA  NGGTTTTACC  CNCCCCCCCA      600
AAAAAGTTTG  GTCGTTTCCA  ANTTTTCCNA  ACTTTTCNGN  CGCGATCATC  NCCCCNNCNC      660
TCGAAGNTTT  ACGTTGGCAG  CCCNNGAAAA  NATGTAAAGC  CCNTTATNCN  CCACTNCCCC      720
CTCCNCTTNN  NNCTNCCCNN  CT                                                  742
```

( 2 ) INFORMATION FOR SEQ ID NO:35:

( i ) SEQUENCE CHARACTERISTICS:
    ( A ) LENGTH: 1249 base pairs
    ( B ) TYPE: nucleic acid
    ( C ) STRANDEDNESS: single
    ( D ) TOPOLOGY: linear ( i x ) FEATURE:
    ( D ) OTHER INFORMATION:
      " N"represents any base.

( x i ) SEQUENCE DESCRIPTION: SEQ ID NO:35:

```
NNGAGCTCTG  CCGGGGGTGT  GGAGGTGGAC  NGTTTGACCG  GCTGCTCCGT  GACTGATGGC       60
CGCAGCGGCG  GCCGACGGGT  TAGGATNTTG  ACGACCTAAC  AGTTCAGTTA  TGTGAGGAGG      120
ATGAGTGGTG  AGCGGTGAAA  TCATAGTNCA  CAGGTACAGG  CGAGGGATAT  CGCCGCAGCC      180
GTNTTTCCAG  AACTCGTCAG  CATCGGTGGC  CACGAGATGC  AGAGTTAGTC  GAGGAAAGTC      240
GAGAAGATNN  TTTATTNTTN  TNGGGTCCCN  NGAGCGAAGG  TACAGACCTN  CATGGCGANC      300
AGATAGTNGG  NTTNANNAGC  CANNGCCAGA  AGTNGTTTCC  GNNNAATGNT  ACAAGGCACC      360
TTAACAAGAC  CCGNCGCTTT  TTTNGGGNNA  AAGTNTGGCG  NAAGCNCAAN  NNNCNNACCN      420
ACTNTCNNNG  NATTTNAAAN  ACNNNNGCTN  TCCNTCTNAC  TCANTCTNAA  CCNATCCCNN      480
CNGGCTANNN  NNACTNNNTC  NTCCCNNCCC  TTCTNTNANA  CCCNNTNGGC  NNCCCTCCAN      540
AANNNCNTTC  TCNCTTAAAN  TNCCGNNNTA  TNNNNTGTCT  TTATTCNCTT  CAAGGCCCCC      600
CTCCCAGGTA  GAGGTTTCGA  TAAGCTTGAT  ATCGAATGCC  CNCAGCCCGG  GGGATCCACT      660
AGTTCTAGAG  CGGCCGCCAC  CGNGGTGGAG  CTCCGTTTTC  GCAGCGAGTG  CGGCAGATGG      720
TAGCGATTCA  ACGTTCAGAT  CTGGATGAAT  TCACGTACCC  CTGTCAAGCT  CTTAAAAGGA      780
AAGGGATCGC  TGTACGTCAC  CAACCGTGAC  TGATGCACCA  AAGCTACCAG  GACGCGTTCC      840
GTAGGTCTTT  CTCGCGTCGA  TTGACTTCGT  CCGTTACGAG  GCAGTGGAGA  CGAGGGCCAG      900
GGTCTTCCTG  ATGGGTCGCT  GNCTCGNGCT  CCGNTGCCTC  GACACGAACG  AACTTGAGAC      960
TCGANGGACA  TAGGTCTTTN  TNNGGANCCG  TATTCGTAAG  GGGNGGAAGG  AACCAGNGTA     1020
TTGGNNATCT  TAGNTTCTTC  CCAGGCTTCC  CCTGATACGG  GTCCGGAAGG  CGNTCTTTTT     1080
AAANAAGAGC  CAGTCGGNGG  NNTTTTCTTT  AAAAAAGTTN  TGGNGGGGNT  CTTCCCNNNN     1140
NNNNGGGAGC  AANNNNNTTC  GNNGNGGGNN  ANCCATTTNN  NANNNCNNNC  CNNNNNGGNN     1200
NTTTTAATNN  NTTNCNACCN  NNTNNNNNNN  TAAGTNNGGC  NCNNGGNTT                  1249
```

( 2 ) INFORMATION FOR SEQ ID NO:36:

( i ) SEQUENCE CHARACTERISTICS:
    ( A ) LENGTH: 562 base pairs
    ( B ) TYPE: nucleic acid
    ( C ) STRANDEDNESS: single
    ( D ) TOPOLOGY: linear ( i x ) FEATURE:

( D ) OTHER INFORMATION:
"N"represents any base.

( x i ) SEQUENCE DESCRIPTION: SEQ ID NO:36:

| | | | | | |
|---|---|---|---|---|---|
| GAGCTCCGTT | TTCGCAGCGA | GTGCGGCAGA | TGGTAGCGAT | TCAACGTTCA | GATCTGGATG | 60 |
| AATTCACGTA | CCCCTGTCAA | GCTCTTAAAA | GGAAAGGGAT | CGCTGTACGT | CACCAACCGT | 120 |
| GACTGATGCA | CCAAAGCTAC | CAGGACGCGT | TCCGTAGGTC | TTTCTCGCGT | CGATTGACTT | 180 |
| CGTCCGTTAC | GAGGCAGTGG | AGACGAGGGC | CAGGGTCTTC | CTGATGGGTC | GCTGNCTCGN | 240 |
| GCTCCGNTGC | CTCGACACGA | ACGAACTTGA | GACTCGANGG | ACATAGGTCT | TTNTNNGGAN | 300 |
| CCGTATTCGT | AAGGGGNGGA | AGGAACCAGN | GTATTGGNNA | TCTTAGNTTC | TTCCCAGGCT | 360 |
| TCCCCTGATA | CGGGTCCGGA | AGGCGNTCTT | TTTAAANAAG | AGCCAGTCGG | NGGNNTTTTC | 420 |
| TTTAAAAAAG | TTNTGGNGGG | GNTCTTCCCN | NNNNNNGGG | AGCAANNNNN | TTCGNNGNGG | 480 |
| GNNANCCATT | TNNNANNNCN | NNCCNNNNNG | GNNNTTTTAA | TNNNTTNCNA | CCNNNTNNNN | 540 |
| NNNTAAGTNN | GGCNCNNGGN | TT | | | | 562 |

( 2 ) INFORMATION FOR SEQ ID NO:37:

( i ) SEQUENCE CHARACTERISTICS:
( A ) LENGTH: 622 base pairs
( B ) TYPE: nucleic acid
( C ) STRANDEDNESS: single
( D ) TOPOLOGY: linear ( i x ) FEATURE:
( D ) OTHER INFORMATION:
"N"represents any base.

( x i ) SEQUENCE DESCRIPTION: SEQ ID NO:37:

| | | | | | |
|---|---|---|---|---|---|
| GAGCTCCGTT | TTCGCAGCGA | GTGCGGCANA | TGGTAGCGAT | TCAACGTTCA | GATCTGGATG | 60 |
| AATNCACGTA | CCCCTGTCAA | GCTCTTAAAA | GGAAAGGGAT | CGCTGTACGT | CACCAACCGT | 120 |
| GACTGATGCA | CCAAAGCTAC | CAGGACGCGT | TCCGTAGGTC | TTTCTCGCGT | CGATGACTTC | 180 |
| GTCGTTACGA | GGCAGTGGAG | ACGAGGGCCA | GTGTCTTCCT | GATGGCTCGC | TGNCTCGCGC | 240 |
| TCCGCTGCCT | CGACANCGAC | GGATCTGAGA | CTCGAGGGAC | ATAGGTCTTG | TTGCAACCNT | 300 |
| ATCGTAACGG | TGCAGCAACA | GCGTATTGGG | ATCTTAGCTT | CTCCAGGNT | CCCTGATACG | 360 |
| GGTCGAAGGC | GTCTGTTAAA | CAGAGCCAGT | CGGNGNGTTT | TCTTTAAAAA | GTGCTGGCGG | 420 |
| NGCTCTTCCC | GNNCCGTAGG | GAGCAAAAAA | GTTCNTGGGG | GGGATCCCA | NTGNNATNC | 480 |
| GTCCNGGTNN | GGGAATNTNA | NTNNTNTTCC | ATCGATTTN | TTCTTANGNT | CCGGCTCGAG | 540 |
| GGCCGNACCA | AATANTNANA | GCCCCAAAA | ATTTNNTTTT | TNGCCCNCCC | ATTTGCATTG | 600 |
| NNCCCNTNGN | TTNCGGCCAC | CC | | | | 622 |

( 2 ) INFORMATION FOR SEQ ID NO:38:

( i ) SEQUENCE CHARACTERISTICS:
( A ) LENGTH: 700 base pairs
( B ) TYPE: nucleic acid
( C ) STRANDEDNESS: single
( D ) TOPOLOGY: linear ( i x ) FEATURE:
( D ) OTHER INFORMATION:
"N"represents any base.

( x i ) SEQUENCE DESCRIPTION: SEQ ID NO:38:

| | | | | | |
|---|---|---|---|---|---|
| ACCNNNTCNN | NANNATTTTT | NNNNAGNCNC | TTNANNTNCT | AAAGCNCATN | TANNCCTNAA | 60 |
| AAAAATTTAC | CGNGNGGNTC | TCACTCAGGC | CCCNGCCAAA | NAGGNTTTGG | TGTTTGCGCG | 120 |

-continued

| | | | | | | |
|---|---|---|---|---|---|---|
| GCCGGTCGAG | CCCGATGTGG | CGGTGCCGGA | TNACGTNTCG | GTGTGGTGAC | GGTGCGGCCG | 180 |
| GAGAGGGGGA | GGAGNAGACA | GACNGNGANC | AGNGCGGTCG | NGGNCGGACN | GAGCCGAGNC | 240 |
| GTCTTNTTTT | NGGAGCNGCT | GTATNTCATG | NCCCGACANN | NCCGNNGGGA | NGNCTTCGGA | 300 |
| GCTACGGGTC | ANTTCNNCCA | CNACNTCATT | CNGTNGNCCT | NNNANTCNGT | NTGGGANATT | 360 |
| TATCCCCNGG | NTTAANNNAC | TNNGNCCCTT | TTTTTTTTT | TTTTTTTTT | TTTGCNNNGG | 420 |
| CCCCGCACNA | NNNCACNCGN | AGTTGNTNAG | CCCNNNNCCC | CANCNNCTCC | CTTNNTATNC | 480 |
| CTAACNCTCC | CGGATGGCCC | NTTTTNTTNT | CTCNCGCCGC | CTCTNTGCTN | CTTCTCACAT | 540 |
| TANCATAACN | TCTACTTTNN | TAGCTTNGTC | TCCTTTNCNN | NTTTCTNTC | TNATAAANNN | 600 |
| NCNNNNCNTT | CNNNCTNTTN | NCNTTACNTT | NNCCNTGCTA | TCCNCCCNTN | NCCNNACCCN | 660 |
| TNNCAGTGGN | NNCNTCTCCN | NNACTTCTTN | NNCNATANTN | | | 700 |

(2) INFORMATION FOR SEQ ID NO:39:

(i) SEQUENCE CHARACTERISTICS:
        (A) LENGTH: 696 base pairs
        (B) TYPE: nucleic acid
        (C) STRANDEDNESS: single
        (D) TOPOLOGY: linear (ix) FEATURE:
        (D) OTHER INFORMATION:
            "N"represents any base.

(xi) SEQUENCE DESCRIPTION: SEQ ID NO:39:

| | | | | | | |
|---|---|---|---|---|---|---|
| NNTNTAGGGN | GTTTTNTNGN | NCGGGATNNN | NTAAGCCCNN | NTCTNTTTAG | GNATNNNGGC | 60 |
| CAGTCGTCAC | CNCNNTNCNN | GCNAAGNANT | AATGGGGGNG | NNGGGGGGGC | TANGGNATNT | 120 |
| NGAACNTCAN | NNGTGNACCN | CCANTCCNAG | TCAGCGANNG | CNAGTGANGA | GNCCACACAA | 180 |
| NANCGNNAGT | ANANCGACAT | CNATGNGTCT | ANCCTNACAN | GCNNCTTTTA | TCNNATCCAN | 240 |
| NNGTANATNN | NCAGAAGAGN | TNTCAANCAT | NTCGCTATA | NTNNCNGNAC | ATAATTCGAA | 300 |
| NNANNTCTCT | TCGNANNNNT | CGCTNNNNG | GCNTNTNGTN | GAACTATAGN | CNNCNANNTN | 360 |
| CCTCNCNNAA | CTNGCTNNAA | TNANTTTTTT | NNTTTTATTN | CNNNCTCCGA | CTCGANCNTC | 420 |
| CCCTNNGCNN | TTCNNNNNTN | NTNTNATTTT | NNNNCCACCC | NCTNGCCATN | TCCNACANCN | 480 |
| NCTCNTNNCN | NGCNCCNNNT | TTTNTCANAN | CNNNCTTNTN | NANAANTTCT | CTCCATTNTN | 540 |
| CNNCNCCCNT | TCNANTNTTC | CTATATCCNC | NNANANCAAT | AACTNNTTTN | TNANTTCACC | 600 |
| NTACTTTNNT | NGTATACTTA | AACNNTCCCA | CTCCNTCTCC | ANTTTNTNA | ANTCCNNCNC | 660 |
| CCNAATCNNC | CACCCNNTNC | NTTTTTNNCT | TTTATA | | | 696 |

(2) INFORMATION FOR SEQ ID NO:40:

(i) SEQUENCE CHARACTERISTICS:
        (A) LENGTH: 779 base pairs
        (B) TYPE: nucleic acid
        (C) STRANDEDNESS: single
        (D) TOPOLOGY: linear (ix) FEATURE:
        (D) OTHER INFORMATION:
            "N"represents any base.

(xi) SEQUENCE DESCRIPTION: SEQ ID NO:40:

| | | | | | | |
|---|---|---|---|---|---|---|
| GGTTTNGNAA | CTCTTGAAGC | TCTCGNTCCC | CTAGAAACAA | GGCTCAGTAC | GTGGAAGGGG | 60 |
| TGTGGCNTCA | CGCCTACACA | CCTGGGCTGC | TCGACCATCA | TAACGTGTGT | GATCTGGAGG | 120 |
| GGNTTCTTTA | CCTGTTGTGC | TGCGGACCCC | GNAGTTTCTG | CTCGCGGNAC | ACGTGTTTCG | 180 |

| GGCGGGAGAA | GCACGGTTGA | CCATTCCCCG | CCCTGCTCCC | CAAGGATCTT | TTACGAGCCC | 240 |
| GNTCGCGATT | ATATGACGNA | TGTGAACCTG | GCTGAACTTC | TACGTTTATG | TGTGGNATCG | 300 |
| CGGCTATGAT | CGCCCTTCGA | CTTCGGATCC | NACGCCAGGG | GNTGATGACG | ACCGANCTNC | 360 |
| NGNCNGNCTT | TTAATAGANC | CGCCCTCNCN | TNCNCACCNN | TCTCAACAGG | ANNTTGCTTA | 420 |
| AAAGNCGTGA | TCCNANCGNC | NGCTTCTTNG | GCCGTCNCNA | TANTTCNCTC | TTCNACNTNC | 480 |
| CTNNCTTNNT | CCTNACANTC | TNNCTTCNTC | CNTCNNGCCT | CNNTGCACNN | CNTATTTCTT | 540 |
| CTNCATCTNT | TTANCCTCCC | NTCNNANTTT | NNNTTNNCNA | TCACTCCANN | CACNNCCNNN | 600 |
| TNTTANCCCC | CANNTCCCCC | CCCATTNTTN | NCANCTNCTC | CNCTGCCAAN | NNCCTNNTTT | 660 |
| TTANCCCCNT | CTNNCCATNT | TTTNCTTNGC | TTCNCTANA  | TCCANANTCC | CCCTNNACCT | 720 |
| TACANCTCTN | TATCCTCTNA | TCCCTCCNAC | TATACCCCTT | NTTNATCNT  | NTCCNCCCC  | 779 |

(2) INFORMATION FOR SEQ ID NO:41:

(i) SEQUENCE CHARACTERISTICS:
        (A) LENGTH: 558 base pairs
        (B) TYPE: nucleic acid
        (C) STRANDEDNESS: single
        (D) TOPOLOGY: linear (ix) FEATURE:
        (D) OTHER INFORMATION:
          "N" represents any base.

(xi) SEQUENCE DESCRIPTION: SEQ ID NO:41:

| GAGCTCGTCT | TGCAGCAGAT | TGCGGGTGGA | ATACACGTNT | TCGCTCACAT | CGCACAGCTG | 60 |
| CGTCTTTTGA | CTGCTGACGG | GTTGACAAC  | AGAACCCAGG | GGTGAGAAGC | AANAACGACG | 120 |
| CGAGCAGCGA | AACCAAAAAG | AGCCCTGCCT | AATGAATCCC | CGCAAAGTCT | CGGCGAGTTT | 180 |
| GAGCATCACG | GTCCCGTNAA | TTAAAACGTG | TACGCAACCG | NNTGATNTCC | ATGAACACGG | 240 |
| CCCTGTTAAC | AAGGCTCCAA | CCAGCCAATC | ACCGNGTACT | TGGNCTTNCT | CCAAAAATGC | 300 |
| CAATAACGAG | GNNGGGNTAG | CCTCGNNNGG | GNCTCTTNCA | ACGGTNCGAG | GGATCCCGNN | 360 |
| AGTTGAAANN | TGNATNANGG | GCCNTTCCCC | CCCAGGNNNA | ACCTTGGNCC | CCANNNTTTN | 420 |
| GNTNNANANN | AANNGGACCN | NCGNCTGGGT | ACCCNNCAA  | GANCTTTNAA | ANTTNCCNC  | 480 |
| CCANNTNGGA | AAANTGTNNT | TNTNCCAANN | NTTTTCAAAA | NTTCNNCCAA | ANCGNNNNNC | 540 |
| CNNTTNNTTG | CAANNAAA   |            |            |            |            | 558 |

(2) INFORMATION FOR SEQ ID NO:42:

(i) SEQUENCE CHARACTERISTICS:
        (A) LENGTH: 670 base pairs
        (B) TYPE: nucleic acid
        (C) STRANDEDNESS: single
        (D) TOPOLOGY: linear (ix) FEATURE:
        (D) OTHER INFORMATION:
          "N" represents any base.

(xi) SEQUENCE DESCRIPTION: SEQ ID NO:42:

| TTTGANACT  | TNTTAAGCTC | GATGACACCN | TGANCTGATN | GCGACAAACC | AGGAGCGGCT | 60 |
| ACANCCACCG | AAGACGATTT | ACGCGCGCGC | GATGCACAAG | CTCTTGGGCT | ACCGCCCAAC | 120 |
| GCCGGCTGCA | ATGCCCTCT  | GAGCGACCTG | GNTCAGCTGA | GTCGTGCTCT | ACGTTGCGAT | 180 |
| TGGCGATACT | GGCGACTCAC | TACTGNCCCG | GAAGAATNNG | NTGATCCCGG | CGAAGACGAT | 240 |
| TCTTATAACG | AGTTACCATA | CCGTACGTGG | GCCCCCACCG | ACTATANNCC | TCAGNGGGAN | 300 |

```
CCACAGACCG CATTCGGGGC AANCACAACC NTCGCTCGTC GNTTGTCTCA TCACCGAGCC    360
ANTGCCNTTT TGTTCCCTAC GGCGTCCCTT GGCCCTTNNA GNCCNTCGAT CNNNGTTGNN    420
NGNCANTTTT TCCCNTCTCN AGTACCCNNN GGNGGTGNTT NGNCNNTTCC TNTNNNACGA    480
TTTTNNNAGT NNNNCCANAT TCTTCAGNNT CCCTCTCANT CNCNTCTNNG NANTNTCNCC    540
CCNANTCTGT TTTTTCTTTN GTNNATTTNT TNNTNAATTT TCTTTCTNNN TCCCCCTNAN    600
NACCNTNNNC NTTNTTCTNT TCTTCTNCNC NNNTCTCCNN CNNTNTTNNT CNTNTTNNTN    660
NTNTNCNNTT                                                            670
```

(2) INFORMATION FOR SEQ ID NO:43:

(i) SEQUENCE CHARACTERISTICS:
        (A) LENGTH: 545 base pairs
        (B) TYPE: nucleic acid
        (C) STRANDEDNESS: single
        (D) TOPOLOGY: linear (ix) FEATURE:
        (D) OTHER INFORMATION:
            "N"represents any base.

(xi) SEQUENCE DESCRIPTION: SEQ ID NO:43:

```
GAGCTCTCCG AAAGCTGGAT GNACGNGAGT CTGGTGAACT GGATCTACAG GTTTCGCTGC    60
ATCGTTTCAA TTTACAGAAA TATTCTCTTC GAACTCGCCG GCACCTTCAG CACTTGNGTG    120
CTTCTCTGGT TTAGTTTCCC AACAGTTGAA ATGTGTCTGC TGTGCACTGT CCCGACGGGA    180
GCCATATTAA TTCCCACCCT GTGCCTCGGA ATAGCCTGTT GNTGTCAGAA AGAGATGNTG    240
CGATACTCGG GATCCTCTAC GCTCGNTTGT GTNTTAATTG ACACTTCAAT AACAAGTTAT    300
GACCGGTTTC TTGTNGTCCN GGGNAAAAAC CTCAACCTCG GAATNGGCT TGAGGTNGGG     360
TGATGATCCN NTATTTTNA CNCCCTNGGA ATTANGCCN NCCNNAAGAA AGGCCCTTGN      420
NAATTTTCCC NTCCCNAAGG GGGGGGCCCN NCCCCTTTTT NTTNCTTTNN CCNGGNTNGG    480
GCAAAGGGGC CANCANTTAA AATTTTCCAC CNNNTTTCTC CTTCCTANAA GGGGGTTNAA    540
TTNTT                                                                545
```

(2) INFORMATION FOR SEQ ID NO:44:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (ix) FEATURE:
        (D) OTHER INFORMATION:
            "N"represents any base.

(xi) SEQUENCE DESCRIPTION: SEQ ID NO:44:

```
NCNNTTTTNN NTGTTCTTCT ACTCTGAAGC TCGAGATCNC ACCGATGCAT TNGNCGTGAT    60
GGAGATCCAG GCACACCGTA TCNATGTTCA CGGTAAAAAG CAGNCCCATG AACTCGTNCT    120
GAATGTTCTT GGACGATTTC CAGACGTGAC TGTCCGTTCA AGTAATTGTC CGGCAGGGTT    180
CCCTTGAACT GCGCGGTATA GCGAGTCATC TTCTTGTGAC CGTGACAAGT GACTCTNTTG    240
NTTGTCCACG TAAGCTGTTC CGCGTGGACG ATTAAGTGGT CGTCCTGACG GGTGAGGGTG    300
GNCTTGTCAA ACGGCACTTC TTCGATCCAA CAGTAGNNAA NGTNGNCGGT CAGGGTTAGG    360
AAAGGCAACT CCNTGTNTTN TNTTTATNNC CNNNCNGCTA ACGATNANGN NTNAACCCTT    420
ATCTNTTTTG CNCCANNNNN CCCCCNTCTT CTNCNCNNNT NANANNNNNC CNCGGNCNTC    480
```

| | | | | | | |
|---|---|---|---|---|---|---|
| TTCNTCCNGG | NGNCCCCNCA | NCNTNNCCCN | CNCTANNCNN | GCCNCCTTCN | NCNANTNNCT | 540 |
| TCTCTNCTNC | TTNCCCCCCA | NCTCCCTTTT | CTCTCNANNC | CNCNCNCCNC | NCTNTNCCTC | 600 |
| NTANNNCTTC | NCNNNNTCAC | CNCTNTCNCC | NNCTTTNCCN | ANCCCCCCCT | CCTTTCCCCC | 660 |
| TNCNTCCTTA | TCTTNTNTTT | TCANNTCN | | | | 688 |

( 2 ) INFORMATION FOR SEQ ID NO:45:

( i ) SEQUENCE CHARACTERISTICS:
        ( A ) LENGTH: 670 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           "N"represents any base.

( x i ) SEQUENCE DESCRIPTION: SEQ ID NO:45:

| | | | | | | |
|---|---|---|---|---|---|---|
| TTTGANACT | TNTTAAGCTC | GATGACACCN | TGANCTGATN | GCGACAAACC | AGGAGCGGCT | 60 |
| ACANCCACCG | AAGACGATTT | ACGCGCGCGC | GATGCACAAG | CTCTTGGGCT | ACCGCCCAAC | 120 |
| GCCGGCTGCA | ATGCCCTCT | GAGCGACCTG | GNTCAGCTGA | GTCGTGCTCT | ACGTTGCGAT | 180 |
| TGGCGATACT | GGCGACTCAC | TACTGNCCCG | GAAGAATNNG | NTGATCCCGG | CGAAGACGAT | 240 |
| TCTTATAACG | AGTTACCATA | CCGTACGTGG | GCCCCACCG | ACTATANNCC | TCAGNGGGAN | 300 |
| CCACAGACCG | CATTCGGGGC | AANCACAACC | NTCGCTCGTC | GNTTGTCTCA | TCACCGAGCC | 360 |
| ANTGCCNTTT | TGTTCCCTAC | GGCGTCCCTT | GGCCCTTNNA | GNCCNTCGAT | CNNNGTTGNN | 420 |
| NGNCANTTTT | TCCCNTCTCN | AGTACCCNNN | GGNGGTGNTT | NGNCNNTTCC | TNTNNACGA | 480 |
| TTTTNNNAGT | NNNNCCANAT | TCTTCAGNNT | CCCTCTCANT | CNCNTCTNNG | NANTNTCNCC | 540 |
| CCNANTCTGT | TTTTTCTTTN | GTNNATTTNT | TNNTNAATTT | TCTTTCTNNN | TCCCCCTNAN | 600 |
| NACCNTNNNC | NTTNTTCTNT | TCTTCTNCNC | NNNTCTCCNN | CNNTNTNNT | CNTNTTNNTN | 660 |
| NTNTNCNNTT | | | | | | 670 |

( 2 ) INFORMATION FOR SEQ ID NO:46:

( i ) SEQUENCE CHARACTERISTICS:
        ( A ) LENGTH: 688 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           "N"represents any base.

( x i ) SEQUENCE DESCRIPTION: SEQ ID NO:46:

| | | | | | | |
|---|---|---|---|---|---|---|
| CNNNNTGTNN | NNNGTCCTTA | ACNCTTAAGC | TCCTTGACCC | CAGNNACGGT | GTCCACGGGC | 60 |
| AGCAGGAATT | TGTCACNGCA | AAGGTATTTC | TTCTCCAAAT | CTCTAATATT | GAGATGGCCA | 120 |
| AAAGCTCCCG | CGCGAAGAAA | ATCAGAAAAG | GTAAAATACC | ATCCAGGAGG | CCAAGCGATA | 180 |
| GGAAAAGTTT | CCCCGTTCAC | CTTCGAACA | AACTTCATCA | GACGCTTAGG | CGCGTCCTTG | 240 |
| GTGCTCACGG | AGCAGTTAAA | AAATTCACGG | ACAAGCAATT | CGTGACGCTT | CATGTCGGAA | 300 |
| ACAATCATGA | TGGACGGGGT | TACCAGTGTG | GAACGAAGTC | GGGCACGCCC | GGGCTCGCAG | 360 |
| GAAATAGATA | TAGCTCGTGC | CAACCCACAA | AAATCTGCAT | CTGCGTCAAT | ATTTTTAGG | 420 |
| GTACAACTTT | CTTGCTTTTT | NGGGTTGCTA | GGGTNCGGAA | TTCCGNAATT | GGANAGATNC | 480 |
| GTCGNTTTGT | CCGNNCTTCT | TCCTNGGGNN | NNCGNTAAAG | GTANTNAGAN | TTTTNTNTCC | 540 |

```
CGGGGNNTNG  GGAACCCCCC  TGGGNTTTTT  AANNTATTGG  NCNNACTTTG  TGTTNANCCN      600

NCCTTNNCNG  GNNNNNNGGG  GNCGTTTCCN  NNGGNTNTNN  CGNNGGCAT   CCNTNGNNTT     660

GGNNCCCNNG  NTNNGGGGGN  NTTCNTTN                                           688
```

( 2 ) INFORMATION FOR SEQ ID NO:47:

( i ) SEQUENCE CHARACTERISTICS:
        ( A ) LENGTH: 542 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           " N"represents any base.

( x i ) SEQUENCE DESCRIPTION: SEQ ID NO:47:

```
GAGCTCTAAA  GTATAANTAA  CTTTTNAGGA  CCCTGACCCT  GTTCAAATGG  AGCCAACAGG      60

ATGACACATA  AAGTTATTCC  ACTGATGGGA  AATTTAGTCT  ATTAGAGCAG  TGGTTCTCAG     120

ACTTCTACAT  TTCATGANCA  GAACAACAAC  AATAATAAAT  GGAGAACTTA  CATGGGATTA    180

ACAATTTTAC  CACCTACCTT  TTGGTCAGCT  CACTGAAAAA  AAAAGAAACT  GAACAGCAAG    240

GAAAGAACAG  NTTACTGCCA  CAACTGCCTT  TCTTGTATTC  CATTTNGNTA  CAGACTGGTT    300

AANAAAAAAA  AAAAAANGTC  ACANNTTGGG  NAACANTCCA  CAGACCCATT  NTTGGGGAAA    360

AAATGGGTTA  GAGAGTTTTT  TANGGGCCCT  NCTTATTTTT  NAAANTNGGA  CGNCTTTAAN    420

TCATNTTTTG  GGGGNCNTNA  CNATGCCNNC  CTTAANTTTN  NGNTTACATC  TTGNANGNTT    480

CTCAANGCCA  ANAATNTTTN  ANTNCCCTNC  NATTNAANCA  ATTNTGCCCA  ATTCCCCTNT    540

TT                                                                         542
```

( 2 ) INFORMATION FOR SEQ ID NO:48:

( i ) SEQUENCE CHARACTERISTICS:
        ( A ) LENGTH: 676 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           " N"represents any base.

( x i ) SEQUENCE DESCRIPTION: SEQ ID NO:48:

```
TNGGNAACTC  TCAAGCTCCC  CACCCCATTG  ANAAATATAT  TAACATCACG  TCATCTACTA      60

ANCCCCATTC  AAGTTGTGGT  CTATGGATCA  ATATCGGCAT  CACTGGGGAG  CTTGTAGGAA    120

ATGCAGACTT  TCAAGNTCGA  TCCCAGATCT  GCTGCTGAAT  CAGAAGCCGC  ACTTTCACAA    180

CATCCTAAGT  GATTCGTTTG  NACACTGCAG  TTTAAGAAGC  ACCCACATT   TTGTTGGATA    240

TTCAAAANAA  TGAGAACCTG  ACTTTAGGGT  CTCCTCTCTC  CCACCCTACC  ACTACCTCCA    300

GCAGTCTCCT  TGTCTTCCAG  ATTCCACCTT  AAAATTCAGG  AATCACCATG  CACTGAGGAC    360

AGGCCTGCAC  AAACATCTAG  TTCCCCATGC  TTTAGGAAAA  GTGACAAAAA  CCCACAACCG    420

CCTTCCCTTT  CCCAGGGTCC  CTCCTGCCCC  CAGGAAAAAT  AGGAANTTCC  CTCAAATCTT    480

CCCCCAANGG  CCGGGTGNAG  GNGGGTCAAA  ACCTGGTAAT  CCCAGGACTT  NGGGAGGGTT    540

TGANGCAGGA  GGGGTCAACC  NNAGGNCAGG  GNGTCNAAGN  CCAGGCCCGG  CCGAATGGGN    600

NAAACCCCNC  CTTTCNAANN  GTCAANANTT  GTGGNGGGGN  NNNNNGNCCN  NNNGNCCCNN    660

TTTTCGGGNG  GTTGTT                                                         676
```

( 2 ) INFORMATION FOR SEQ ID NO:49:

( i ) SEQUENCE CHARACTERISTICS:
        ( A ) LENGTH: 698 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           "N"represents any base.

( x i ) SEQUENCE DESCRIPTION: SEQ ID NO:49:

| | | | | | |
|---|---|---|---|---|---|
| NGNCTTANAA | TTNNNNNATA | GCCTTAAAGC | NTNCTAAACT | AGTTTGGNAA | NTCATTATCA | 60 |
| GGGAACNTNC | CGNTTCANNG | ACAACACCTC | ATCCTCCANA | ACGTCCCCAT | GGGNCGTCAC | 120 |
| CTCATCCACA | GNAGTGGCAC | CAGNCGCGTC | CAAAATGGAG | GTGGTTTGNT | CGGAATCCAN | 180 |
| GTCCACCAAG | CCGATAACTT | NCTGAACTTC | ACACAGNGNC | ACTTGNTNCN | NNGAAAACTT | 240 |
| ATTCAGCAAC | ACCTCCAGAG | TGTCGTCCNC | AGACATGGNA | NACTCGNCCA | CCACCAGTTT | 300 |
| CAAGATCATN | NCGTCCAGAG | CCTGNATAAT | CCGCTGCGAC | TTCTGATTCT | CCACCTCGGC | 360 |
| GGCGGGGTGN | NTTTGTGGTT | GGNANTTATC | CGANANGAAG | TCCTGCNAGC | AGGACGACAT | 420 |
| CTTCATCTTG | GNACTGCCG | NTTNNAGNGG | GATCAGNTTG | GAGCAGGNTG | CTTTCGNTCA | 480 |
| CTTCCTGGAT | CCCTTCGCNA | TNNGTNTTAN | TTTTCCTNCG | GCTGTTGATC | NCTTNNGTTC | 540 |
| TGAAGTTTTT | CCTCGCAGGA | AGCAGTGAAT | CTTNTGAAT | CNTNCATTTT | CTNNGCTAGG | 600 |
| NNTGTANCAA | GGANATTNCN | CNATTCTTC | GATTCTCNTC | NTNCNNAATN | TNNNATNTTC | 660 |
| ATANTAGNNT | CNGNCAAGGN | TNNTTCNCCN | TCGTAANG | | | 698 |

( 2 ) INFORMATION FOR SEQ ID NO:50:

( i ) SEQUENCE CHARACTERISTICS:
        ( A ) LENGTH: 610 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           "N"represents any base.

( x i ) SEQUENCE DESCRIPTION: SEQ ID NO:50:

| | | | | | |
|---|---|---|---|---|---|
| GAGCTCCAGA | GGAGATNGGC | TCGCGGGNGC | GGTCGGGAGG | NTCGGAAGCC | TGGGGGNGAC | 60 |
| CAGGGAANCN | ANGCCGTGNA | NCCCGCNATA | GGNCGCGGAC | TGGTTTTTTT | TTTNNTTNAT | 120 |
| GNGGTGCNCG | GACNCAGGGN | CCNGTTCGGN | TCGCAGACTC | NAATAGNNCN | CNATTCANCC | 180 |
| TNGCCTNANN | ATTCANGTAA | ACCCCACNNN | TTTNTAANAA | ANNGCCTANG | TCCCNNCTGN | 240 |
| TAANACGCCC | CCCCGCCTTT | TNTTTTTTN | TTTTTTTTT | TTTAATNCCC | NACNCNNAAC | 300 |
| NGAAANCTCN | AAANTTTCNT | TNCAAANTNA | TNANNCTNTT | NNANATANTT | NTNTCTNACT | 360 |
| ANNTACTCNN | NCNAANAATA | ATTNTAAAAT | AANCNATATA | NTNANAATAA | AATTATATAA | 420 |
| NNATNTCCNC | CTAAATTTCC | NTCTTTATAT | ACACTCCANA | TNAANTNAAN | NTTTATCTTT | 480 |
| CTATTATNTN | ACTACANCAA | NATNNTCATA | ATAATATTCA | ACTNCTNATC | ATTNTACATN | 540 |
| CTCTATATCA | TNANCNNANA | CAANTCNTAT | TATANNCNNA | NTACAATACA | TTNTTTNTA | 600 |
| TAAAATATTT | | | | | | 610 |

( 2 ) INFORMATION FOR SEQ ID NO:51:

( i ) SEQUENCE CHARACTERISTICS:
    ( A ) LENGTH: 586 base pairs
    ( B ) TYPE: nucleic acid
    ( C ) STRANDEDNESS: single
    ( D ) TOPOLOGY: linear ( i x ) FEATURE:
    ( D ) OTHER INFORMATION:
      " N"represents any base.

( x i ) SEQUENCE DESCRIPTION: SEQ ID NO:51:

```
GAGCTCGTCC CTTGCGTACA AGACAGCTGG TTCGTGATGT TCGCAATAAT GACGGAGCTG      60
AGCCGTGAAC ACCAGCTGAT TGAACAGAGT GCAGACGTGC GAGATGGTGG TTTGGATCTG     120
CCCGCCGGCT AGCGGCGGGT CTTGAGTGTG CGGTTGCAGT CGACACTTTA TATTTTNTGT     180
AACGTTCACG ATCTCTGATG AATCAACTCG CGTGCGAGTT CGTTTTAACT GTATGATGCC     240
TTGGATGGAA CTTTCGATAG TCCCGGTCGT TATAAAATAT AAATAAATTA CTGTTGGGGC     300
GAGTGCAGCC GAAAGTGGNA GGCAGGTTGC GAATAAGCAG TTTCTTCTTA CCTTCCGCGC     360
GAATCGGACT CCGGTAAGCT TTAGAAAGGT TATTGGACGN NNGGTTTGNN GTCCCCGNGC     420
TCTCTTTACG GTTCCGCATG GAGAATCGNG NNNCGGTATA TATTTTCANA GGCATGGGAN     480
GCGGTNTCNN CNNGGAAAAG GCTAACGGGG GNTCCANNGG GTTGCCNNCG GTTCNATANC     540
CNNCCCCAC CACGTGGCCN ATCCAAANNA CAATNCTNAA ANCACT                    586
```

( 2 ) INFORMATION FOR SEQ ID NO:52:

( i ) SEQUENCE CHARACTERISTICS:
        ( A ) LENGTH: 673 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          " N"represents any base.

( x i ) SEQUENCE DESCRIPTION: SEQ ID NO:52:

```
TNATTTGAAG TCNNNNNATA CNCTANAGCN TTNNAAACTA CATNATCGAT ATTGAGGCCG      60
ATATTNCCCT TCTNGGAAAG AGCTGNGAGC GCTTNCACTT TTGGCAGANG CTCGTCCATG     120
ACGCGCNCGC TCTGCGCGGG AGCATAACGC GGGTGCAGTG CCGAAAGCTT GATTGAAATA     180
CCCGGGNCAT CATAGATGCC GCGACCGGCC GACGCGCGAT CANTCGNGTN GATCGGANCC     240
TCATAATCCT TGTAATAGCG TTCTGCATCA GNCGNCGNGG TNGGCTGGGT TCACCCAGCA     300
TATCATAGGA GTGGCGGAAG NCGNGTTCTT CAAGCGACTT TGNACGNTTG GANTGCTNCA     360
TCANTGGTTT NNNTNATTTT AAGAGACTGN TCGGCCGTCA GGNGCATNGC CAATATCCAC     420
GNCACGANGG GTAACCCCNN TTCAANCNCA AGGGAGCAAT NGAAGGCGCN TNCANTTNCT     480
TCCGNACAGG GCNNNTCNNC ATTAANGNNN NTTCCNNCAA NTTGACNNNT GNNCAAAAAN     540
GNCCCANCCC NNTNGAATCA GGNCAAANNA AACGGNCACG GGGGAANTTN TAANTNCCNN     600
TNNCCCTCCC NNNTNTTTTC ATNTCNAAAG CATNCNAANN NNNNNTCCTT TCCNNCTGGN     660
NNCCCCNATC ATG                                                        673
```

( 2 ) INFORMATION FOR SEQ ID NO:53:

( i ) SEQUENCE CHARACTERISTICS:
        ( A ) LENGTH: 720 base pairs
        ( B ) TYPE: nucleic acid
        ( C ) STRANDEDNESS: single
        ( D ) TOPOLOGY: linear ( i x ) FEATURE:
    ( D ) OTHER INFORMATION:
        "N" represents any base.

( x i ) SEQUENCE DESCRIPTION: SEQ ID NO:53:

| | | | | | | |
|---|---|---|---|---|---|---|
| GTTTTGCACA | CTCNTGAAGC | TCCCACTGCC | ATCGAGTGGN | GGATAACAAA | CTAACAGCCA | 60 |
| GANACATGCC | ACGATCATTT | GTATTTTATT | TATTGTTGGA | AAATCANCAA | CAGTGTACTC | 120 |
| TGCAGTTCAA | TCGTAACCCC | TGCTTATTTT | TCAGCGGTGA | CGGTCTGAAC | AGTCCGCTTC | 180 |
| TACACGAGCC | CAACCCCTTT | CACCTAACAG | TCCACGCTCC | CTACGACATT | AACTTCGGTC | 240 |
| ACCACTCCAG | NCAGACGGTG | GAGATAGACA | TCCGCTACGT | ACAGACTGGC | GGCCGCTGCT | 300 |
| TTTGGTCGN | CAACCTGCCA | CACGAAGACT | CGTTCTACAC | CGGGATGTGT | CTGTGGCGAA | 360 |
| CAGAGGCACT | GAAGATCACC | CTCTGGTCCC | GGNTGCGCAC | TACCATTATC | CCTCAGGGNA | 420 |
| TCCCTATCGC | CGCGTTGGTA | TCAAATCAAC | GACATCGACG | GCAATCTTNA | CGCGTATAAC | 480 |
| CATAACACGG | TTTTCCCGNA | NAGTTCATCA | TNNCCGACAG | GAACANCCTT | CTTCCCTTAG | 540 |
| GGATTTTAAG | CTCCCCACCA | ATAGTTTCCC | TAACCTCATC | CTANGGGCAA | TTATTCCNCA | 600 |
| TCTNAGGGGN | ATCTTCCTTA | ATTNTCTTT | ATGGATAATG | GTAGNCNGGG | GNCCNTCCGT | 660 |
| CTTCTAGTGG | GGNTGANCCC | CAANTNGGCG | GGGTANCATN | CNGTTTTNGG | TTGACCTGGT | 720 |

( 2 ) INFORMATION FOR SEQ ID NO:54:

( i ) SEQUENCE CHARACTERISTICS:
    ( A ) LENGTH: 632 base pairs
    ( B ) TYPE: nucleic acid
    ( C ) STRANDEDNESS: single
    ( D ) TOPOLOGY: linear ( i x ) FEATURE:
    ( D ) OTHER INFORMATION:
        "N" represents any base.

( x i ) SEQUENCE DESCRIPTION: SEQ ID NO:54:

| | | | | | | |
|---|---|---|---|---|---|---|
| CTGNCACCCG | TNAAGCTCAN | TTACCACTTC | TTGGGAGGAG | GAAATAGATT | TTATCTATCT | 60 |
| NTGGAGCAAT | ATTTAAAGTT | TAGAATTCTT | TTGTTTTCAT | ATATCATTTG | CATCAACTAA | 120 |
| TGGAGAGTTA | AAATGAGAAC | CCCTACTACC | TGCCAACATC | ACTGCTCTGT | GGTGACTATG | 180 |
| AAACGAGTAA | GAGAAACCAT | AGATGCATTT | TGACCTTGTG | TCTGCCTTGC | ACTGCTCCTG | 240 |
| TATCCAGCTC | TACTTGGAGT | TTAATATTGA | CTCTTAAGAG | GACAAATTAN | TTANTGTAAT | 300 |
| AGTACATNGA | AAATGTAAAA | CACACANCAC | CACNCANNNG | CCTNCTCAGC | ATTGGCCTCA | 360 |
| TTCCCATTTT | TCCTCTGTGA | CCCTGTGATA | GACATTAGAG | GTTTCTGCCT | TTCAGAAGCT | 420 |
| TCTNCCCTCC | CNCNCTCGGA | GATGGAGTCT | CACTTTGNTT | GNCCAGNCTG | GAGTGCAGTG | 480 |
| GTGTGATCTC | GGNTCACTGN | AACCACCGNC | TCCCAGGTCA | AGCAATTCTC | CCTGTCTTAG | 540 |
| CCTCCCGAGT | NNTGGGATAC | AGGCANACGC | CACACGCCCA | GGTAATTNGG | GTTTTANGNN | 600 |
| GAGNTGGANT | CCACCAATTG | GCAGCTGGTC | TT | | | 632 |

( 2 ) INFORMATION FOR SEQ ID NO:55:

( i ) SEQUENCE CHARACTERISTICS:
    ( A ) LENGTH: 517 base pairs
    ( B ) TYPE: nucleic acid
    ( C ) STRANDEDNESS: single
    ( D ) TOPOLOGY: linear ( i x ) FEATURE:
    ( D ) OTHER INFORMATION:
        "N" represents any base.

( x i ) SEQUENCE DESCRIPTION: SEQ ID NO:55:

| | | | | | |
|---|---|---|---|---|---|
| GAGCTCCCGA | CCTCAGTTGA | TCCATCCGNC | TCTCAGTCTC | CCAAAGTGTT | GGGATTACAG | 60
| GCGTGAGCCA | CTGTACCCGG | CCAAGAAGTG | TTTATAAAAT | TGTTGAAAAA | TCTGCTGTTT | 120
| GTGGGAGCTT | NTACTCAGGC | ATTCTAAACT | GCTTACCGGT | GTCTTTTGG | CCAGTATCGT | 180
| GGATTGCCTA | CTTGAACAAG | ACTNGTAGGG | GAAGCAGATG | GTCTTGTCAC | TGGCCATGAG | 240
| CTGCTTACCA | TATATTGAGG | AGCCACATTC | ANCTAACTGN | TTTCCGAGCG | ATCATGGAAG | 300
| TTTCTATTAG | CAGCCTGCAG | TACATCAGAG | AAATGATAGC | TTTNCTTTTN | TTNTCNTCAA | 360
| CTTNAACGTN | CTGGGATACA | CGTCTTGAAC | ATGNAGGTTT | GGTACANAGG | TTTTCATATG | 420
| CATGGAAGTT | TGTTNGNTGG | CCCTATCAAC | CACCATTTNG | GTTAAGCCN | NCATCNTAGG | 480
| AGGTGCCCAA | TNCCTCCCCC | CTTTCCCCCT | ACCCCAA | | | 517

( 2 ) INFORMATION FOR SEQ ID NO:56:

( i ) SEQUENCE CHARACTERISTICS:
( A ) LENGTH: 685 base pairs
( B ) TYPE: nucleic acid
( C ) STRANDEDNESS: single
( D ) TOPOLOGY: linear ( i x ) FEATURE:
( D ) OTHER INFORMATION:
"N" represents any base.

( x i ) SEQUENCE DESCRIPTION: SEQ ID NO:56:

| | | | | | |
|---|---|---|---|---|---|
| ANNTTTNNNN | TTTCNTGAAC | TTNTANAGCT | CATGNTCCCC | NNAANTGTGG | AAGGGGGTGG | 60
| GCACAGANAG | CCTGACCTCC | TGNGATGTGT | GGGTGGNGGT | GACCACGGAA | GGCTGAGGTC | 120
| CACCGNGGTG | GCGGTCACTC | TANGAACTAG | TGGATCCCCC | GGCCTGNAGG | AATTCGATAT | 180
| CAANCTTATC | GATACCGTCG | ACCTCGAGGG | GGGGNCCGGT | ACCCATTTCG | TCNTATAGTG | 240
| AGTCGTATTA | CGTGCGCTCA | CTGGGCGGCG | GTTACAACG | TCGNGACTGG | GAAAACCCTG | 300
| GNGTNACCCA | NCTTAATCGA | CTTGNAGNAC | ATCCCCCTTT | CGCCAGCTGG | CGTAATAGCG | 360
| AAGAGGCCCG | CACCNATCGN | CCTTCCCAAC | AGTTGNGCAG | CCTGAATNGC | GAATGGGAAA | 420
| TTGTAAGNGT | TCANTATTTN | NGTTNAAAAT | TNCGNNTTCA | ANNTTTNNGN | TTAANTCAAC | 480
| NTCATTTCTT | TNACCAATAG | GCCCNAAATC | GGNAAAATCC | CTTATTAAAT | TCAACNCAAT | 540
| AGNCCCANAT | AGNNTTNGAN | TTTTGGTACG | ANTCTGGGNA | NAANANTTCC | CCNATTCAAN | 600
| TACCTTCGCN | TCCAATNCCA | AACGGTCTAA | AACCCNNTTC | AGNNCNNATC | NCNCNTNNNN | 660
| TNAACCATCA | CNCTNTCAAT | NTTNA | | | | 685

( 2 ) INFORMATION FOR SEQ ID NO:57:

( i ) SEQUENCE CHARACTERISTICS:
( A ) LENGTH: 535 base pairs
( B ) TYPE: nucleic acid
( C ) STRANDEDNESS: single
( D ) TOPOLOGY: linear ( i x ) FEATURE:
( D ) OTHER INFORMATION:
"N" represents any base.

( x i ) SEQUENCE DESCRIPTION: SEQ ID NO:57:

| | | | | | |
|---|---|---|---|---|---|
| GAGCTCAGGC | TCCGGAGGTC | ACCCCNATGC | ACACATCCCA | GGAGTTCAGG | CTTCTNTGGA | 60
| CACCCCCTTC | NACACATCCC | AGGAGAAGGA | GCTCCAGCTT | CTGTTCCCTT | NAGTGAGGGT | 120
| TAATTGCGCG | CTTGGCGTAA | TCATGGTCAT | AGCTGTTTCC | TGTGTGAAAT | TGTTATCCGC | 180

|     |     |     |     |     |     |
| --- | --- | --- | --- | --- | --- |
| TCACAATTCC | ACACAACATA | CGAGCCGGAA | GCATAAAGTG | TAAAGCCTGG | GGTGCCTAAT | 240 |
| GAGTGAGCTA | ACTCACATTA | ATTGCGTTGN | GCTCAACTGC | CCGCTTTCCA | GTCGGNAAAC | 300 |
| CTGTCGGGCC | AGGTTGNATT | AATGAATCCG | GCCAACGCGC | GGNGAGAGGN | NGGTTTGGGG | 360 |
| TTTTGGGNGN | TCTTCCGNTT | CCTCGGTCAA | TTGATCGTTG | GTCGGNNCGT | CCGGTTGGGG | 420 |
| NAANGGTTNA | ANTCACTCAA | AGGNGGGATN | CGGTNTCCAA | GATCANGGGT | TCCGAGGNAA | 480 |
| NANATTTANN | AANGGCANNA | AAGGCAAGAC | CAAAAGCCNT | TNGTTGNTTT | TTNNA | 535 |

(2) INFORMATION FOR SEQ ID NO:58:

(i) SEQUENCE CHARACTERISTICS:
        (A) LENGTH: 528 base pairs
        (B) TYPE: nucleic acid
        (C) STRANDEDNESS: single
        (D) TOPOLOGY: linear (ix) FEATURE:
        (D) OTHER INFORMATION:
          "N"represents any base.

(xi) SEQUENCE DESCRIPTION: SEQ ID NO:58:

|     |     |     |     |     |     |
| --- | --- | --- | --- | --- | --- |
| GAGCTCTACT | AGANGCGGAG | AGACGGGTGC | GCGACGGAAA | AATTCCGGTA | CCCTTTGTGG | 60 |
| ATCGCGATAG | CCTGTTGGCC | AACGTTATTC | CCGTCGCCCC | CANTCNCAAT | CCGGAAACTG | 120 |
| AAGGAAGACC | GGAGAAGAAA | GCACTGACAC | GACAGTGTTC | GCTCCCTACC | CCCCACCCTA | 180 |
| AGAAGCTCGG | AGTCCAGCCT | GATTCCGATA | GCGACAGNGA | TACGATTATC | GATTTAACTA | 240 |
| TGGAAGGGGC | GGTATCTCTG | TAGATTNNNN | NNNNNGNTGA | ATTGTGCAAC | CCGNATTGNT | 300 |
| TGGGTGTCAC | TTGNAGACAA | GCCTTCTTGT | CAATCANTAG | TGTNNTTTTN | GTAATAAACG | 360 |
| GNTTNGTNGT | TTAACAAGAA | GNNNGGGTNT | CTCATCTTCT | NGGGGGTGAT | GAGNGNCTAC | 420 |
| CCCCCTTNTA | AAGNNATCGN | TTANANTNGN | NGTNTNATTT | GAGTTTTTC | ACCCCNATTT | 480 |
| TATNNNTATC | AANNTCTTNN | TTGGNTNTNN | NTTCTAATNT | CATNCCCN |  | 528 |

(2) INFORMATION FOR SEQ ID NO:59:

(i) SEQUENCE CHARACTERISTICS:
        (A) LENGTH: 643 base pairs
        (B) TYPE: nucleic acid
        (C) STRANDEDNESS: single
        (D) TOPOLOGY: linear (ix) FEATURE:
        (D) OTHER INFORMATION:
          "N"represents any base.

(xi) SEQUENCE DESCRIPTION: SEQ ID NO:59:

|     |     |     |     |     |     |
| --- | --- | --- | --- | --- | --- |
| GAGCTCGTCC | TGGGGCTCGA | TCCAAGCGNA | ATTCACGACG | GGGACTTTCA | AGTGTCTCTG | 60 |
| CATCACAGTG | GNGAAATAAC | AGTCCTCGGT | GGGTGGACTG | ATGGGNAAAA | CGGTGTTCTC | 120 |
| CTCGACGATT | TTGTCTTTTG | CGGNCCACAC | CGAAGGGGTT | ACACTCCACA | GATGGGCAAC | 180 |
| GTCCTCGTCG | GGACCGATAG | CCAGAAACTG | CACATTGCGC | GACCCGTATT | GTTGCATCTC | 240 |
| AGTCCGGAGG | GTCTCCCACT | GCGTCGTTGG | GAGGCGACAG | NCGGGGGTTT | NCGATACAAT | 300 |
| TTCANAACTA | AACTNGCCCN | CCTTTGTCNG | ATGGTGCGAT | CAAACCCACT | CGTAAGGGTC | 360 |
| GGNAGACCGN | NTCTTTACAC | AGGTCCANCG | CTNGTGCCGC | AGNCNCCGNA | TTAGTACATT | 420 |
| TTNTNCAAAN | ANCCCCTCTC | AATTNAACTC | CCCAGGAGGC | NANATTGGTT | NAACCCCCAG | 480 |
| ACGCATTAAC | ACCNTNTTTA | AGNCCCCTTN | AACNAAGNTT | TAANNCCCNC | ATTTTANAAA | 540 |
| AGCCNCTNTA | AAGCCANNTN | CAGCCAATCA | TGATNCAANC | CTTGGCCAA | NCCCCTNCTT | 600 |

-continued

```
CNCATTCCGG AANACTTTAG TCAAANTANC TTTNGTTNCC CCC                           643
```

( 2 ) INFORMATION FOR SEQ ID NO:60:

( i ) SEQUENCE CHARACTERISTICS:
        ( A ) LENGTH: 552 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          " N"represents any base.

( x i ) SEQUENCE DESCRIPTION: SEQ ID NO:60:

```
GAGCTCCGNG TTTCACCCNC TCCGAGGAGT NTCCCTACTG CCACGNTAAA TATGAAACTT          60
ACCTCAGAGT CATGTCGGAC TTTCGNGAAC TGTTNCTGCG ACAGNNCANC TTCGANGGAG         120
TACGNTCGCG GGTGAGTGAC CACATCGATC AAGTTATGTC ATATAGGAAN CCCCAGGAAC         180
TGGNTCGNGC ACGTCAGGTC CGGTGGACAC ATACCGGNNC TGAGAGATCA GCTGNTGGNC         240
NGACAAANAN CTNTTTTTTT TTTNTCTTNT TNCGNGGCGA CNGGANAATC NTATNCATGN         300
TGGGGTGNGG GACCCTCATG GTGGGAGANN GGGACCCCNN TCGTTNNCAT NGGGGCNNNC         360
CACCAANANT TTCATCTTAC NNCCCCCNTC AACNAATTTC CTATTCAANG NNGGNTTNAN         420
ATTTCCNCCC NACNNGNCNA ANNCCGNNTT CTTCACCCNA ATCCNTTTA ANNAANNTCN          480
CANCNNCAAA CNCACCNCCC TCACANCANC NCNTNNNTNC CCCTGCNNTN NNNCNCNNCN         540
NANTTTCNNT TT                                                              552
```

( 2 ) INFORMATION FOR SEQ ID NO:61:

( i ) SEQUENCE CHARACTERISTICS:
        ( A ) LENGTH: 653 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          " N"represents any base.

( x i ) SEQUENCE DESCRIPTION: SEQ ID NO:61:

```
TTTTTGNCAN CCGTGAAGCT CAGGNCACCT TAAATCGTTA CTCTCACCTA AAACGTGTTA          60
GCATCTACGA TCCCCTGAAC ATTGGTGTTA ACTGTTTTGA TTAAACACTT GACTCTTTGT         120
ACCCGCGTGT CATGTGTGGT GTATCTGAGA TGAGGCCCC GCAACATATT TAGAGGTGTG          180
GGCTCTTCAC GAACGATCGA GAACTATGCG ACTTCGTTCG GAAGAAACGG AGACGGTTCG         240
TTCCATCTTT CTATTACGAG TTTACATTCT CATGTGGATC GAGGGCATGC TCTTGTTGAG         300
CACGTGCGCA CTCTGCTGGC TGGTGTTGCC AGAGCGCTTT GTGCACCTTT TACCGAGTAT         360
TCGTAGGANG TTATTTTGGT TTAATGCTTC CTATTATCTG GNNGGGGAAT ACTTCACTTG         420
GGCCCGAGCC TCCAGTTTCC CAGGGGAGCT TGTACGGTCT TGTTGGANTT ACACGTCCAC         480
ATGGCCNNNG GGGACACCGN GCCGNGGNTT CAATCCGNAA ACCCNTCGAC CCCTTACGCC         540
ATNNNGGCTA TATCTTGNTG NNATCNNNCC TNACCCNTTC AAGCTTCNTT NGGCNNAGNC         600
NNNGACCTTC ANNCCNNGGN NNNGNCCCNC CNNCCNNATN NTNNCCNNAN CNT                 653
```

( 2 ) INFORMATION FOR SEQ ID NO:62:

( i ) SEQUENCE CHARACTERISTICS:
        ( A ) LENGTH: 538 base pairs
        ( B ) TYPE: nucleic acid ( C ) STRANDEDNESS: single
( D ) TOPOLOGY: linear ( i x ) FEATURE:
  ( D ) OTHER INFORMATION:
    "N" represents any base.

( x i ) SEQUENCE DESCRIPTION: SEQ ID NO:62:

```
GAGCTCACGT TAATGGCAAT TTGCAAGGGA ACACATCACC CACTGGCTGA CTGTGGGATT      60
TTTATTGGTC TCTTTACTTT TTAAGCGTTC TCGCCATCTT GTGGCTACTT TCAATATTGC     120
AGTTGAATGA TTGGGCACAG GTTCAACCAC CTTGCAAATC ATTAACTCAT CTATTCAAGT     180
ACTTNGGGAG ACTCTAATAT CTCAAGTACT TACACAGAAA AGCAAGTGGA CAAAAGCAAA     240
TAATAAGAAA AAAGCCTAGG AGGAATTAAT GTAATTATTT TCACTACAC TTTTAANCCT      300
CAAGTAGNCA GGCTTGTCGC TGCCAGAGGN CATCAAAACT TTTCCATTTG GGNGGGAAG      360
GNNNGNTTGA CGCCTNTTTC AAAGATTGGG GGGNAAANNN NGGNAGGNAG TCATTTGNGG     420
TNAANNNGTN CNNNACCAGC NNGNCANATN GNANNCCCCN CCTNTTCTNN AANANANATT     480
NNCGNTNTTG NNCAANCNCN NTNNCCCCCC NCNGGNNGGN NNNNATTNNN TCNNNGGG      538
```

( 2 ) INFORMATION FOR SEQ ID NO:63:

( i ) SEQUENCE CHARACTERISTICS:
    ( A ) LENGTH: 605 base pairs
    ( B ) TYPE: nucleic acid
    ( C ) STRANDEDNESS: single
    ( D ) TOPOLOGY: linear ( i x ) FEATURE:
    ( D ) OTHER INFORMATION:
      "N" represents any base.

( x i ) SEQUENCE DESCRIPTION: SEQ ID NO:63:

```
GGGTTTTGAA AGCTCTTGAA GCTCACCAAC CCTTGAGGAG ACNAGTCGGC GCTCGGGACT      60
CACATCCCCC GACTCATTGC GCTCTTGGAT CACGACAACC ATCGCGAACT GTGCAATGTG     120
CTGGTCGGGC TGCTACACCA GAACACCCCA CATGTGGGGC CGTTCCATCC GGCTTATCGG     180
GCGATTAAGA AACTATCTAC AACAGAAGTT TCTCAATATC TTGGTGGATA GCGGACTCCA     240
GATCGATAGT CTTTTTGAGG GTTGTTACCA CAGCGAAGCG TACCGCTTGC TGTTCCAGAT     300
CGAAAAACG AACTCCACGC CTAGCTCTCT ANGCTGTGCA AGCACCGTTT TACCTGTCGG     360
TGAAAACGAA ACTGAAGGNA NACCTGTCCC CGNCGGCGTN TTTTANTGAA ATNCTNAAAT    420
GGCTCTCATG AAATATGACG GCCTTAGTTT CGTNTTNGGA NNGGANAATT NTGNNTCTCC    480
CCCCAAACAT NCCNGNCNTG GNCCCGTGNN TTNGACCCTG AACTTCCGCG GGGGNCCNNT    540
NNCCTTNTGA CAAACNGNCA NTTCNTTCNT NGNTCTCGTA NCCCACCNNT TTAGCGGTNT    600
NNTGG                                                                605
```

( 2 ) INFORMATION FOR SEQ ID NO:64:

( i ) SEQUENCE CHARACTERISTICS:
    ( A ) LENGTH: 732 base pairs
    ( B ) TYPE: nucleic acid
    ( C ) STRANDEDNESS: single
    ( D ) TOPOLOGY: linear ( i x ) FEATURE:
    ( D ) OTHER INFORMATION:
      "N" represents any base.

( x i ) SEQUENCE DESCRIPTION: SEQ ID NO:64:

```
GNTTGCAACT TCTCATAGNT CAGACACCCC CTNANACAAN TTGGCGGCTT GTTCGAGTCG      60
```

| | | | | | |
|---|---|---|---|---|---|
| TGTCCGCATG | GACTGGAGTT | CCTCAACGGG | CAGGGCAGCC | ACTAATGATT | TGATTGTATC | 120
| TTCTTTGCAG | CATGGCGGTG | NTTGGCGTT | TAAGATCTCC | CTGCAGTTCG | GTTATTNTTG | 180
| TGTTTCCTCG | NTGCAGTAGT | GTCGTCTGCG | CCTGACTATC | GANTTTCGAT | AGGATCTGTT | 240
| TTGTGTCTTN | GTTGTCGAAG | GAGATTCTTT | CCAGGTCGTG | ACTATCGATT | CCATAGATGG | 300
| CGGCAGATAG | CTGCTGTAGC | GCTAACTGGA | CCTGTTTTG | CTGTTGGCTG | GTGATCTGTC | 360
| GNCGACCGNT | GACGGCATTC | ACTACCGCCG | AAAAGTCTTG | TNGTNGAAGG | CAGACGAACC | 420
| TTTCGNCGAC | GTCAANTGGC | TTCTCCTCCN | CNTNTTCCCA | GCAGNCCCNA | NAGGGAAGTN | 480
| CCGTATTAGN | AGGNTTCTNC | CTTCCGGCCT | TCAAAAATCT | GNCGAACCCA | TTTCAATAAC | 540
| CTTTNNGCCC | CAAAANTGNA | ACCTANGTNA | ATAAAAACCG | CGGCAAAGTN | NGCCTATCAT | 600
| ACACCCCNTT | GTACGGTAAA | CTTTAAGNTT | AAAANTTTCA | AANTCTCGCC | ACCCANAGTG | 660
| AATCCNTGCT | AGCNANGAAA | GGNTNNATCG | ATTCNCTCAA | ATCCNANTT | CNCCCCCNTT | 720
| NAATCCANNN | TT | | | | | 732

(2) INFORMATION FOR SEQ ID NO:65:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (ix) FEATURE:
        (D) OTHER INFORMATION:
          " N"represents any base.

(xi) SEQUENCE DESCRIPTION: SEQ ID NO:65:

| | | | | | |
|---|---|---|---|---|---|
| TNATTGNATA | CTCTTAAGCT | CTCCGGCCCC | GCCNAAAACC | ANATTTCTCG | TTCGCTAGTT | 60
| GGCTGNCCAT | CANCTNGCTG | TCATTCCTTT | TTAATCAGTG | CAACGAGTTC | TGGGGGTGGT | 120
| TGGAATGGCT | CGCCCTCCGA | GAGNGAGGAA | ACATCGTCGC | TATCTCCTAC | ACTACCGATG | 180
| TGTAGCGGAG | ACGACGGNTG | GGTATGATCG | NCGCCATNCN | TNTTTTNATC | ANNCTCCTCG | 240
| GNGTCGNNCN | CCTCCNCTCC | GGTGTCCTCG | TATTCATCCN | CGGTCTCCTC | GACACCTCTC | 300
| AACGTACTGG | NCGNGTNACC | TTNAGATACG | CNANACACGN | NAANGCNCCN | AGACTNCGNN | 360
| GGTGGATTTT | NTTTNTTTT | TCTTCCCAAA | NCCACTNTTC | CGGNGGTCCC | NNNCANTCCG | 420
| NCTCCATAAN | TTCATCCCNN | CNNTNTNCNN | NNCCCATCTN | GGGGNNTTCT | TTGNAATCAG | 480
| AACCNGTNNG | NAANACACNN | TAANNNCNNT | TCCNNNTAAN | NNGCTNNCCT | CTNNTAACCT | 540
| NTTCCNANNA | NNCTNTCCTN | NCNCNNTTTT | TCNNATNCAT | NTCACTCTTC | TNCNNTTNTN | 600
| CCTNCTTCNN | NCTNNCCCTT | CCNNTTTCNC | NACCTNNTNT | NANCTCCNCT | CNNCCCNCTA | 660
| TCNNCCNTCT | ACANCNACGN | CNTTACCTAC | ATTNTNCAA | | | 699

(2) INFORMATION FOR SEQ ID NO:66:

(i) SEQUENCE CHARACTERISTICS:
        (A) LENGTH: 561 base pairs
        (B) TYPE: nucleic acid
        (C) STRANDEDNESS: single
        (D) TOPOLOGY: linear (ix) FEATURE:
        (D) OTHER INFORMATION:
          " N"represents any base.

(xi) SEQUENCE DESCRIPTION: SEQ ID NO:66:

| | | | | | |
|---|---|---|---|---|---|
| GAGCTCCATC | TCTGTAAAAC | CGTGGCCGCT | CATAATGCGA | TGTTGTGCCC | TCGTTTCGGG | 60

|  |  |  |  |  |  |
|---|---|---|---|---|---|
| AGCGTTGATC | GTTCTAAGCT | TAGTTCGGNA | AACAGTCTGT | CTTATGGTGT | GGGTAGTGGA | 120 |
| TGTGCACTTG | ACGTCATTAT | GTGCGAGAAT | CGGAGGCGAA | CCACCAATTG | TACCGATTTA | 180 |
| GCTTGAAGGT | GAAAAAGAG | GAATGGTTAG | TCTGCCAAAA | GACGGNATCC | GAAAATCATG | 240 |
| AGTCCAGTAA | TATACAATGA | TGAGAATTTC | CACGGTACAA | AACGAATTAA | CAAGGGGAAC | 300 |
| GGCTCCACCG | AGAAACTCCG | TACTTGAGCG | GGGGANAGGA | AGTCNGNNGG | NTAGAAAGTC | 360 |
| CCGGGGGAGA | AAGTTAACAA | GNAGAGCCAA | GGTAGCANCC | CNNCCCATTT | TNTTTAAAAN | 420 |
| GATGGACTNT | TGGGGAGGGG | NATTNNCANN | AANNNGTTTG | NANAAANATC | AAGGGAANAA | 480 |
| GCCNCCCNAA | ANNTTNACCC | CCCCGGAANG | GNCNGGTTCC | CGNTTTTTAA | ACNNTGTTTT | 540 |
| CCNAAAATTA | AATTANNAAA | A |  |  |  | 561 |

( 2 ) INFORMATION FOR SEQ ID NO:67:

( i ) SEQUENCE CHARACTERISTICS:
  ( A ) LENGTH: 642 base pairs
  ( B ) TYPE: nucleic acid
  ( C ) STRANDEDNESS: single
  ( D ) TOPOLOGY: linear ( i x ) FEATURE:
  ( D ) OTHER INFORMATION:
   " N"represents any base.

( x i ) SEQUENCE DESCRIPTION: SEQ ID NO:67:

|  |  |  |  |  |  |
|---|---|---|---|---|---|
| GAGCTCATGN | CACNCTGGAA | NAAAGCAGTT | TCTTGATCAA | TCGTAATGTC | ATACACTTTC | 60 |
| CTCAACAATT | CCTTCTCATT | TAGAAAGACA | GAGTTGATCT | GAATGTGAAA | CCACACTGCA | 120 |
| GGGCTTATCC | TAAGCATAAA | GATGTCCTTT | GGGAGTCTTT | TCAACGCTTA | AGCTATTCTC | 180 |
| AGTCAACCCA | GAAGAGGGTG | CAGGCAAACA | CACAGTGACT | CCAGTACCTG | GAAATTGCAG | 240 |
| CTTGCCTCTC | TTGTCACTGA | CTGTTTATT | ACTTTAGTGT | CTGATTTTA | TGAATACTTG | 300 |
| CAAGTAACTA | CAAGGCACAC | CCTTTTAATT | ATAGTTTTAT | TCATTCACTC | AGACAAATTA | 360 |
| AAGGAACCCT | ATTAGCTGGG | CTATTTTAAC | AAGTTTATGA | CATACAGATA | TGTCTTGAAA | 420 |
| ATTTACATTA | ACAGGGTAAA | AGGCTGGATN | TNTCAACTTN | CTCTGGGGGG | GCTGGTATTA | 480 |
| CTTNATGCCN | TNAAANTGAT | TATTCCCTCN | CTTNCCCCA | TACAACCCCG | GATTAGGAAA | 540 |
| GTAAACCCNG | GTGAAAGGAT | TTTCNTTGGC | CCCTNACTNT | TTNCAAGAAT | TTTAAGGNNT | 600 |
| GGNAATCAAA | ATAGGTGGGC | CCCCCGGNGG | NGGCAGCCCT | NN |  | 642 |

( 2 ) INFORMATION FOR SEQ ID NO:68:

( i ) SEQUENCE CHARACTERISTICS:
  ( A ) LENGTH: 734 base pairs
  ( B ) TYPE: nucleic acid
  ( C ) STRANDEDNESS: single
  ( D ) TOPOLOGY: linear ( i x ) FEATURE:
  ( D ) OTHER INFORMATION:
   " N"represents any base.

( x i ) SEQUENCE DESCRIPTION: SEQ ID NO:68:

|  |  |  |  |  |  |
|---|---|---|---|---|---|
| GAATTCAGCG | TGTCGGAAAC | GCTGTATATA | TGCGAGTGGG | CCGGGTATCC | ATGACGTTGA | 60 |
| TTTGCGTGGT | TTGTGGTTAC | TGATCGGCTG | TCGGCGGTCG | CATTCCACG | GAAATGTGCA | 120 |
| CGTNCTTCGC | GTTCCGAATN | ACATTTTTTG | GTAAANCAAG | CNGCTCCAAA | GACTNGGCCA | 180 |
| CAGGGGNGTA | GGTTATGTTC | NGTGCGTANG | ATCNATNAAA | CAATTGGACC | GGTNTCCCTG | 240 |
| TGGGTTTGNC | GGGGGNTTAT | TGNNGNAAAN | ANGCGGAANC | CCCCTNGTTT | CNCCAACCCT | 300 |

| | | | | | |
|---|---|---|---|---|---|
| CTTTNCCCCT | TGGAACCCAA | AACNCAGGTG | NGGGCCCCTC | NNNGNTTNTA | AACCNTCANA | 360
| CTTTTTTTG | GNGAAGGCAA | NCCNTCTCCG | GTTCANTNTN | GGGNTTCCCA | GGGCTTGGNT | 420
| CNNANTTTTT | CCANNNAAGA | AACNGNCCCN | AANNTNTTTT | AAACNNACAA | CCCCNTAAAG | 480
| GCCCGNNGGT | NTCNCCCGGT | TTTCCNTTT | TCTTGGNCGC | TTTCCNCCCC | CCCTNNAAAT | 540
| TGNTAGTTTA | TTANNCAACN | ANGTTNGNTT | TCANAGNNCA | AAGTCAAGCC | CTTTCCANNT | 600
| TGTTTTGGNN | GGCAANTTTC | GGCANTANTT | TTTNGGTNTT | NGANGGNCTT | TTNANAACCN | 660
| NNGGGGNCGG | TTTTNTNAAA | TTTANNNCNN | TTTCCCCNAN | TTCNTTATTT | CTNCCCNCCC | 720
| GGGGNNCCCC | NCCN | | | | | 734

(2) INFORMATION FOR SEQ ID NO:69:

(i) SEQUENCE CHARACTERISTICS:
    (A) LENGTH: 99 base pairs
    (B) TYPE: nucleic acid
    (C) STRANDEDNESS: single
    (D) TOPOLOGY: linear (xi) SEQUENCE DESCRIPTION: SEQ ID NO:69:

| | | | | | |
|---|---|---|---|---|---|
| GAATTCAGCT | TGTCGTAATC | TCTGTATATA | TGCGAGTTGG | CCGGGTATCC | ATGACGTTGA | 60
| TTTGCGTGGT | TTGTGGTTAC | TGATCGGCTG | TTTTAGTGA | | | 99

(2) INFORMATION FOR SEQ ID NO:70:

(i) SEQUENCE CHARACTERISTICS:
    (A) LENGTH: 645 base pairs
    (B) TYPE: nucleic acid
    (C) STRANDEDNESS: single
    (D) TOPOLOGY: linear (ix) FEATURE:
    (D) OTHER INFORMATION:
        "N"represents any base.

(xi) SEQUENCE DESCRIPTION: SEQ ID NO:70:

| | | | | | |
|---|---|---|---|---|---|
| CNNCNTTNNN | NGACACAAGC | TGGAGCTCCA | CCNCGGTGGC | GGCCGCTCTA | GAACTAGTGG | 60
| ATCCCCCGGG | CTGCAGGAAT | TCGAAGTGTT | GACCAGCGTG | ACTGTAGCTA | CAGTGCCCGG | 120
| TAGCCAAATT | ACAGGACGCG | TGATGAGCCC | TAGCTGCGCC | ATGTGGCGGG | TTCCCACTAC | 180
| GAGGGCGCAA | GTGCTGGGGG | CTTGAATAAA | GGCGGTGTCA | AGGTACACCG | TGTGGGTGTA | 240
| ATTGGGTTGG | ATGATAATCC | GTTGCTGCAC | ACGTAGGGAG | AAGAAGTGGT | TTTCGTTTGG | 300
| GGGTGACATG | TTCATGAGTT | GCCAGGGCTC | GGGACGGAAA | CAGGGGAAGA | TGCAGATGTC | 360
| GCCCTCGATG | GTGCCCGGNG | TGATGGCTTG | GAACGTGTAG | TTAAGATTAA | TAACTTCCAT | 420
| GCTGAGGTTT | CGTAAGCCGG | GTTCGATGAA | TTCTGGCATG | NAACAATTTG | AGAATCCAAA | 480
| CATTTATTAA | AACGTAATTC | CGAAGTNTCC | NATGGGATTN | TAAGGTTGAT | GCCNAGGGTG | 540
| TTGAAGTNTT | GGNTGGTCCG | GTAGCAATAT | GTTGGTGGA | ATTNATGCTT | TCTTGGTTGN | 600
| GAAAATTGAG | GGTCCCTTTC | GGATTTNGGC | NNGNNAATTT | CCNCN | | 645

(2) INFORMATION FOR SEQ ID NO:71:

(i) SEQUENCE CHARACTERISTICS:
    (A) LENGTH: 209 base pairs
    (B) TYPE: nucleic acid
    (C) STRANDEDNESS: single
    (D) TOPOLOGY: linear (xi) SEQUENCE DESCRIPTION: SEQ ID NO:71:

-continued

```
GAATTCGAAT TGTTGACCAG CGTGACTGTA GCTACAGTTC CCGGTAGCCA AATTACAGGA        60
CTCGTGATGA GCCCTAGCTG CGCCATGTGC GGTTCCCACT ACAGGGCGCA AGTTCTGGGG       120
GCTTGAATAA AGGCGGTGTC AAGGTACACC GTGTGGGTGT AATTGGGTTG GATGATAATC       180
CGTTTGCTGC ACACTAGGGA GAAGAAGTT                                        209
```

( 2 ) INFORMATION FOR SEQ ID NO:72:

( i ) SEQUENCE CHARACTERISTICS:
        ( A ) LENGTH: 570 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          "N"represents any base.

( x i ) SEQUENCE DESCRIPTION: SEQ ID NO:72:

```
GAATTCCTAG CCAGCTGTAT GTCCAAAATA CAACCGCGCA ACCACTCTGC TCATGTACCC        60
TGGTGCGGTT GAACTAGCTA ACAGAACTTT AAAAACTAAC GGAGACATCT CCAGCGTCCT       120
CACCGTAGCT CGGCTGGTTT ATGTGTTAGT TAAGCAAAAC CGTCAAGACC TGGTTACGCA       180
CACCGCCATG CAACACGTCC GTGACCTCAT NNTGCGTCTC CATAAATCAC ATATAGCTTC       240
TTTCCTATCA CGGTTTGCTC GCCAGGAACT GTATCTTGCC AGCAGCATTA TTCATTCCAT       300
GCTAAATTAC TCTACCGAAA GACGAGACAT ATTTGTCTTC GAAACAGGAT GTGTTCACTA       360
GCTGAACTCT CACACTGGTC ACAACTCATC GGNGGCCACG AAAACGTCAC ATCAGCGATT       420
TNTCAGTCCA TGCGTTGGAG NGGGGNAGAG ACACGCCTAG ACACTNTNTA CATGTTNCAA       480
AGNACTATCT GGACCTAAAA TGTCTTTTTT TAGACTTAGC AAAATTTCAT CCAGATAATN       540
TCCAGGGAAT TNGGCGTTAA AGTCCNTGAA                                        570
```

( 2 ) INFORMATION FOR SEQ ID NO:73:

( i ) SEQUENCE CHARACTERISTICS:
        ( A ) LENGTH: 563 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          "N"represents any base.

( x i ) SEQUENCE DESCRIPTION: SEQ ID NO:73:

```
GAATTCCATC CCCCGATGA ATTTGCGGCG ACTGGCGGCG TGCCGCTGAG CCGCCAGCTG         60
TTTGTGCCGG TGGTGTTCCT GAGCGGCCTG GCGCAGGGTG TTGCCGGTAA AATCAAAAGC       120
GCTGCCCTGC TTCTCTCGAC GCCACAATTG TCCATATCGA ACGAACATGA GTCTAGAAAT       180
GATACACACG TACCGCTTTA GGCGATCGCC GCTCGAGTCC CGGCGAACTA CGCTATGCGT       240
TCGCGCCACC AGGGACGACG ACGCACCGGG AACACCACCG CAGTGGNGAG AGGAGGCAGG       300
AGGGGGATGA TTTTTGTTTA TAGGCTCGGC CTTANCGATT TCATAGTACA CATAGAATAA       360
ATTACGNCAG ACGGTGTCAT GCTCGCCGAA AGCCAGACTC AAGCGCCGGT ANANAGTATT       420
TTCCCNTACA AAACCGNTTG GTNTTGGCGT AGGTGATGNN AGNTTAAGTC AANATTGGNG       480
TTAAACGCCA GGTAAGTNAT GAATGAANGT GGTCCGAGGA ANGCACATAG NTCCCANCCT       540
TAATCCGNGA GAGGTCAAAN CCT                                               563
```

( 2 ) INFORMATION FOR SEQ ID NO:74:

( i ) SEQUENCE CHARACTERISTICS:
: ( A ) LENGTH: 579 base pairs
: ( B ) TYPE: nucleic acid
: ( C ) STRANDEDNESS: single
: ( D ) TOPOLOGY: linear ( i x ) FEATURE:
: ( D ) OTHER INFORMATION:
: " N"represents any base.

( x i ) SEQUENCE DESCRIPTION: SEQ ID NO:74:

| | | | | | | |
|---|---|---|---|---|---|---|
| GAATTCGTAC | AATCTCACCC | AAGAGTTGTC | GTTAGTGGAG | GACGCTCGGT | TTTGCCAGAC | 60 |
| GCGGCCCGTG | AACGCCGAGC | GCGTTCGCGG | TGTCTTCGGC | GCGCTCTATC | GCGCCGCGTC | 120 |
| CCCGCACATG | CGGGAGGAGA | GTGACCGCAT | CAAGCTGATT | TTGGACGCT | TGTTGCTGGG | 180 |
| ACCCGTGGCC | GTGCCCTGCT | ACTGTGACGA | ATGGGAGGCG | AATGACTACA | TGGTGGAGGC | 240 |
| GGCGCAGTTT | TGCACCGGCC | CCCTGCTGTA | TGTGNACCGA | CGCTGCCACT | GTCCGGTAT | 300 |
| GGGGGCGCG | CTCGCTTTCA | CCGTGATGGA | AGGGCATNTC | GCGACGCATN | TTTTTAGAGG | 360 |
| GNTGCTGTCA | CTCACTGAGT | GGAACCAGNA | CTGCCCCACA | TTTTTGGCC | NTGCNGAACG | 420 |
| GTGANCAGNG | GGATCGGACA | NGAATNGCTG | TCTNCCCGNN | AACTTACGTT | TTNTNTAAGG | 480 |
| AATATCCTAA | TTATGGGGAG | ACGGGTTTCT | CACCNATAGG | GTTATAGTAT | NTATACAATC | 540 |
| TGGGANCCNA | NCCCCNCTAA | TTAAAAAATT | TNGTGGGTA | | | 579 |

( 2 ) INFORMATION FOR SEQ ID NO:75:

( i ) SEQUENCE CHARACTERISTICS:
: ( A ) LENGTH: 586 base pairs
: ( B ) TYPE: nucleic acid
: ( C ) STRANDEDNESS: single
: ( D ) TOPOLOGY: linear ( i x ) FEATURE:
: ( D ) OTHER INFORMATION:
: " N"represents any base.

( x i ) SEQUENCE DESCRIPTION: SEQ ID NO:75:

| | | | | | | |
|---|---|---|---|---|---|---|
| GAATTCACGT | GTACGGGGAC | ATTGACGACC | TGGGGTTCCG | CCGCCGACTC | CACTATTAGA | 60 |
| GCGTCCTGGG | GCGCGCGACA | CTGAAAGACG | GTTGGCGAGG | AAGCCATCGC | CGCACGCCGT | 120 |
| CATGGAAAAC | TGGACGGCAG | TCGAGTTACT | CCCGAAAGTC | GGGATCCCGG | CCGACTTTCT | 180 |
| CACGCATGTA | AAACCAGCG | CCGGGGAAGA | AATGTTCGAC | AGTCTGCGCA | TTTACTACGG | 240 |
| AGATGACCCG | GAACGCTACA | ACATCCACTT | CGAAGCCATC | TTCGGCACCT | TCTNCAATCG | 300 |
| TCTCGAATGG | GTTTACTTCC | TCCAGACGGA | CCTGGCATCG | GCNGCGNACG | CCATCAAGTT | 360 |
| CGATGACCTG | AACAAGATGA | CAACAGGGAA | AATGGTTGTT | TCACATCCAG | NTTGCCGCGT | 420 |
| NTNGGCAGGG | NGCCGGAATG | CCANCTCGAC | CAGACACCAC | ATNGTTACCA | ATNCAGTAAA | 480 |
| AAGCCCCTCA | CCNCCCCTC | NCCTCANGGC | CCCTTTTATG | ACCTGGAAAN | NTCNGACNCA | 540 |
| ACCCGANGTC | NTATTTCGAG | CNNGAAACCA | CTTNNTNTTN | NAAANC | | 586 |

( 2 ) INFORMATION FOR SEQ ID NO:76:

( i ) SEQUENCE CHARACTERISTICS:
: ( A ) LENGTH: 566 base pairs
: ( B ) TYPE: nucleic acid
: ( C ) STRANDEDNESS: single
: ( D ) TOPOLOGY: linear ( i x ) FEATURE:
: ( D ) OTHER INFORMATION:
: " N"represents any base.

( x i ) SEQUENCE DESCRIPTION: SEQ ID NO:76:

| | | | | | |
|---|---|---|---|---|---|
| GAATTCTGTA | ATCCATGCCA | CTTGATTGCG | ATACGTTTCA | TGCAAGCTGG | GTTGCAACTG | 60
| TTCTTAATCT | CGATTGGCCG | TCGCGGGCTT | CCACTCTCAT | TGAAGATGAT | TCCGAACGGG | 120
| TAAAGCGTCA | GAAAAAGAG | CTGGTGCGGA | TGTTTGATGA | GGCGTCGGAG | CATGGCATCA | 180
| ATGCCATGAT | TTTTCAGGTC | TCTCCTGCTG | CCGATGCTTT | CTATAAATCG | GAGTATCTGC | 240
| CGTGGTCGTC | TTATCTCACG | GGTACGCTCG | GAAAAGATCC | GGGCTTCGAT | CCACTNCGCT | 300
| TTGCAATTGC | GGAAGCGCAT | AAGCGCGGGA | TCGAGCTGCA | TGCATGGCTC | AATCCTTATC | 360
| GCGTTTCGAT | GGATGTGCGA | CCAGCAACGC | GGAAAGNACT | GAAAAAACTC | TGCCGGCGAT | 420
| TCTCCGNCCA | GCGTCTATAA | AACCAATCCA | GGCTGGGTNG | NTTATNTCTG | CGGATCCNTT | 480
| ATGTGTTGGA | TCCGGGTNTC | CCGGATGTTG | NCAGTGGNTG | AGAATTTAAG | GCCGAAGCCG | 540
| TCANAATTTA | TGTCGAGGAT | CAGTCC | | | | 566

( 2 ) INFORMATION FOR SEQ ID NO:77:

( i ) SEQUENCE CHARACTERISTICS:
        ( A ) LENGTH: 570 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           "N"represents any base.

( x i ) SEQUENCE DESCRIPTION: SEQ ID NO:77:

| | | | | | |
|---|---|---|---|---|---|
| GAATTCATTC | ATCTTCATGG | GGNAGNAGAA | AAATGAACAT | CAGGACCAGC | TTCCACATTG | 60
| ACACCATGGC | TGTCACCATG | CTCTTTTTCA | ACGGGCTGTT | CAACCTTAAC | ATCTTTCGAG | 120
| ACGTAGTGGC | CGATGACTCA | CAACAAAAAA | GTTGTGATTA | TATGAAACAA | CAACACTTTT | 180
| TNCGCACGAT | GGGTATAGCC | TCTGTGTTTC | TCAGACCCGT | CTTTAGTCCT | ATCATTTACA | 240
| TATGTGTCAG | TCGNAAAATC | ATACAGGGTA | TCTGCAAATT | GTTTATAAAA | GTACCAAACC | 300
| ATACCATAAG | CTCGGAACGT | GTAAAGCTTA | TGTCTCCAAA | TAGAATGAAC | GACGATGCCC | 360
| CAGAGCTTCC | GCCCAGGGGA | ATATGAATCC | GCGTTCTANA | TTATTGCGCG | TTGGTAGGGN | 420
| AACGACACAA | CCAGCCGATT | TNTGTTTGGG | ACCGGTCACA | ANCCCCGAC | ATTGGAAATC | 480
| GACATTGTTC | GGTTGGNGAA | CAGNCTTTTT | ANAACATGAA | CAACTCCCCC | GTACCCTCTG | 540
| AAGTGTTAAG | ACGCGAGNAT | TCGGAGTAGG | | | | 570

( 2 ) INFORMATION FOR SEQ ID NO:78:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:78:

| | | | | |
|---|---|---|---|---|
| GCTCGATTCC | ACCGAACTCT | CAATGAACGG | TCTGCATTG | 39

( 2 ) INFORMATION FOR SEQ ID NO:79:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION:SEQ ID NO:79:

AATGCGGATA GAGCTTGCCA AGTGCTCCGT CACCAATTG ( 2 ) INFORMATION FOR SEQ ID NO:80:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:80:

TGCGCTTCAC AGTAGAAGAG GGACAACTGC TGCAACACAC C          41

( 2 ) INFORMATION FOR SEQ ID NO:81:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:81:

AGGAGCTCCA TTGGAAGAGA CGGATGAGGA ACTCTCCACA G          41

( 2 ) INFORMATION FOR SEQ ID NO:82:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:82:

ATCACACATC TGCATCCTGG GGCGTGAATC ATAGTGTTGA C          41

( 2 ) INFORMATION FOR SEQ ID NO:83:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:83:

ACGAATCCGT CACAGAGAGC CAGCACATTG CACAGTTCGC            40

( 2 ) INFORMATION FOR SEQ ID NO:84:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:84:

GCAACACGAG GCAGAACACT GCTACGCGAG TTGTACCG              38

( 2 ) INFORMATION FOR SEQ ID NO:85:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:85:

CGCTGTCGCT CTCTTCCTTG AGCACGATAC GGTGTTGC              38

( 2 ) INFORMATION FOR SEQ ID NO:86:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:86:

| | | | | |
|---|---|---|---|---|
| AATGTTCGAC | AGTCTGCGCA | CAGACAGCAC | AGGAACCG | 38 |

( 2 ) INFORMATION FOR SEQ ID NO:87:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:87:

| | | | | |
|---|---|---|---|---|
| ACTCTGCTGG | CTGGTGTTGA | GGCGAACCAC | CAATTGTAC | 39 |

( 2 ) INFORMATION FOR SEQ ID NO:88:

( i ) SEQUENCE CHARACTERISTICS:
    ( A ) LENGTH: 669 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:88:

| | | | | | |
|---|---|---|---|---|---|
| GTGGTGCTAG | TGACAGTGAC | ATTCTGGCTC | AGGCTGTCAA | TCAAGCTGGT | ATTGACCATA | 60 |
| GCTCAGCAGG | TACCACCATC | ACCACCCCAT | CCATCTTCAC | CACCACCACT | GCTCCCAGTA | 120 |
| CCCCCCAAGG | TGTTGTTACT | CAGCCTGAGA | GTCAGCCCAT | CCCACCACTT | GTTTGCAATC | 180 |
| CTGAAACCCT | GTTCATCCCA | CGTAAGAAAT | CCCGGAAGAC | AGACTGCCCC | ACCAAGATCA | 240 |
| TTATTAAACC | ACCCGTGCCT | CCCACGTCCA | CCATGATCCC | AGCATCCAG | ATTAAGAAAG | 300 |
| AGCCTGAGGA | ATTCTTCAAG | CTCCAGTACA | AAGACCAGGA | CATCCAACCC | ACCTCTGGAT | 360 |
| GTATTGTGAT | CTCAGACAGT | GAAGAGGAAG | AAGACACTCA | GACTCTGATT | CCCACAGCTT | 420 |
| CCTCCTCCTC | TTCCTCAGAG | AACCAGGGTG | TGCAGCTGAC | AATGACCACC | CCAGGCAGTG | 480 |
| GATCAGTGGG | CAAAATGTCT | GTGGAGAGTT | CCTCATCCTC | CAGCAGCGAG | TCAGAGTGCT | 540 |
| GTGAAGAATG | TGGACTTTCA | TCTCCCAGTA | CGTTGGCATC | TCCAGTGTCC | CCCATTCCAC | 600 |
| CACCCCCACC | AGCACCCGTG | ATGCCCAGCA | CCTCTGGTCG | CAAGCCCAAG | GGTCCCAAGA | 660 |
| CCAAGACCA | | | | | | 669 |

( 2 ) INFORMATION FOR SEQ ID NO:89:

( i ) SEQUENCE CHARACTERISTICS:
    ( A ) LENGTH: 663 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:89:

| | | | | | |
|---|---|---|---|---|---|
| TTGGTGCTAA | TGACAGTGAC | ATACTGGGTC | AGGCTGCCAA | TCAACCTGGT | ATTCACCATA | 60 |
| GCTCAGCAGG | TATCACCATC | ACCACCCCAT | CCATCCTCAC | CACCACCACT | GCTCCCAGCA | 120 |
| CCCCCCAAGT | CGCTGTTACT | CAGTCAGAGA | GTCAGCCAAT | GCCGCCACCT | GTTTGCAATC | 180 |
| CTGAAACCCT | GTTCATCCCA | CGTAAGGAAT | CCCGGAAGAC | AGACTGCCCT | ACCAAGATCA | 240 |

| | | | | | |
|---|---|---|---|---|---|
| TTATTAAACC | ACCCGTGCCT | CCCACGTCCA | CCATGATCCC | AGCATCCCAG | ATTAAGATAG | 300 |
| AGCCTGAGGA | ATTCTTCAAG | CTCCAATACA | AAGACCAGGA | CATCCAACCC | ACCTCTGGAT | 360 |
| GTATTGTGAT | CTCAGACAGT | GAAGAGGAAG | AAGACACTCA | GACTCTGATT | CCCACAGCCT | 420 |
| CCTCTTCCTT | AGATAACCAG | GGTGTGCAGC | TGACAATGAC | CACCCCAGGC | AGTGGATCAG | 480 |
| TGGGCAAAAT | GTCTGTGGAG | AGTTCCTCAT | CCTCCAGCAG | CGAGTCAGAG | TGCTGTGAAG | 540 |
| AATGTGGACT | TTCATCTCCC | AGTACGTTGG | CATCCCCGGT | GTCTCCCCTT | CCACCACCCC | 600 |
| CACCAGCACC | CGTGATGCCC | AGCACCTCTG | GTGCCAAGCC | CAAGGGTCCC | AAGACCATGA | 660 |
| CCA | | | | | | 663 |

( 2 ) INFORMATION FOR SEQ ID NO:90:

( i ) SEQUENCE CHARACTERISTICS:
        ( A ) LENGTH: 663 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:90:

| | | | | | |
|---|---|---|---|---|---|
| CTTCTTATCA | CCATCAGGTG | ACATCCTCGC | CCAGGCTGTC | AATCATGCCG | GTATCGATTC | 60 |
| CAGTAGCACC | GGCCCCACGC | TGACAACCCA | CTCTTGCAGC | GTTAGCAGCG | CCCCTCTTAA | 120 |
| CAAGCCGACC | CCCACCAGCG | TCGCGGTTAC | TAACACTCCT | CTCCCCGGGG | CATCCGCTAC | 180 |
| TCCCGAGCTC | AGCCCGCGTA | AGAAACCGCG | CAAAACCACG | CGTCCTTTCA | AGGTGATTAT | 240 |
| TAAACCGCCC | GTGCCTCCCG | CGCCTATCAT | GCTGCCCCTC | ATCAAACAGG | AAGACATCAA | 300 |
| GCCCGAGCCC | GACTTTACCA | TCCAGTACCG | CAACAAGATT | ATCGATACCG | CCGGCTGTAT | 360 |
| CGTGATCTCT | GATAGCGAGG | AAGAACAGGG | TGAAGAAGTC | GAAACCCGCG | GTGCTACCGC | 420 |
| GTCTTCCCCT | TCCACCGGCA | GCGGCACGCC | GCGAGTGACC | TCTCCCACGC | ACCCGCTCTC | 480 |
| CCAGATGAAC | CACCCTCCTC | TTCCCGATCC | CTTGGGCCGG | CCCGATGAAG | ATAGTTCCTC | 540 |
| TTCGTCTTCC | TCCTCCTGCA | GTTCGGCTTC | GGACTCGGAG | AGTGAGTCCG | AGGAGATGAA | 600 |
| ATGCAGCAGT | GGCGGAGGAG | CATCCGTGAC | CTCGAGCCAC | CATGGGCGCG | GCGGTTTTGG | 660 |
| TGG | | | | | | 663 |

( 2 ) INFORMATION FOR SEQ ID NO:91:

( i ) SEQUENCE CHARACTERISTICS:
        ( A ) LENGTH: 219 amino acids
        ( B ) TYPE: amino acid
        ( C ) STRANDEDNESS: single
        ( D ) TOPOLOGY: linear ( x i ) SEQUENCE DESCRIPTION: SEQ ID NO:91:

```
Gly Ala Ser Asp Ser Asp Ile Leu Ala Gln Ala Val Asn Gln Ala Gly
 1               5                  10                  15

Ile Asp His Ser Ser Ala Gly Thr Thr Ile Thr Thr Pro Ser Ile Phe
            20                  25                  30

Thr Thr Thr Thr Ala Pro Ser Thr Pro Gln Gly Val Val Thr Gln Pro
        35                  40                  45

Glu Ser Gln Pro Ile Pro Pro Leu Val Cys Asn Leu Thr Leu Phe Ile
    50                  55                  60

Pro Arg Lys Lys Ser Arg Lys Thr Asp Cys Pro Thr Lys Ile Ile Ile
65                  70                  75                  80

Lys Pro Pro Val Pro Pro Thr Ser Thr Met Ile Pro Ala Ser Gln Ile
                85                  90                  95
```

-continued

```
Lys  Lys  Glu  Pro  Glu  Glu  Phe  Phe  Lys  Leu  Gln  Tyr  Lys  Asp  Gln  Asp
               100                 105                      110

Ile  Gln  Pro  Thr  Ser  Gly  Cys  Ile  Val  Ile  Ser  Asp  Ser  Glu  Glu  Glu
          115                      120                      125

Glu  Asp  Thr  Gln  Thr  Leu  Ile  Pro  Thr  Ala  Ser  Ser  Ser  Ser  Ser  Ser
     130                 135                      140

Glu  Asn  Gln  Gly  Val  Gln  Leu  Thr  Met  Thr  Thr  Pro  Gly  Ser  Gly  Ser
145                      150                      155                      160

Val  Gly  Lys  Met  Ser  Val  Glu  Ser  Ser  Ser  Ser  Ser  Ser  Ser  Glu  Ser
               165                      170                           175

Glu  Cys  Cys  Glu  Glu  Cys  Gly  Leu  Ser  Ser  Pro  Ser  Thr  Leu  Ala  Ser
               180                 185                      190

Pro  Val  Ser  Pro  Ile  Pro  Pro  Pro  Pro  Ala  Pro  Val  Met  Pro  Ser
          195                 200                      205

Thr  Ser  Gly  Arg  Lys  Pro  Lys  Gly  Pro  Lys  Thr
     210                      215
```

( 2 ) INFORMATION FOR SEQ ID NO:92:

( i ) SEQUENCE CHARACTERISTICS:
        ( A ) LENGTH: 218 amino acids
        ( B ) TYPE: amino acid
        ( C ) STRANDEDNESS: single
        ( D ) TOPOLOGY: linear ( x i ) SEQUENCE DESCRIPTION: SEQ ID NO:92:

```
Gly  Ala  Asn  Asp  Ser  Asp  Ile  Leu  Gly  Gln  Ala  Ala  Asn  Gln  Pro  Gly
1                   5                        10                      15

Ile  His  His  Ser  Ser  Ala  Gly  Thr  Thr  Ile  Thr  Thr  Pro  Ser  Ile  Leu
               20                      25                      30

Thr  Thr  Thr  Thr  Ala  Pro  Ser  Thr  Pro  Gln  Val  Ala  Val  Thr  Gln  Ser
          35                      40                      45

Glu  Ser  Gln  Pro  Met  Pro  Pro  Val  Cys  Asn  Pro  Glu  Thr  Leu  Phe
     50                      55                      60

Ile  Pro  Arg  Lys  Glu  Ser  Arg  Lys  Thr  Asp  Cys  Pro  Thr  Lys  Ile  Ile
65                       70                      75                      80

Ile  Lys  Pro  Pro  Val  Pro  Pro  Thr  Ser  Thr  Met  Ile  Pro  Ala  Ser  Gln
                    85                      90                      95

Ile  Lys  Ile  Glu  Pro  Glu  Glu  Phe  Phe  Lys  Leu  Gln  Tyr  Lys  Asp  Gln
               100                 105                      110

Asp  Ile  Gln  Pro  Thr  Ser  Gly  Cys  Ile  Val  Ile  Ser  Asp  Ser  Glu  Glu
          115                      120                      125

Glu  Glu  Asp  Thr  Gln  Thr  Leu  Ile  Pro  Thr  Ala  Ser  Ser  Ser  Leu  Asp
     130                      135                      140

Asn  Gln  Gly  Val  Gln  Leu  Thr  Met  Thr  Thr  Pro  Gly  Ser  Gly  Ser  Val
145                      150                      155                      160

Gly  Lys  Met  Ser  Val  Glu  Ser  Ser  Ser  Ser  Ser  Ser  Glu  Ser  Glu
               165                      170                      175

Cys  Cys  Glu  Glu  Cys  Gly  Leu  Ser  Ser  Pro  Ser  Thr  Leu  Ala  Ser  Pro
               180                 185                      190

Val  Ser  Pro  Leu  Pro  Pro  Pro  Pro  Ala  Pro  Val  Met  Pro  Ser  Thr
          195                 200                      205

Ser  Gly  Ala  Lys  Pro  Lys  Gly  Pro  Lys  Thr
     210                      215
```

( 2 ) INFORMATION FOR SEQ ID NO:93:

( i ) SEQUENCE CHARACTERISTICS:
  ( A ) LENGTH: 264 amino acids
  ( B ) TYPE: amino acid
  ( C ) STRANDEDNESS: single
  ( D ) TOPOLOGY: linear ( x i ) SEQUENCE DESCRIPTION: SEQ ID NO:93:

```
Pro Pro Pro Pro Thr Pro Leu Asp Ile Leu Ala Gln Ala Val Ser Gln
 1           5                  10                  15
Ala Gly Ile Asp Ser Ser Ser Ala Gly Val Thr Ala Pro Ile Pro Ser
            20                  25                  30
Ser Met Ile Thr Thr Thr Ala Pro Thr Ile Ala Pro Thr Thr Thr Ala
        35                  40                  45
Ile Gln Val Pro Gly Met Gln Ile Thr Ala Ser Leu Gln Gly Thr Pro
    50                  55                  60
Lys Pro Lys Ser Lys Pro Lys Pro Lys Ile Pro Ala Pro Pro Ser Ala
65                  70                  75                  80
Ala Ile Ala Ala Pro Ala Pro Ser Ser Ser Thr Thr Thr Ser Thr Thr
                85                  90                  95
Ser Ser Thr Asn Pro Ala Val Cys Lys Pro Thr Asp Ser Met Ser Gln
            100                 105                 110
Arg Lys Lys Ser Arg Lys Thr Gln His Pro Met Lys Val Ile Ile Lys
        115                 120                 125
Pro Pro Ser Pro Pro Thr Cys Met Leu Lys Pro Ser Glu Ile Lys Gln
    130                 135                 140
Glu Gly Glu Ser Phe Ile Arg Tyr Lys Gly Gln Asp Ile Gln Pro Thr
145                 150                 155                 160
Ser Gly Cys Ile Val Ile Ser Asp Ser Glu Glu Glu Glu Asp Thr Glu
                165                 170                 175
Pro Gly Val Ser Ala Arg Ala Thr Ser Glu Gln Gln Gly Val Gln Leu
            180                 185                 190
Lys Ile Thr Thr Lys Met Ser Gly Ala Ser Gly Gln Ile Pro Met Asp
        195                 200                 205
Ser Ser Ser Ser Ser Ser Ser Asp Ser Glu Cys Cys Asp Glu Cys Ala
    210                 215                 220
Gly Asp His Phe Ser Ser Ala Ser Thr Ile Thr Ser Pro Val Ser Pro
225                 230                 235                 240
Ile His Thr Pro Pro Pro Ala Pro Met Ile Pro Ser Thr Ser Lys Gly
                245                 250                 255
Lys Thr Pro Lys Ala Pro Arg Thr
            260
```

( 2 ) INFORMATION FOR SEQ ID NO:94:

( i ) SEQUENCE CHARACTERISTICS:
  ( A ) LENGTH: 342 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:94:

```
GAGCTCGGAT GAGATCACGA TGATCCGTGG CGTTCACCAC GACAGGCTCC GAGTAAACCA      60
TGGAATCCGA TGCCCCGTAG GCCGAGTCCA GAAACGAGGC GAAGCTGAAC CCAGCTCGC     120
AGATCACGGC GTCGCTGAGC AAGTGGTCTT TCTCCAGACT GCTCAGCTTC TGGCTCGTGT    180
ACCCGAAGTT CTTGTGCGGA GCCAGCTTCA CGGACTGCTG GCTGTCGTTC ACGAACTTCA    240
GGGCCGCTTC GATCAGCACC TTGGTCTCTG AGAAGCGCAC CTGGCACCAC GAAGTGTAAA    300
```

CATAGTAGAA CAGGGTTTCC ACCGCAGGCA CGTACAATCC CC    342

( 2 ) INFORMATION FOR SEQ ID NO:95:

( i ) SEQUENCE CHARACTERISTICS:
        ( A ) LENGTH: 355 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:95:

GAGCTCGAAT GAGATCACGA TGATCCGTGG CGTTCACCAC GACAGGCTCC GAGTAAACCA    60
TGGAATCCGA TACCCCGTAG GCCGAGTCCA GAAACGAGGC GAAACTGAAC CCCAGCTCGC    120
AGATCACGGC GTCGCTGAGC AAGTGGTCTT TTTCCAGACT GGTCAGCTTC TGGGTCGTGT    180
ACCCGAAGTT CTTGTGCGGA GCCAGCTTGA CGGACTGCTG GCTGTCGTTC ACGAACTTCA    240
GGGCCGCTTC GATCAAGCAC CTTGGGTCTC TGAGTAAGGG CAGTTTGGCA CCACGAAGGT    300
TGTTAAACCA TAATAGAACA GGGTTTTCCC ACCCCGAAGG CAAGGTCCAA TCCCC    355

( 2 ) INFORMATION FOR SEQ ID NO:96:

( i ) SEQUENCE CHARACTERISTICS:
        ( A ) LENGTH: 348 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:96:

GCGCGCGGAT CAGATCGCGG TGATCGGTTG CGTTGGTCAC TAAAGGCTCG GAAAAGAGCA    60
TAGATTCGGC AGGTTGGTAA GCCGAATCGA AAAACGAGGC AAAACTGAAG GCCAACTCGC    120
AAACCACCGC GTCACTCAGC AGATGATCCT TTTCCAGACT GCTGAGTCGC TGGCTCATGT    180
ACCCCAAGCG CTTATGTGGC GCCAGCTTCA CCGACTGCTG ACTGTCGTGC ACAAACCGCA    240
ACGCCGCCTC GATCAGCACA CGCGGCTCCG AGAAGCGCAG ATTGACACCA TGACGTGTAC    300
ACGTAGTAGA AAAGCGTCTC GCCGGCCGGC ACGTAGAGCC CTCGCGCC    348

( 2 ) INFORMATION FOR SEQ ID NO:97:

( i ) SEQUENCE CHARACTERISTICS:
        ( A ) LENGTH: 49 amino acids
        ( B ) TYPE: amino acid
        ( C ) STRANDEDNESS: single
        ( D ) TOPOLOGY: linear ( x i ) SEQUENCE DESCRIPTION: SEQ ID NO:97:

Met Leu Ser Asp Ala Val Ile Cys Glu Leu Gly Phe Ser Phe Ala Ser
1               5                   10                  15

Val Phe Leu Asp Ser Ala Tyr Gly Val Ser Asp Ser Met Val Tyr Ser
                20                  25                  30

Glu Trp Pro Val Val Val Asn Ala Thr Asp His Arg Asp Leu Ile Arg
            35                  40                  45

Ala ( 2 ) INFORMATION FOR SEQ ID NO:98:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( x i ) SEQUENCE DESCRIPTION: SEQ ID NO:98:

Met Leu Ser Asp Ala Val Ile Cys Glu Leu Gly Phe Ser Phe Ala Ser
1               5                   10                  15
Val Phe Leu Asp Ser Ala Tyr Gly Ser Asp Ser Met Val Tyr Ser Glu
            20                  25                  30
Trp Pro Val Val Val Asn Ala Thr Asp His Arg Asp Leu Ile Arg Ala
        35                  40                  45

(2) INFORMATION FOR SEQ ID NO:99:

(i) SEQUENCE CHARACTERISTICS:
        (A) LENGTH: 38 amino acids
        (B) TYPE: amino acid
        (C) STRANDEDNESS: single
        (D) TOPOLOGY: linear (xi) SEQUENCE DESCRIPTION: SEQ ID NO:99:

Met Leu Ser Asp Ala Val Cys Glu Leu Phe Ser Phe Ala Ser Val Phe
1               5                   10                  15
Asp Ser Ala Tyr Ser Met Ser Glu Trp Pro Val Asn Ala Thr Asp His
            20                  25                  30
Arg Asp Leu Ile Arg Ala
        35

(2) INFORMATION FOR SEQ ID NO:100:

(i) SEQUENCE CHARACTERISTICS:
        (A) LENGTH: 24 amino acids
        (B) TYPE: amino acid
        (C) STRANDEDNESS: single
        (D) TOPOLOGY: linear (xi) SEQUENCE DESCRIPTION: SEQ ID NO:100:

Met Asp Ala Val Glu Leu Phe Ser Ala Ser Leu Asp Ser Tyr Ser Glu
1               5                   10                  15
Trp Pro Val Asn Ala His Asp Leu
            20

(2) INFORMATION FOR SEQ ID NO:101:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:101:

Met Leu Asp Val Glu Leu Phe Ser Leu Asp Ser Tyr Ser Met Trp Pro
1               5                   10                  15
Asn His (2) INFORMATION FOR SEQ ID NO:102:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO:102:

Met Asp Val Glu Leu Ser Phe Asp Ser Tyr Trp Pro Val
1               5                   10

(2) INFORMATION FOR SEQ ID NO:103:

-continued ( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( x i ) SEQUENCE DESCRIPTION: SEQ ID NO:103:

Met Asp Cys Glu Leu Ser Ala Leu Ser Tyr Trp Pro
1           5                      10

( 2 ) INFORMATION FOR SEQ ID NO:104:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( x i ) SEQUENCE DESCRIPTION: SEQ ID NO:104:

Met Asp Glu Leu Ser Phe Leu Tyr Trp Pro Ala Asp Ile Ala
1           5                      10

STEALTH VIRUS NUCLEIC ACIDS AND RELATED METHODS

RELATED APPLICATIONS

This application is a continuation-in-part of copending United States patent application Ser. No. 08/157,811, filed Nov. 23, 1993, which is a continuation-in-part of abandoned application Ser. No. 07/887,502, filed May 22, 1992, which is a continuation-in-part application of abandoned applications Ser. No. 07/704,814, filed May 23, 1991; and Ser. No. 07/763,039, filed Sep. 20, 1991 entitled. These prior submissions, including any drawings, are incorporated herein by reference in their entirety.

FIELD OF INVENTION

The present invention relates generally to viral nucleic acids and methods of detecting viruses using the nucleic acids.

BACKGROUND OF THE INVENTION

A. Chronic Fatigue Syndrome

Palca, Science, 249: 1240–1241 (1990) and Palca, Science, 254: 1726–1728 (1991) describe attempts to identify a causative agent for chronic fatigue syndrome.

DeFreitas et al., Chemical Abstracts, 114: Abstract No. 205331c (1991) describes retroviral sequences related to human T lymphotropic virus type 2 in patients with chronic fatigue immune dysfunction syndrome.

Gupta et al., Scandinavian Journal of Immunology, 33: 319–327 (1991) describes a comprehensive immunological analysis of chronic fatigue syndrome. The analysis of cell mediated and antibody mediated immunity was performed in 20 patients with chronic fatigue syndrome and 20 age and sex matched healthy controls.

B. Culture Techniques

Werner, Lancet, II: 258–259 (1979) describes the isolation of foamy viruses from patients with de Quervain Thyroiditis and the detection of a cytopathic effect.

DiLuca et al., Virology, 175: 199–210 (1990) describes the replication of viral and cellular DNA in human herpesvirus 6-infected cells and the use of medium RPMI 1640 containing 10% fetal calf serum.

Ablashi et al., International Journal of Cancer, 42: 787–791 (1988) describes the use of human hematopoietic cell lines for the propagation of HBLV (human herpesvirus 6) in RPMI 1640 supplemented with 10% FBS and antibiotics.

Rethwilm et al., Nucleic Acids Research, 18: 733–738 (1990) describes an infectious molecular clone (pHSRV) of the human spumaretrovirus (HSRV). pHSRV derived virus produced foamy virus typical cytopathic effects in susceptible cultures.

SUMMARY OF THE INVENTION

The present invention provides nucleic acids of a novel virus, termed stealth virus, and methods of using such nucleic acids.

The cloning and sequencing of stealth viruses is described in commonly owned international patent application publication No. WO 92/20787, published Nov. 26, 1992, incorporated herein by reference in its entirety, including any drawings. Further sequence data and related information is provided herein, and in Martin et al., The American Journal of Pathology, 145: 440–451, 1994, both of which are incorporated herein by reference in their entirety, including any drawings.

In one aspect the present invention provides a method of diagnosing a stealth virus-associated disease in a human or animal subject suspected of having the disease, comprising detecting in a sample from the subject the presence of a stealth virus nucleic acid.

The term "stealth virus" refers to a virus having all of the following characteristics: (a) the ability to induce a cytopathic effect in fibroblastic cultures, including primary kidney cell cultures, which is characterized by the production of enlarged, foamy appearing cells, including cell syncytia; (b) the ability to produce inhibitory compounds capable of suppressing viral growth; (c) the ability to grow in cells from a plurality of species; (d) the ability of viral-specific typing antisera to distinguish stealth viral infected cells from cells infected with human cytomegalovirus, herpes simplex virus, human herpesvirus-6, varicella zoster virus, Epstein-Barr virus, adenoviruses or human T lymphotropic virus (HTLV); (e) the ability of virus specific nucleic acid probes to distinguish stealth viral infected cells from cells infected with human cytomegalovirus, herpes simplex virus, human herpesvirus-6, varicella zoster virus, Epstein-Barr virus, adenoviruses or HTLV, using stringent hybridization conditions; and (f) the ability to cause disease in an immunocompetent host without evoking an inflammatory response throughout the infected tissues.

The term "cytopathic effect" (CPE) refers to the appearance of rounded, slightly enlarged, refractile cells throughout the culture. In some cultures the CPE progresses to very prominent collections of tightly packed, enlarged, foamy-cell appearing cells, with clearly defined cell syncytia and evidence of considerable cell destruction. Stages between the spindle shape of the normal fibroblasts and the rounded appearance of affected cells can be seen. Several inclusions, consistent with vacuoles, can been seen within the cytoplasm. As their numbers increase, affected cells form several tightly adherent clumps with indistinct cell boundaries. The affected cells continue to proliferate and scatter away from the cell clumps.

The stealth virus preferably has a nucleic acid sequence corresponding to any of the plasmid sequences as set forth in the figures attached hereto or at least 9 contiguous nucleic acids thereof, preferably 12 or 15 contiguous nucleic acids thereof, more preferably 18 or 27 contiguous nucleic acids thereof, most preferably 50%, 100%, 150% or more contiguous nucleic acids thereof. Especially preferred are those with at least 60%, 80%, 90%, 95% or more similarity or identity to the sequences shown in the figures.

Stealth viral nucleic acid may be isolated from a sample of blood or other biological samples including surgical and fine needle aspiration tissue biopsies, post mortem organ biopsies, throat swabs and saliva, urine, cerebrospinal fluid (CSF), other body fluids, blood and blood products intended for transfusion or for in vitro uses, vaccines, foods, and from the environment In preferred embodiments the presence of a stealth virus is detected by a method comprising isolating DNA from the sample, exposing the DNA to a nucleic acid hybridizable to a stealth virus nucleic acid under conditions such that hybridization can occur, and detecting any resulting hybridization. Examples of stealth viral associated diseases include chronic fatigue syndrome, atypical neurological diseases, atypical psychiatric diseases, atypical rheumatological diseases, atypical auto-immune like diseases, and atypical diseases involving liver, testis, ovary, salivary glands, lymph nodes, intestine or any other organ shown to be susceptible to infection with stealth viruses in humans and in animals.

The method preferably involves the step of detecting the level of stealth virus and/or stealth virus associated toxin in a sample from a subject to thereby monitor said stealth virus-associated disease.

The term "chronic fatigue syndrome" (CFS) refers to an illness whose major characteristic is an unexplained fatigue lasting beyond 6 months which results in greater than 50% reduction in an individual's normal level of activity (Holmes et al., "Chronic fatigue syndrome: A working case definition," Ann. Intern. Med., 108: 387–389 (1988); Holmes, "Defining the chronic fatigue syndrome", Rev. Inf. Dis., 13 (Suppl. I):S53-5 (1991); Shafan, "The chronic fatigue syndrome" Am. J. Med., 90: 731–738 (1991)). To establish a clinical diagnosis, the patients should show evidence of suffering at least eight of the following minor symptoms: fever, sore throat, myalgia, muscle weakness (which may be exacerbated by exercise), arthralgia, lymphadenopathy, sleep disturbance, headaches, acute or subacute onset, and neuropsychological symptoms. The neuropsychological symptoms include a difficulty in thinking, dysnomia, confusion, forgetfulness, irritability, depression, photophobia and transient visual scotomata.

In another aspect the invention provides a kit for detecting the presence of stealth virus in a sample comprising in a container a nucleic acid probe capable of hybridizing to a stealth virus nucleic acid.

In preferred embodiments the nucleic acid probe comprises a purified first nucleic acid capable of hybridizing to a second nucleic acid of a stealth virus associated with a human or animal disease in which the first nucleic acid does not hybridize to nucleic acids from HTLV-I, HTLV-II, CMV, HSV, HHV-6, or adenovirus under the most stringent hybridization conditions which allow the probe to hybridize with the stealth virus nucleic acid. The nucleic acid probe may be DNA, such as a cloned stealth virus nucleic acid fragment or a portion thereof.

In another aspect the invention provides an isolated nucleic acid sequence encoding at least a hybridization portion of a stealth virus nucleic acid sequence, preferably as contained in a stealth virus infected MRC-5 cell deposited with the ATCC, and assigned accession no. VR 2343.

In another aspect a method for screening a suspected human or animal source of infection or transmission of stealth virus, or a food or other environmental substance or object suspected as being a possible source of stealth viral infection or transmission is provided and involves assaying a sample from the suspected source of infection or transmission for the presence of a stealth virus nucleic acid.

The summary of the invention described in detail above is not intended to limit in any way the scope of the present invention which is defined in the appended claims.

BRIEF DESCRIPTION OF THE FIGURES

FIGS. 1–11 show nucleic acid sequences obtained from a patient with a stealth viral infection using techniques as described herein.

DETAILED DESCRIPTION OF THE INVENTION

Preferred embodiments of the present invention are described in detail below. However, the following description of the preferred embodiments is not intended to limit in any way the scope of the present invention, which is defined in the appended claims.

The present invention provides several stealth viral nucleic acids and methods for using them, for example to detect the presence or amount of a stealth virus.

Utility

The present invention provides nucleic acids and methods for the detection of a stealth virus. A virus is an infective agent and the stealth virus is associated with disease. The disease may be chronic fatigue syndrome (CFS) or one of several other diseases. Therefore, my invention has broad application to any area in which it is important to detect a stealth virus. Such areas include medical, veterinary, and agricultural diagnostics and industrial and pharmaceutical biological quality control.

Many patients with a stealth viral infection have a stealth virus associated disease. Therefore, the detection of the presence of a stealth virus may allow one to confirm the diagnosis of a particular disease. Thus, those patients may avoid needless treatment, including psychiatric treatment. Indeed, it is useful to detect the stealth virus in order to develop a therapy or treatment for patients with a stealth viral associated disease. For example, in order to develop a vaccine it is useful to first detect the virus.

In contrast, many patients without a stealth viral infection do not have a stealth virus associated disease. Thus, the failure to detect a stealth virus may indicate a psychiatric rather than physiological problem. Therefore, those patients may seek proper treatment, such as psychiatric treatment, rather than pursuing treatment aimed at eliminating or reducing the effects of a stealth virus.

Since the stealth virus is associated with disease, it will often times be useful to detect the virus either in order to eliminate or avoid it. For example, in some circumstances a pure material or sample is desired and it would therefore be useful to detect a stealth virus in the material or sample.

It would be useful to know if a food or beverage contained a stealth virus. One could simply avoid consuming the food or beverage in that case as a matter of prudence in order to reduce the risk of contracting a stealth virus associated disease. Similarly, it would be useful to know if a sample of blood contained a stealth virus. One could then simply avoid that blood in order to reduce the risk of contracting a stealth virus associated disease. Many other potential sources of infection are identified herein. Thus, detecting the virus may allow individuals to avoid the virus and any diseases associated with the virus. In other words, the invention is useful for prevention of disease transmission by identifying potential sources of infection.

CLONING AND SEQUENCING OF RECOMBINANT STEALTH VIRUS DNA

Stealth viruses can be detected and their nucleotide sequence determined using molecular probe techniques. Because these viruses do not normally evoke an in vivo inflammatory response, they can easily go undetected in infected individuals. similarly, even with the culture techniques described supra, it is difficult to obtain high yields of virus for conventional biochemical assays. For these reasons, the detection and characterization of stealth viruses are particularly suited for sensitive molecular probe based assays, including the polymerase chain reaction (PCR). In one embodiment, blood and the subsequent stealth virus culture from the patient D. W., from whom the initial isolate of a stealth virus was achieved, showed a positive PCR assay, whereas control normal individuals and uninfected cultures tested negative. The PCR primers used in the initial molecular characterization of a stealth virus are not necessarily specific for the stealth virus. Rather the primer reactivity with a stealth viral DNA can be the result of cross priming. This can be explained because of the relatively low stringency conditions used in the PCR and in the hybridization assays. When applied to virus infected cultures, this low stringency PCR approach can allow the amplification and subsequent cloning and sequencing of a region of the stealth virus genome.

In a preferred embodiment, cloning of PCR products can be achieved as follows: The PCR products generated in stealth virus infected cultures are blunt-ended, phosphorylated and cloned into pbluescript phagemid (pbluescript SKII [+] from Stratagene, La Jolla, Calif.) as follows: After completing the PCR, 2 unit of Klenow enzyme and 1 uM of each dNTP are added to the reaction mixture. After 30 minutes incubation at 14° C., the DNA is extracted using 100 uL of phenol and of chloroform. The DNA is precipitated using ethanol in the presence of KOAc and glycogen, washed once in ethanol and dried. The 5' end is phosphorylated using T4 kinase and ATP. Following a 37° C. incubation for 30 min., the kinase is inactivated by heating the mixture at 65° C. for 10 min. The reaction products are run in 0.8% low melting point agarose and the band of interest excised. A T4 ligase reaction is performed using purified pBluescript vector, previously cut with EcoRV and treated with calf intestinal phosphatase. The ligation reaction is allowed to proceed during an overnight incubation at 14° C. The enzyme is inactivated by heat (65° C. for 10 min.). Transformation into XL-1 competent cells is achieved by a 40 min. incubation on ice followed by a heat shock at 42° C. for 90 sec. The bacteria are plated on LB agar containing ampicillin, IPTG and X-gal. Colorless colonies are screened for an insert using the PCR product as probed and confirmed using the bacteria as template in the PCR. Sequencing of the insert can be performed using the dideoxy/deoxynucleotide chain termination method of Sanger F. Milkin S. and Coulson AR. 1977. *Proc. Natl. Acad. Sci. USA* 74: 5463–5467. Once the sequence has been determined, highly specific primer sets can be prepared which should give clearly positive PCR responses in blood samples from the patient but not in blood samples from normal individuals.

Thus in summary, to obtain sequence data on new stealth viral isolates, one can begin by testing various PCR primer sets using relatively low stringent conditions. Amplified products can be isolated and tested for specific reactivity with DNA derived from viral infected cultures, compared to uninfected cultures or cultures infected with non-stealth viruses. If the PCR product proves to react specifically with the stealth virus infected cultures, it may be used as a probe. Moreover, using generally accepted methods, including the method outlined above, the PCR product can be cloned and sequenced. Specific PCR assays can then be constructed. Furthermore, the cloned DNA can be used to develop molecular probes for in situ hybridization. Once cloned DNA is available, one can proceed to the cloning and sequencing of the entire genome of the viral isolate. A detailed example of this approach is provided in Section 9.

Reactivity with various primer sets provides a method to distinguish among different isolates of stealth viruses. For example, PCR performed using the SK43' and SK44" primers on a stealth virus culture obtained from a CFS patient L. B., required that both primers be used. A 600 bp product was cloned and sequenced. Analysis of the sequence showed the incorporation of the SK43' primer at one end and of the SK44" primer at the other end. The intervening sequence showed no relationship to the sequence of other known viruses or to the amplified sequences obtained using PCR with these primers on the stealth virus culture from patient D. W. (see Example 13, infra).

On the other hand, PCR reactive pattern seen on the stealth virus culture from patient D. W., was similar to that found on the stealth virus culture from the patient B. H. Since the general nature of the CPE is a common characteristic of stealth viruses, it is predicted that there will be a common genetic region. Individual isolates appear to have unique genetic regions. Sequencing of such regions, will allow for the development of isolate specific PCR assays. These assays will be extremely useful in tracing the epidemiological spread of infection between individuals and between humans and animals. PCR against a common region will enable detection of multiple isolates.

The sequences within the cloned plasmids can be used to construct PCR primers that will read out through the 51 or 31 ends of the cloned sequence. When used in various combinations, these primer sets will yield additional PCR products that will bridge the regions of the stealth viral DNA between the regions presently sequenced. These additional products can be cloned and sequenced. Using this approach, additional DNA sequence data will become available on the isolated stealth virus from patient D. W.

In another approach, plasmids containing cloned regions of the stealth virus from a patient can be used to select clones derived from a genomic library obtained from the infected cultures. Genomic libraries can be created in Lambda vectors and the resulting clones hybridized with radiolabeled cloned inserts obtained from the pbluescript vectors so far isolated. The selected clones can be sequenced and additional PCR primer sets established.

Using these approaches, the entire sequence of the stealth virus from patient D. W. can be derived. Furthermore, the molecular techniques, beginning with low stringency PCR using various primer sets, including the SK43' and SK44", and the CMV and EBV reactive primer sets, can be applied to other viral isolates, to yield comprehensive sequence data on other isolates.

The cloned plasmids can also be used to generate transcripts for use in in situ hybridization assays on infected cells both in vitro and in vivo.

The present invention is also useful in a variety of other ways readily apparent to those skilled in the art.

EXAMPLES

This invention will be more fully understood with reference to the examples which follow. The following examples are intended to illustrate the invention, but not to limit its scope which is defined in the claims appended hereto. The following examples are presented to illustrate the advantages of the present invention and to assist one of ordinary skill in the art in making and using the same, but are not intended in any way to otherwise limit the scope of the disclosure or the protection granted by a letters patent hereon. In the following examples, the detection of the cytopathic effect was recorded as follows. This minimal level of CPE has to be transferable to secondary cultures for the culture to be recorded as a true positive (+). A + (one plus) positive effect indicates the presence of multiple enlarged refractable cells forming small clumps with indistinct cell borders are clearly seen in the cultures.

A +/− (plus/minus) or equivocal effect refers to a minimal change in the culture in which the rounded cells are either not enlarged or non-refractile (possibly dead). Less than 4% of cultures from CFS patients have been recorded as equivocal, either because the CPE has been restricted to only a small region of the culture, or because it has failed to recur on secondary passage. These cultures have been excluded from analysis.

A ++ (two plus) strong positive response is recorded when vacuoles are clearly identified within enlarged, rounded, refractile cells and/or when multiple foci of cell clumping and/or destruction are apparent which are ringed by cells described as having a positive effect. A +++ (three plus) very strong positive effect refers to extensive ++ cellular changes throughout much of the culture and/or the appearance of large refractile vacuolated, foamy syncytial cell formation. Typical CPE's are shown in Patent Cooperation Treaty publication number WO 92/20787.

A benefit of using multiple indicator cell lines, is that the CPE appearances in the different cell lines sometime complement each other. For example, cell syncytia are usually best observed in monkey kidney cells. The smaller rounded refractile cells are usually best observed in the human fibroblasts. In over 80% of positive cultures, the CPE is clearly observable in at least 2 of the 3 cell lines. As with any viral induced CPE, it is important to confirm transmission to fresh cultures. In recipient cultures, the stealth virus induced CPE generally develops more rapidly than in the primary culture with at least the same level of intensity.

Although the appearances of the CPE share some features in common with those associated with cytomegalovirus (CMV) and herpes simplex virus (HSV) infection, stealth virus cultures can be readily distinguished from cultures harboring these viruses. The CPE from HSV is much more rapid, occurring in a matter of days. The destruction is greater with large masses of dead cells. The CPE from CMV tends to initially develop in smaller, looser clusters and evolves more slowly than observed with stealth viruses. The intracytoplasmic vacuolization and syncytia formation are far less prominent with CMV than with stealth viruses. The stealth virus infected cells give more the appearance of "foamy cells" than does CMV. Indeed, with some stealth viral cultures, there appears to be a marked accumulation of lipid-like material attaching itself to the wall of the culture tube. Human CMV does not infect monkey derived cells.

Example 1: Culture Of Stealth Viruses—7% FCS and Frequent Refeeding

Culture tubes containing human fibroblast (MRC-5), primary human foreskin fibroblast (MRHF) and rhesus monkey kidney (RMK) cells are each inoculated with a cellular mixture of the buffy coat granulocytes and ficoll-hypaque separated lymphocytes derived from approximately the equivalent of one milliliter (ml) of heparinized blood. Typically, 5 ml of blood collected into a "green top" heparinized tube, are layered onto 3 mls of a ficollhypaque lymphocyte separation medium. Following 20 minutes centrifugation at 1,500 rpm, the lymphocyte, which collect at the plasma:ficoll hypaque interface, and the "buffy coat", present on the top of the erythrocyte layer, are collected into approximately 1 ml. An effort is made to minimize the number of erythrocytes in collecting all of the visible buffy coat.

The cell mixture is washed once in 1 ml of 199 medium containing 7% FCS and resuspended into 1 ml. Aliquots of 0.2 ml of the cells are added to culture tubes containing 1 ml of 199 medium plus FCS. The tubes are placed in an incubator at 37° C. for 45-60 minutes. The are then rinsed to remove macroscopically visible erythrocytes and other non-adherent cells. Rinsing (washing) consists of emptying the fluid content of the culture tube by decanting or by aspiration; adding 2 mls of medium or phosphate buffer saline; rocking the tube for several seconds to suspend erythrocytes; decanting the tube again. This important step is performed 2-10 times or until there are no macroscopically visible erythrocytes.

Two mls of medium with 7% FCS, are added and the tubes returned to a 37° C. incubator. Cultures are maintained in the incubator at 37° C., with refeeding (replacement of old medium with medium) at 24, 48 and 72 hours. The tubes are examined microscopically after the 24 hour refeeding and, if residual erythrocytes are present, the tubes are rinsed in a manner similar to that performed at the 45-60 min. step. The tubes are refed three times each week by replacing the old medium with 2 mls of fresh medium. This procedure is designed to reduce the accumulation of a toxic component in the culture medium which tends to suppress viral growth. The tubes are examined three times per week for evidence of CPE (CPE). CPE is generally recognizable between 2-3 weeks after culturing.

A lack of regular refeeding of the cultures can result in a tendency for the CPE to abort and not to progress. This effect is not seen with CMV infected cultures. In unfed stealth virus cultures and even with regular refeeding, one can observe a toxic effect on many of the remaining cells. Culture cells appear to lose a degree of vitality and become duller in appearance compared to control cultures. The fibroblasts can assume somewhat of a pavement appearance, instead of the elongated shape. Some of these changes can be mimicked using 5 nM of the polyether marine toxin okadaic acid (Cohen et al., "Okadaic acid: A new probe for the study of cellular regulation" Trends Biochem. Sci., 15: 98-102 (1990). CMV positive cultures do not demonstrate the toxic activity such as that observed with stealth viruses.

Moreover, the detection of CPE from CMV is readily seen in cultures containing only minimal essential medium and 2% FCS even without regular refeeding of cultures. This is the routine medium used in most virology laboratories and can be contrasted with the more enriched medium 199 and 7% FCS that is used to culture stealth viruses. The more enriched medium and the higher concentration of FCS, help to neutralize the toxic, stealth virus growth inhibiting effects, which would otherwise occur in the cultures.

Although presumptive of stealth virus infection, the CPE appearance may require additional confirmation for a definitive conclusion of stealth virus infection.

Example 2: Viral Enhancing Medium (VEM)

In preparing viral enhancing medium a known positive CMV culture was passaged into a flask of MRC-5 cells and fed with X Vivo-15 medium. The cultures were observed for the development of CPE. The culture medium was changed at 1 week when approximately 50% of the cells showed signs of CPE, but before there was marked cellular destruction. This newly added medium was collected 48 hours later. It was centrifuged at 800 g for 20 minutes to remove cellular debris.

The medium was transferred to new tubes which were placed in a beaker containing water. The water was heated to boiling for 20 minutes. After cooling, the medium was filtered through a 0.45 micron Millipore filter. This material was diluted 30:70 into regular X Vivo-15 medium to constitute a "lot" of CMV derived VEM. Each lot of VEM is tested to confirm: i) that it does not contain any residual live CMV by adding the medium to MRC-5 cells; and ii) that it can promote the development of the CPE induced by the prototype stealth virus by comparing the growth of the stealth virus in RMK cells containing VEM with that of similarly inoculated cells containing X Vivo-15 medium without supplement.

VEM has been tested on ten additional stealth viral isolates and clearly enhanced the growth of all of them. Two of these isolates are known to share CMV related sequences with the prototype stealth virus. Another isolate (from patient G. P.) shares antigens with HHV-6, rather than CMV, and is considered an HHV-6 related stealth virus. Another isolate appears to have an adenoviral sequence. The use of VEM also reduced the time for a discernible CPE using fresh blood from two newly cultured CFS patients. It enhances the intensity of the CPE and reduces the tendency for weekly positive cultures to revert to near normal appearance. VEM has also worked well in the cultures from the tissues of cats inoculated with the prototype stealth virus from patient D. W. allowing for clearly positive culture results. VEM obtained from HHV-6 (strain GS) infected fibroblasts was similarly tested for its ability to promote the growth of CMV and HHV-6 associated stealth viruses. It worked well with both viral types with a discernable advantage on the HHV-6 related stealth virus from patient G. P., compared to the CMV related stealth virus from patient D. W.

As a specific example, cultivation of a prototype stealth virus isolated from a CFS patient (initials D. W.) can be greatly enhanced by the addition to the culture of VEM comprising a 30% concentration of boiled, filtered supernatants from cytomegalovirus (CMV) infected cultures. This addition helps remedy a deficiency of viral growth enhancing components coded for by the immediate-early (I-E) and probably other CMV related genes which are not detectable in the stealth virus from this patient.

Example 3: Viral Enhancing Medium and Pre-Culture Centrifugation

Human fibroblast (MRC-5), rhesus monkey kidney (RMK) and rabbit kidney (RK) cell lines were obtained from BioWhittaker, Inc., Walkersville, Md. The tubes were placed in a 37° incubator. The next day, the Delbecco's modified Eagles medium containing 2% FCS is replaced by medium 199 plus 7% FCS. The tubes were used to provide indicator cells for stealth viral cultures within the next 7 days. To establish the viral cultures, the contents of a single test tube of each of the indicator cell lines to be used were scraped from the tubes and washed once in X Vivo-15 medium.

The cells were gently resuspended into approximately 0.5 ml of medium and transferred to 2 ml Eppendorf tubes. Prior to this step, ficoll-hypaque separated lymphocytes from either heparinized or citrate treated whole blood, were obtained by layering 5 mls of anti-coagulated blood onto 3 mls of ficoll-hypaque solution in 12 ml conical tubes. The tubes were centrifuged for 20 min at 800 g. The banded lymphocytes were aspirated and transferred to a fresh tube for washing in 10 mls of medium. The lymphocytes were resuspended in approximately 1 ml.

Aliquots of 0.2 ml of the lymphocytes were added to each of the Eppendorf tubes containing the harvested fibroblast indicator cells with a final aliquot stored for future studies.

The lymphocyte-fibroblast cell mixture was centrifuged at high speed for 3 minutes. The tightly-packed cell pellet was gently resuspended and transferred back to the tube from which the fibroblasts were originally obtained. Two mls of VEM (X Vivo-15 medium supplemented with 30% CMV supernatant) were added and the tubes are placed in an incubator at 37° C. The tubes were refed with VEM at 48 and 72 hours and thereafter 3 times per week.

Control cultures in which either lymphocytes from other individuals are used, or the fibroblasts were processed but with the exception of no added lymphocytes, were fed in parallel with the test cultures. Note, in this revised protocol, buffy coat granulocytes are no longer routinely used since the contaminating erythrocytes tended to clump about the fibroblasts during the centrifugation step and were difficult to remove in subsequent washing of the cultures. Granulocytes may be an important source of virus in some patients. If this proves to be so, leucocyte rich plasma will be obtained by dextran precipitation of the erythrocytes from anti-coagulated blood, or as an alternative, modifications of the ficoll-hypague separation method can be used which will separate both lymphocytes and granulocytes away from the erythrocytes. For example by using PMN isolation medium from Robbins Scientific Corp., Sunnyvale Calif. CSF and tissue extracts can be used in place of the lymphocytes.

The cultures were observed for a CPE which characteristically consists of rounding and swelling of the cells, formation of cell clumps which tend to disperse, appearance of intracellular granules/vacuoles and an overall foamy cell appearance often with prominent accumulation of lipid-like material.

TABLE 3

Examples of the Enhanced Recovery and More Intense Development of CPE by a Stealth Virus from a CFS Patient Using Pre-Culture Centrifugation (PCC) and Viral Enhancing Medium (VEM).*

| Method of Culturing | Time to CPE** | Intensity of CPE |
|---|---|---|
| Patient 1 | | |
| Medium 199 + 7% FCS | 45 days | 1–2+ |
| PCC and VEM | 12 days | 3+ |
| Patient 2 | | |
| Medium 199 + 7% FCS | 28 days | 1–2+ |
| PCC and VEM | 16 days | 3+ |

*Medium X Vivo-15 containing 30% supplement of boiled filtered supernatant from a CMV culture also grown in medium X Vivo-15.
**Results are in RMK cells. Enhanced growth was also seen in MRC-5 cells.

Growth of Stealth Virus in Insect Cell Line

The Spodoptera fruiperda derived ovarian cell line Sf9 that is used routinely for the propagation of recombinant insect baculovirus was obtained from PharMigen, San Diego. It was maintained at 27° C. in Grace's medium with 10% fetal calf serum. The stealth viruses from patients D. W., G. P., K. E. and B. B. were passaged into the insect cell line using 0.1 ml of cell-free supernatant from an infected MRC-5 human fibroblast culture. CPE was clearly seen within two days and progressed over the next several days.

The infected cultures showed enlarged foamy cell syncytia. Virus infectious for MRC-5 and for insect cell cultures was recoverable from the insect cell cultures to a dilution of $10^{-3}$ ml. Electron microscopic examination of the insect cultures infected with the virus from patient D. W. showed abundant herpes-like viral particles. In control studies, neither cytomegalovirus, human herpes virus 6, varicella zoster virus or Epstein-Barr virus induced CPE in the insect cell line; nor was infectious virus recoverable from these cultures.

EXAMPLE 5: CLONING AND SEQUENCING OF DNA IN STEALTH VIRUS ISOLATED FROM CFS PATIENT D. W.

5.1 MATERIALS AND METHODS

PCR is performed on tissue culture cells as follows: Cells from a single culture test tube are scraped into PBS, washed once and digested with 100 ug proteinase K. The subsequent procedures are identical to those used for proteinase K digested whole blood. Labeling of PCR products was performed using the random primer method described by Feinberg AP and Vogelstein B; A technique for radiolabeling DNA restriction endonuclease fragment to high specific activity. *Anal Biochem.* 137: 266–269, 1984; using reagents from US Biochemical Cleveland, Ohio, to a specific activity of approximately 109 dpm/ug.) Coning of PCr products is achieved as follows: The PCR products are blunt-ended, phosphorylated and cloned as follows: Following completion of the PCR, 2 units of Klenow enzyme and 1 uM of each DNTP are added to the reaction mixture. After 30 minutes incubation at 14° C., the DNA is extracted using 100 uL of phenol and of chloroform. The DNA is precipitated using ethanol in the presence of KOAC and gylcogen, washed once in ethanol and dried. The 51 end is phosphorylated using T4 kinase and ATP. Following a 37° C. incubation for 30 min., the kinase is inactivated by heating the mixture at 65° C. for 10 min. The reaction products are run in 0.8% low melting point agarose and the band of interest excised. A T4 ligase reaction is performed using purified pbluescript vector, previously cut with EcoRV and treated with calf intestinal phosphatase. The ligation reaction is allowed to proceed during an overnight incubation at 14° C. The enzyme is inactivated by heat (65° C. for 10 min.). Transformation into XL-1 competent cells is achieved by a 40 min. incubation on ice followed by a heat shock at 42° C. for 90 sec. The bacteria are plated on LB agar containing ampicillin, IPTG and X-gal. Colorless colonies are screened for an insert using the PCR product as probed and confirmed using the bacteria as template in the PCR. Sequencing of PCR products is performed according to the dideoxy/deoxy nucleotide termination method of Sanger F. Milklen S and Coulson AR. 1977. *Proc. Natl. Acad. Sci. USA* 74; 5463–5467.

5.2 RESULTS

PCR assays, using the HTLV tax gene primers SK43' and SK44", were performed on virus infected MRC-5 and MRHF cultures derived from CFS patient D. W. The HTLV primers consistently yielded an unexpectedly large band when examined by ethidium bromide stained agarose electrophoresis. The band had an apparent size of 1.5 kbp. The 1.5 kbp band was clearly distinct from several smaller products generated in the same PCR and from the 158 bp product obtained using the tax primers on HTLV-I infected cultures (FIG. 4). The individual HTLV tax primers SK43' and SK44" were tested in PCR assays on viral infected cultures. As has been noted in other PCR assays using single primers (Wang W P, Myers R L Chiu I M. Single primer-mediated polymerase chain reaction: application in cloning of two different 51-untranslated sequences of acidic fibroblast growth factor MRNA. *DNA Cell Biol.* 10: 771–7, 1991.), the SK44" primer used as a single primer was as effective in generating the 1.5 kbp band as was the combination of the two primers. Similarly, the SK43' primer set used alone could generate a discrete PCR product from the stealth virus infected culture from patient D. W. (see infra).

The 1.5 kbp PCR product(s) generated from the virus infected culture was excised from the agarose gel, labeled with alpha-32P DCTP and used as a probe. It hybridized with extracts from infected cultures from the patient and with extracts from a positive culture from a patient (B. H.) who is described infra. It did not hybridize with material extracted from uninfected MRC-5 cells or cells infected with CMV, HSV, HHV-6, HTLV-I or HTLV-II. As expected, PCR generated products using the tax primers on the infected cultures hybridized strongly to the labeled probe.

Cloning and sequencing of individual recombinant plasmids showed that there were two distinct PCR products generated in virus infected cultures using the SK44" tax gene reactive primer. one product cloned into plasmid number 15-5-2 contains 1484 bases while the other product, cloned into plasmid number 15-5-4, contains 1539 bases. The sequences of the plasmid inserts are shown in Tables 1 and 2. Both inserts are flanked by the EcoRV cloning site (GAT/ATC) and the SK44" primer used in the PCR. Computer assisted analysis (FastA Program available from Genetic Computer Group, Wisconsin) showed no apparent homology between the sequence in plasmid 15-5-2 with any viral or nonviral sequence contained in the entire GenBank data base (updated as of 12/91). Analysis of the sequence of plasmid 15-5-4, however, showed highly significant, partial, homology with the AD169 strain of human cytomegalovirus (GenBank Accession number: X17403). FastA analysis revealed a 58% identity over a 1,201 bp overlap. The overlapping regions extended from nucleotide 140 to 1,311 of the insert and nucleotide 44,705 to 45,891 of the CMV genome. This region of the CMV genome is contained within the transcripts of both the UL33 and UL34 genes and is part of the protein coding sequence of the UL34 gene which extends from nucleotide 44,500 to 46,011 (Chee M S, Bankier A T, Beck A T, et al. Analysis of the protein coding content of the sequence of human cytomegalovirus strain AD169. 1990 *Curr. Topics Micro. Immunol.* 154: 126–169. Welch A R, McGregor L M, Gibson W. Cytomegalovirus homologs of cellular G protein-coupled receptor genes are transcribed. 1991. *J Virol* 65: 3915–3918). No significant sequence homologies were identified for the sequence beyond the region of overlap with the UL34 coding gene. In particular, the flanking regions adjacent to where the primer had been incorporated bore no significant relationship to the sequence of HTLV.

The sequences of the two plasmids were used to design sets of virus specific primers and detecting probe for use in the PCR. The regions used are indicated in Tables 1 and 2. These primers gave no detectable products when the PCR was performed on blood samples from normal individuals or on uninfected cultures or cultures infected with CMV, HSV, HTLV-I or HTLV-II. Strongly positive PCR responses, shown by a well defined band of the expected size on agarose electrophoresis and by Southern blot hybridization with labeled probe, occurred when the PCR was performed on viral cultures derived from the patient D. W. even over a 3 log dilution. All six independently derived cultures from patient D. W. gave strong positive PCR. Moreover, frozen blood samples collected from patient D. W. over an 18 month period tested positive. FIG. 6 shows the banding pattern of the PCR products obtained using seven stored blood samples. These data establish that the virus was derived from patient D. W.

The SK43' primer used by itself was also able to generate a PCR product of 660 bp. The sequence of this product, which shows no significant homology with known viruses is shown in Table 3.

It is possible to screen multiple primer sets for such cross-reactivity. As a further example, a positive PCR can be obtained from the stealth viral culture of patient D. W. using a primer that corresponds to a region of the Epstein-Barr virus. This product has been isolated, cloned and sequenced. Its sequence is shown in Table 4.

5.3 CONCLUSION

The available sequence data confirm that I have isolated a novel virus with at least some homology with a herpesvirus. To date, I have not identified known retroviral sequences in the virus. Using the available virus-specific plasmids, I am currently proceeding to isolate additional regions of the viral genome for sequencing. The example shows the use of PCR primers, which fortuitously bound to the viral template DNA, to derive clones and sequence data from stealth virus infected cultures. The same approach can be taken in using paraffin-embedded tissue sections or other nonviable samples containing stealth viral genomes.

The sequence is shown as read from the T3 sequencing primer of the plasmid. SK44" primer sequences are indicated by bold type. The underlined segments show the positions of the primers and the detecting probe which were synthesized to enable plasmid-specific PCR amplification. A second plasmid (15-5-1) gave essentially identical results, as did sequencing of a cloned Pst I digest of the PCR products.

TABLE 1

Sequence of PCR amplified product obtained from virally infected cells and cloned into plasmid 15-5-2.

5'-GATGAGCTGACAACGCGTCCATCGGAACATGACAGCACGGAAAC

TACCCCTATCTTGTCCGCCTCGCACAAACCCAGCACGAACACACCCCCGG

CTGTCTCACCTAAGCCAACCATCTCCAACGGCACCAAAAAGCCCATTGTT

CCACCAAAACCTAAACCGAAGCCAAAGCCGACGATGCTCCAGTTCCCCGC

ACCCAAAAGCGCCAGACCACGCCCAAGAACACTCAAAGTCCCAAAGTGTT

TACTTTTAACGAGCGTGACATAAGAAAGCACAAAGAAGAGATGGGCGCGG

AGGCCACGAAACCTAGAATCATCCATCACACAGAAGACAGAACCACCGTT

GACAGCGTCCTAACGCCGCTACTGCCACCTCCACCGCCAGCTCCCCGACG

GTATCAACATCGCGGGTGCCAGTGATGATTCCCTGGGACAACACGCAATC

TCCCGCGAAGATGAGTCCCTGGAAAGACACTTGCGAATCCCTGCCCACGG

AGCTGGACCCTTGGGAGTTTAGGCCCCGCCGTGGTTGTAGTAAAAAGAAC

TTGGACTGTCAATCAAACTGCAGATTGTATAGCTATTTAAACTTTATTTC

TGTATATATGTGTAAATAATAAATTTATTCCTCGTATCACACATCTGCAT

CCTGGTCATTCACATCTAGTATTCGCAGCGCAATTCGGGGCCCGGGAGGG

TGCATCATGGCGTCCGGGGCTATCTCTTCCATGATTAAGATAATCTCATC

TCCCAACGGAGGCCTGTTTTCCTGGTCCTCAGCCTGTATTTCCATAGCGA

TCTCTACCACCTCAGCCACCTCGGGAGGAAACTGCAACGGCTGGATCTGC

AGTTGAAGCTGCTGTCGTTGCAGATAGTTCTGAAACAGTCTCCGCCGAGC

CCGAGGAGCATACATGCCTAGAGGGCGATGGGCAGGTTGGTTTAAACGAT

AAAACGAAGCCCGGATAGAAGGCATGAGACCGCGGACGGCCTCTGATAAG

AGGGGATCGGTGCTGCCTCCCATAGTGCCAGTAAGATTCTGGGAGAGTAG

ACATTCCTAAATACTAGCCTGGATCTGACGTCAACACTATGATTCACGCC

CAATTCCACCCACAAAGCCCGTTAGAATACCAGACAACGTCCCCGTTAGT

GATGCCACCCACACAAGATATTTAATGATAACAGAGTTTCAGACCGCCTT

TGTTGAATCGATTCCAATACCGGCATCATGAGGAATCTACAGCTGATCGC

AACTTTGCTAGTTATCGGTTTGGTGGCAGTTCATGCCATCCCCAGGTTGG

AATATGTAACCATATATATCGCGCCCTAGTTATAACCATATTTGACCTGA

AATACTAATGATTCTTTCCTCTCACATGTGCAGGAGAACCACAGATGATA

ATAAAAAGACAACAAACTCAGACTTAAGCAACCAGACCGACGGTGGCGCT

GGCTTCGGCAGCACATACGATGGACGCGTTGTCAGCTCATC-3' SEQ ID NO: 1

TABLE 2

Sequence of PCR amplified product obtained from
virally infected cells and cloned into plasmid 15-5-4 and
comparison with the sequence of CMV.

```
                    10
5'-GATGAGCTGACAACGCGTCCATCGGCCAGATACATAAGTTTACACTCACTGGTACTTGTC

5'-GTGGCGCCCCGGCTTCATTATAACGCCACGTCGGAGCCCCTGCGCGCCACAACGCCGTCC
  44570

70
ACTCACTTGATCACTTTGCTGCGGACGTGACGGCCAATCGTTTCGGGCAGGAGTGGCCAA

GGCGCAACTTCTGTCTCGGCACGGTACGATAAAAACAACGTCCCCCGTCGACGTTGTTTT
44630

130
ACGGCATTATAACGAAACGCCGACCGGGGCCACACGCCAC-TTGGAACGCCGCCGTTAG

CTCCGAGCGGTGATCGTTCCCGTCCCTCTCCTCCCTCCGCGGCCCCCACGGCGGCGGCCT
44690

190
TCCTTTTTTCAACGGTACGATATCGG--CAATCCCCAT-GAC--TATGAACATAATTATA

GCTCGCACGGACCTATACTATTACCGCCCGACCGCCGTCGTCGTCATGAACTTCATCATC
44750

240
ACCACCCGCGAATTCTCCAATGACGAATCCGTCACAGAGAG-CACGGAACCGCAAGACAA

ACCACCCGAGACTTCTTCAACGACGATTCAGTC-CTGCGAGCCGCCGAGATGCGTGACAA
44810

300
CGTTGCCAATAACCTTTCTAAAGCTTACCGAGGTACGATTCGCGCGGAAGGTAAGAAGAA

CGTGGCAGGCTCGATTTCCAAAGCTTACCGAGGTACGATTCGCGCGGAAGGTAAGAAGAA
44870

360
ACTGCTTATTCGCAACCTG--CCTGCC-ACTTTCGGCTGCACTCGCCGCAACAGTAATTT

GCTGCTGCTGAAGCACTTGCCCGTGCCGCCCGGCGGCTGCTCGCGCCGCAACAGCAACCT
44930

420
ATTTATATTTTATAACGACCGGACTATCGAAAGTTCCATCAAGGCATCATACAGTTAAA

CTTCGTTTTCTGCACCGAGCGCGACTACCGCAAGTTCCACCAGGGCATCGCACAGCTCAA
44990

480
ACGAACTCGCACGCGAGTTGATTCATCACAGATCGTGAACGTTACAAAAAATATAAAGTC

GCGCGCGCCGGCCGAACTGGACCGCCACGAGATCCAGCAAGTCACGGCCAGTATCCGCTG
45050

540
TCGACTGCAACCGCACAAT-CAAGACCCGCCGCTAGCCGGCGGGC-AGATCCAAACCACC

CCGCCTGCAGCC-CAGTCTCCGCGAGCCGCC-CACGCCGGCCGACGAGCTGCAGACGGCT
45110

600
ATCTCGCACGTCTGCACTCTGTTCAATCACCTCGTGTTCACGGCTCAGCTCCGTCATTAT

GTGTCGCGCGTGTGCGCGCTCTTGAACCAGCTGGTTTTCACGGCCCAGCTGCGCCACTAC
45170

660
TGCGAAACTCACGAACAAGTTGTCTTGTACGCAAGGGACGAGCTCACCAAACGTTGCGGA

TGCAGACACCAGGACAAGGTGGTGAGCTACGCGCGCGACGAGCTGACTAAACGCTGCGGC
45230

720
GACAAGTCGGCGCTCGGGACTCACACTCACCGACTCATTCCGCTCTTGGATCACGACAAC

GAAAAATCGGCGCTGGGCGTGGAAGTGCATCAACTGGTAGCCCTGCTGCCACACGAGCGC
45290
```

TABLE 2-continued

Sequence of PCR amplified product obtained from
virally infected cells and cloned into plasmid 15-5-4 and
comparison with the sequence of CMV.

```
                   780
CATCGCGAACTGTGCAATGTGCTGGTCGGCCTGCTACACCAAACACCCCACATCTGGGCC

CACCGCGAACTGTGCCACGTCCTCATCGGCTTGTTGCACCACGCCGCACATGTGGGCG
45350

840
CGTTCCATCCGTCTTATCGGCCGATTAAGAAACTATCTACAACAGAAGTTTCTCAATATC

CGCTCCATCCGTCTCATCGGACACCTGCGCCACTACCTCCAGAACAGCTTCCTACACCTG
45410

900
TTGGTGGATAGCGGACTCCAGATCGATAGTCTTTTTGAGGCTTGTTACCACAGCGAACGG

TTCATCAACTCAGGTTTGGATATCGCACAAGTTTTCGACGGCTGTTACCACAGCGAGGCC
45470

960
TACCGCTTGCTGTTCCAGATCGAAAAAACGAACTCCACCCCTAGCTCTCTAGCCTGTGCA

TACCGCATGCTCTTCCAGATCGGTCATACGGACTCGGTGTCGGCGGCCCTGGAACTCTCA
45530

1020
AGCACCGTTTTACCTGTCGGTGAAAACGAAACTGAAGGCACACCTTGTCCCGCCGTGTATT

CACGGCG---CGGCGGCCGGGCCGCCCGAGGCCG-ATGAAAACAACGACGAGGGAGAGGA
45590

1080
TAATGAAATAATAAAATGGTTCTCATGAATAAGACGGTCTTAGTTTCGTTTTTGAA--AG

GGACG--ACGACGAGCTCCGTCACAGCGACCCGGCGCCGCTTCACGAGTCCAAGAAGCCC
45650

1130
GACAAGTATGAGTGTCCCCCCACAC-ATCCCCGCCT---TGGCCGTGGACTCGAG----C

CGCAACGCCCGTCGTCCCCGCACACGCGTCCCGCCTCACGAGCAAAAGCCCGAAGAAAAC
45710

1190
CTGAACTTTCGTGCGCACCTGTTT----TCTG-ACCACAACCGACACTTTCTAGTCGATT

GACCAGCAAGAAGACGACCTGTTTCCCTCCCTGCAAGGCAACCGCACCATTCCTG-CG-CC
45770

1240
TAGTAACCCAAAGCTGCAGCGGCTATGTGGGACTG--TGTAACGCCGGAATTCCCATCCC

CAGAACCCTCCGTCTCCAACGACGACG-GCAACGGCGGCGAACGCTGCGACACGC-TAGC
45820

1300
CACCTATGTACTGGAAACGCTAATTGACTTTCAGGTTCCAACCACATACACGAAAATTAA

GACCGCCCTGC-GGCATCGCGCCGACGAAGAAGACGGACCTCTAGCCAGCCAGACCGCTG
45880

1360
GCCCATTGCCGTAAAAGTGCTAAAAATCTGTATTCTGGCTAACTACCTAAAAAACAGTAA

TGCGGGTCGCCGCGACCCCCTCACCTTCAGTCACCCCAGCCCTTACCCCCGTCACGTCCC
45940

1420
AGAATTATGGATTGATTTCAAAGCTAACCTAGACGAGATTAATTCTGGTGCAAATAAGCA

CCATAACCCCCGTTGTGTATTTAACGTCACTGGAGGACAATAAAGCGTTGATTTCTCAACT
46000

1480
AAGACTGTACAGAGGCTTTTACAAACTATGTCGTGATAAAAACTCGATGCACGCGTTGTC

TCCGCTCTGGTTTTGGTTTCGTTTTCAAAGGGAGCCCCATCATGGCCCAACGATCGCGAG
46060
```

TABLE 2-continued

Sequence of PCR amplified product obtained from virally infected cells and cloned into plasmid 15-5-4 and comparison with the sequence of CMV.

AGCTCATC-3
CCCCATCC-3

The upper row in each pair of sequence is that of plasmid 15-4-4 read from the T7 primer. The lower row in each pair is that of human CMV (Genbank accession number X17403). The nucleotide numbers are shown. The SK4411 primer sequences incorporated into the plasmid are indicated by bold type. The underlined segments show the positions of the primers and the detecting probe which were synthesized to enable plasmid-specific PCR amplification. A second plasmid (15-6-1) gave essentially identical results, as did sequencing of a cloned Xho I digest of the PCR products. Note The sequences identified in this viral isolate are present in some but not in the majority of other cultured stealth viral isolates.

TABLE 3

Sequence of PCR amplified product obtained using SK43' primer on viral culture from patient D. W.

5-
GGAATTCGATCGGATACCCCGTCTACGTGTATTAATATTACATAAAATAGGCTTTTTTTT

AAAAAAAAGAAAAGACATTTTTCACTAATGGTGTCATATCATTATAATAAACCTTGTTTT

CATCAGGAAGGTATAAAAACAAATTCATATGCACTAAATAATATAGATTCAAAACAAATA

AGGCAAAAATCAATGGCAACAGAATAAGCATATATATAAACATGGTGAAAAATTACATAT

AAACACCAAGAATGTGGAAGATTTAGCTGTGATTAGCAAATTTTGCCTAATGGATATATA

TGTATAAACTTGTCCCAATATCTACAGAGTACTCATTCCTATCAAACACAAATAAAACAG

TTCTTAAAAATTCAGTACATATTGTGTCAATTTTAAAAATAAGCTTCAAAGTTTTGATAC

TATAATTTAGAAACTATCTCGAGGGAAATAATATAAATAGTTTAAATAAAAGTGAGGTGA

AACTAATGTATATTTAGATGAAGCAGTATAGTTTTAAATTTACATATTATAAAAGAAGAA

TATTAATGAACTAAACATACATCCTAAGAAGTTAGAAATAGAATAGCAAAATAAACTCAA

AGAAAGCATAAAAAAAGAAACTGGTGGAACGGGAAACACACGTAGACGGGTATCCGATC

AAGCTT-3' SEQ ID NO: 4

EXAMPLE: EVIDENCE BASED ON VITAL CULTURE OF STEALTH VIRUS INFECTION IN BLOOD OF ADDITIONAL CFS PATIENTS

A large number of patients diagnosed with CFS have been tested for stealth virus infection using the culture method described in detail in this Section.

TABLE 4

Sequence of PCR amplified product derived from stealth virus from patient D. W. The product was amplified using a single EBV reactive primer, cloned into pbluescript and sequenced as described above. The plasmid is designated number 7.

5'-
TATCGATAAGCTTGATTTCGCGTTGCTAGGCCACCACTAATGCATGATTTTTCTTTCAAA

TATACCAACACATAAAATACGATAGTAGCCACACAGCAACAAATAATGAAATCATGTACC

GAAGAGGTTCAGGTCCAGTTAAAAATAGAAAAGTATGAATAAAGTGCCTCCATCCCTTAG

GGAATTCGATTTCGCGTTGCTAGGCCACCGCTTTGTTTTTTGCAATCTCCTACGGTAAAA

GTAATACAAGGGAATGGAGAGCCGCCGCTCGATACGCACTAGCACTGCAATTGGAAATTC

TABLE 4-continued

Sequence of PCR amplified product derived from stealth virus from patient D. W.
The product was amplified using a single EBV reactive primer, cloned into pbluescript
and sequenced as described above. The plasmid is designated number 7.

GATCCAAAGAAGAACCGTGGACGCCACTTGAACCTCGCATATTTCAGCGCGTGTATTTGG

AACACGACACGACTTCCCAACTCAACAATGATCAACTACATGTCAGCGGAACTGTGATTG

GAAATTTTACAAATACAGCTTGGATGCATGTTAGTCTGAGTTATCCTAAGTTCAAGGAAA

TGTTCGTCATGTCTACCAACCCAGACATCACAGTGAA-3' SEQ ID NO: 5

6.1 EXAMPLE EVIDENCE OF MOLECULAR HETEROGENEITY AMONG DIFFERENT ISOLATES OF STEALTH VIRUSES

Partial sequencing of the stealth virus from patient D. W. has been completed and virus specific primers made. The question was raised whether these viral sequences were detectable in other stealth viral isolates. The viral cultures isolated from patients B. H., J. T., T. R., G. P. and two CFS patients (N. R. and L. B.) were analyzed using, PCR assays. The primers included the HTLV tax gene primers (SK43' and SK44" and the specific primers based on the sequences in plasmids 15-5-2 and 15-5-4 containing PCR products amplified from cultures from patient D. W.

6.1 MATERIALS AND METHODS

PCR assays and the cloning and the sequencing of PCR products was as described supra.

6.2 RESULTS

The SK43' and SK44" primers generated PCR products from the various stealth viral cultures. When examined on agarose gels, however, only the culture from patient B. H. gave a banding pattern similar to that seen with the viral culture from patient D. W. This finding was consistent with the previously observed cross-hybridization seen with labeled PCR products between these two cultures. PCR products could also be generated on the culture from patient B. H., using the primers based on the sequences of the cloned plasmids obtained from the virus infecting patient D. W. In spite of this molecular similarity, at least in the regions so far examined, the fine details of the CPE associated with the viruses from patients D. W. and B. H. show clear differences. For example, the size of the cell syncytia is larger in cultures from patient D. W.

A PCR product of about 600 bp which was generated using the SK43' and SK44" primer set on the culture of the patient L. B. was cloned and sequenced (Clone 18). The PCR product contained both the SK43' and the SK44" primer sequences. This: is in contrast to the situation with the cloned PCR products generated from the cultures from patient D. W., which contain either the SK43' or the SK44" primer, but not both. The sequence of the product derived from the L. B. culture is shown in Table. It shows no relationship to known viruses or to the previously sequenced PCR products from patient D. W. In spite of this, the electron microscopic appearance is quite similar to that of the virus from both patients D. W. and B. H.

TABLE 5

Sequence of PCR Product Generated Using the
SK43' and SK44" Primers Stealth Virus Culture From Patient L. B.

AAGCTTGATCGGATACCCCGTCTACGTGTAACACCTGGAAAGTTAATGTT

CAGTGAAGCGCCCCAATGTCGCTGAATCCACCCAGCTCCTCACCTGCAAG

TTGGCCAACATGATGTGTCAAGTTGGGGACATGAATGCTTGTCCCACCTG

CCCTGGGAGAAAAGATCATAGAAGTGAAATGACCTTCTAAACAGCAAAGT

CCTGTGCAAATATAATGGTCCTTGTTGAGTCTTTTCCACATTCATAATCG

ATGTTTGTCTGACGCTGACCCCTGCTCCAGAACCACCCCCCCCACTCCCC

GGTCTGCTGTCGGGGAGCGCCAGGACACACTTGGCTCTTGGGCAGTTTTA

AGTAGGTTTAACGTTCTCACACTGATAGAAGTGGTGTACTTTAAAGATGA

ATTAAAATGAATACTTTATTAGTAACTCAGCTGTGCTTACTGCTAGATTC

CTTAAAATAATGCCCCTGCCTTTCCCACAATGACAGGGCTTGAATTTCTT

TABLE 5-continued

Sequence of PCR Product Generated Using the SK43' and SK44" Primers Stealth Virus Culture From Patient L. B.

TTTTTGCGAAGTGTGGTGGTGAGTCACAATCATTTCCGATGGACGCGTTG

TCAGCTCATCGAATTCC SEQ ID NO: 6

6.3 CONCLUSION

These findings establish that various stealth viruses may differ in their genetic composition. In spite of this difference, the viruses show common characteristics when cultured in fibroblasts. A homologous genetic region responsible for the common biological property, such as the induction of foamy cells in vitro, is anticipated to be found with additional sequencing. An advantage of sequence heterogeneity among isolates is that it can be used to trace disease transmission.

Deposit Of Microorganisms

The stealth virus isolated from patient D. W. (virus-X infected MRC-5 cells) was deposited with the American Type Culture Collection (ATCC)—12301 Parklawn Drive, Rockville, Md. 20852, under the provisions of the Budapest Treaty on the International Recognition of the Deposit of Microorganisms for the Purposes of Patent Procedures on 9-17-91, and were assigned accession no. VR-2343.

The present invention is not to be limited in scope by the microorganisms deposited or the specific embodiments described herein since such embodiments are intended as but single illustrations of one aspect of the invention and any microorganisms which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various references are cited herein, the disclosures of which are incorporated by reference herein in their entirety. In particular Martin, et al. *The American Journal of Pathology*, 145(2): 440–451, 1994 and Appendix A attached hereto as part of the specification are both incorporated herein by reference in their entirety, including any drawings.

What is claimed is:

1. An isolated, purified or enriched stealth virus nucleic acid molecule corresponding to at least a portion of a stealth virus nucleic acid sequence in the MRC-5 cell line, ATCC accession number VR2343, obtained by a method comprising:

(a) amplification of nucleic acid sequences from a virus infected culture of cells by low stringency polymerase chain reaction (PCR) to produce PCR amplified nucleic acid sequences, and;

(b) isolation of said PCR amplified nucleic acid sequences.

* * * * *

UNITED STATES PATENT AND TRADEMARK OFFICE
CERTIFICATE OF CORRECTION

PATENT NO. : 5,703,221

DATED : December 30, 1997

INVENTOR(S) : William John Martin

It is certified that error appears in the above-identified patent and that said Letters Patent is hereby corrected as shown below:

Column 2, Line 18: delete "specific" and insert --reactive--

Column 6, Line 14 and 15: delete "51 or 31" and insert --T5-T3--

Column 9, Line 36: delete "Delbecco's" and insert --Dulbecco--

Column 11, Line 9: delete "Coning of PCr" and insert --Cloning of PCR--

Column 11, Line 17: delete "51" and insert --T5--

Column 11, Line 22: delete "pbluescript" and insert --pBluescript--

Signed and Sealed this

Fifteenth Day of May, 2001

*Attest:*

NICHOLAS P. GODICI

*Attesting Officer*   Acting Director of the United States Patent and Trademark Office